US006867207B2

(12) United States Patent
Lacrampe et al.

(10) Patent No.: US 6,867,207 B2
(45) Date of Patent: Mar. 15, 2005

(54) IL-5 INHIBITING 6-AZAURACIL DERIVATIVES

(75) Inventors: Jean Fernand Armand Lacrampe, Le Mesnil Esnard (FR); Eddy Jean Edgard Freyne, Rumst (BE); Marc Gaston Venet, Le Mesnil Esnard (FR); Gustaaf Maria Boeckx, Oud-Turnhout (BE)

(73) Assignee: Janssen Pharmaceutica N.V. (BE)

(*) Notice: Subject to any disclaimer, the term of this patent is extended or adjusted under 35 U.S.C. 154(b) by 0 days.

(21) Appl. No.: 09/891,888

(22) Filed: Jun. 26, 2001

(65) Prior Publication Data

US 2002/0072603 A1 Jun. 13, 2002

Related U.S. Application Data

(63) Continuation of application No. 09/462,320, filed as application No. PCT/EP98/04191 on Jul. 7, 1998.

(30) Foreign Application Priority Data

Jul. 10, 1997 (EP) .......................................... 97202118

(51) Int. Cl.[7] .................... C07D 253/065; A61K 31/53; A61K 17/00; A61P 37/08

(52) U.S. Cl. .................... 514/242; 514/227.8; 544/182; 544/112; 544/60

(58) Field of Search ................................ 544/182, 112, 544/60; 514/242, 227.8, 235.8

(56) References Cited

U.S. PATENT DOCUMENTS

| | | | | |
|---|---|---|---|---|
| 3,883,528 | A | 5/1975 | Mylari | 544/182 |
| 3,912,723 | A | 10/1975 | Miller | 260/248 |
| 4,631,278 | A | 12/1986 | Boeckx et al. | |
| 4,767,760 | A | 8/1988 | Boeckx et al. | |
| 5,256,631 | A | 10/1993 | Lindner et al. | 544/182 |

FOREIGN PATENT DOCUMENTS

| | | |
|---|---|---|
| DE | 2 149 645 | 9/1972 |
| EP | 0 170 316 | 2/1986 |
| EP | 0 232 932 | 8/1987 |
| EP | 0 476 439 | 3/1992 |
| EP | 0 648 760 | 4/1995 |
| EP | 0831088 B1 | 3/1998 |

OTHER PUBLICATIONS

Mishra et al. Journal of Immunology, 2464–2469, 2002.*

Baggiolini, et al., "CC Chemokines in Allergic Inflammation." *Immunology Today*, 1994, pp. 127–133, vol. 15, No. 3.

Carr et al., "Expression On Porcine y δ lymphocytes Of A Phytogenetically Conserved Surface Antigen Previously Restricted in Expression y δ T Lymphocytes." *Immunology*, 1994, pp. 36–40, vol.81.

Minnicozzi, M., "The Inhibition of Interleukin 5 in allergic diseases." *Expert Opinion on Therapeutic Patents*, 1999, pp. 148–156, vol. 9(2).

PCT International Search Report for PCT Appln. No. PCT/EP 98/04191, mailed Nov. 17, 1998, which relates to this corresponding U.S. Application, filed herewith.

* cited by examiner

*Primary Examiner*—Venkataraman Balasubramanian
(74) *Attorney, Agent, or Firm*—Gabriel Lopez; Alana G. Kriessman

(57) ABSTRACT

The present invention is concerned with the compounds of formula (I)

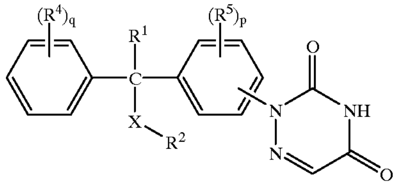

the N-oxides, the pharmaceutically acceptable addition salts and the stereochemically isomeric forms thereof, p and q are 0, 1, 2, 3 or 4 and q is also 5; X is O, S, $NR^3$ or a direct bond; $R^1$ is hydrogen, hydroxy, halo, optionally substituted amino, optionally substituted $C_{1-6}$alkyl, $C_{1-6}$alkyloxy, $C_{3-7}$cycloalkyl or aryl; $R^2$ is aryl, $Het^1$, $C_{3-7}$cycloalkyl, optionally substituted $C_{1-6}$alkyl; and if X is O, S or $NR^3$, then $R^2$ may also be a carbonyl or thiocarbonyl linked substituent; $R^3$ is hydrogen or $C_{1-4}$alkyl; $R^4$ and $R^5$ independently are optionally substituted $C_{1-6}$alkyl, halo, hydroxy, mercapto, $C_{1-6}$alkyloxy, $C_{1-6}$akylthio, $C_{1-6}$alkylcarbonyloxy, aryl, cyano, nitro, $Het^3$, $R^6$ or $NR^7R^8$; $R^6$ is substituted sulfonyl or sulfinyl; $R^7$ and $R^8$ are hydrogen, optionally substituted $C_{1-4}$alkyl, aryl, a carbonyl or thiocarbonyl linked substituent, $C_{3-7}$cycloalkyl, $Het^3$ and $R^6$; $R^9$ and $R^{10}$ are each independently selected from hydrogen, optionally substituted $C_{1-4}$alkyl, phenyl, a carbonyl or thiocarbonyl linked substituent, $C_{3-7}$cycloalkyl, $Het^3$ and $R^6$; $R^{11}$ is hydroxy, mercapto, cyano, nitro, halo, trihalomethyl, $C_{1-4}$alkyloxy, carboxyl, $C_{1-4}$alkyloxycarbonyl, trihalo$C_{1-4}$alkylsulfonyloxy, $R^6$, $NR^7R^8$, $C(=O)NR^7R^8$, aryl, aryloxy, arylcarbonyl, $C_{3-7}$cycloalkyl, $C_{3-7}$cycloalkyloxy, phthalimide-2-yl, $Het^3$ and $C(=O)Het^3$; $R^{12}$ and $R^{13}$ are each independently selected from hydrogen, optionally substituted $C_{1-4}$alkyl, phenyl, a carbonyl or thiocarbonyl linked substituent, $C_{3-7}$cycloalkyl and $R^6$; aryl is optionally substituted phenyl; $Het^1$, $Het^2$ and $Het^3$ are optionally substituted heterocycles; to processes for their preparation and compositions comprising them. It further relates to their use as a medicine.

7 Claims, No Drawings

IL-5 INHIBITING 6-AZAURACIL DERIVATIVES

CROSS REFERENCE TO RELATED APPLICATIONS

This application is a continuation of application Ser. No. 09/462,320, filed Jan. 5, 2000 which is the National Stage application under 35 U.S.C. 371 of PCT/EP98/04191 filed Jul. 7, 1998, which claims priority from EP 97.202.118.2, filed Jul. 10, 1997.

The present invention concerns novel IL-5 inhibiting 6-azauracil derivatives useful for treating eosinophil-dependent inflammatory diseases; to processes for their preparation and compositions comprising them. It further relates to their use as a medicine.

Eosinophil influx, leading to subsequent tissue damage, is an important pathogenic event in bronchial asthma and allergic diseases. The cytokine interleukin-5 (IL-5), produced mainly by T lymphocytes as a glycoprotein, induces the differentiation of eosinophils in bone marrow and, primes eosinophils for activation in peripheral blood and sustains their survival in tissues. As such, IL-5 plays a critical role in the process of eosinophilic inflammation. Hence, the possibility that inhibitors of IL-5 production would reduce the production, activation and/or survival of eosinophils provides a therapeutic approach to the treatment of bronchial asthma and allergic diseases such as, atopic dermatitis, allergic rhinitis, allergic conjunctivitis, and also other eosinophil-dependent inflammatory diseases.

Steroids, which strongly inhibit IL-5 production in vitro, have long been used as the only drugs with remarkable efficacy for bronchial asthma and atopic dermatitis, but they cause various serious adverse reactions such as diabetes, hypertension and cataracts. Therefore, it would be desirable to find non-steroidal compounds having the ability to inhibit IL-5 production in human T-cells and which have little or no adverse reactions.

U.S. Pat. No. 4,631,278 discloses a-aryl-4-(4,5-dihydro-3,5-dioxo-1,2,4-triazin-2(3H)-yl)benzeneacetonitriles and U.S. Pat. No. 4,767,760 discloses 2-(substituted phenyl)-1,2,4-triazine-3,5(2H,4H)-diones, all having anti-protozoal activity, in particular, anticoccidial activity. EP 831,088 discloses 1,2,4-triazine-3,5-diones as anticoccidial agents. Unexpectedly, the 6-azauracil derivatives of the present invention prove to be potent inhibitors of the production of IL-5.

The present invention is concerned with the compounds of formula (I)

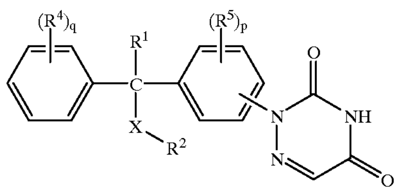

the N-oxides, the pharmaceutically acceptable addition salts and the stereochemically isomeric forms thereof, wherein:

p represents an integer being 0, 1, 2, 3 or 4;

q represents an integer being 0, 1, 2, 3, 4 or 5;

X represents O, S, $NR^3$ or a direct bond;

$R^1$ represents hydrogen, hydroxy, halo, amino, mono- or di($C_{1-4}$alkyl)amino, $C_{1-6}$alkyl $C_{1-6}$alkyloxy, $C_{3-7}$cycloakyl, aryl, aryl$C_{1-6}$alkyl, amino$C_{1-4}$alkyl, mono- or di($C_{1-4}$alkyl)amino$C_{1-4}$alkyl or mono- or di($C_{1-4}$ alkyl)amino$C_{1-4}$alkylamino;

$R^2$ represents aryl, $Het^1$, $C_{3-7}$cycloalkyl, $C_{1-6}$alkyl or $C_{1-6}$alkyl substituted with one or two substituents selected from hydroxy, cyano, amino, mono- or di($C_{1-4}$alkyl) amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$, $Het^1$oxy and $Het^1$thio; and if X is O, S or $NR^3$, then $R^2$ may also represent aminocarbonyl, aminothiocarbonyl, $C_{1-4}$alkylcarbonyl, $C_{1-4}$alkylthiocarbonyl, arylcarbonyl or arylthiocarbonyl;

$R^3$ represents hydrogen or $C_{1-4}$alkyl;

each $R^4$ independently represents $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with $Het^3$, $R^6$ or $NR^7R^8$;

each $R^5$ independently represents $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with $Het^3$, $R^6$ or $NR^7R^8$;

each $R^6$ independently represents $C_{1-6}$alkylsulfonyl, aminosulfonyl, mono- or di-($C_{1-4}$alkyl)aminosulfonyl, mono- or di(benzyl)aminosulfonyl, polyhalo$C_{1-6}$ alkylsulfonyl, $C_{1-6}$alkylsulfinyl, phenyl$C_{1-4}$ alkylsulfonyl, piperazinylsulfonyl, aminopiperidinylsulfonyl, piperidinylaminosulfonyl, N-$C_{1-4}$alkyl-N-piperidinylaminosulfonyl;

each $R^7$ and each $R^8$ are independently selected from hydrogen, $C_{1-4}$alkyl, hydroxy-$C_{1-4}$alkyl, dihydroxy$C_{1-4}$ alkyl, aryl, aryl$C_{1-4}$alkyl, $C_{1-4}$alkyloxy$_{1-4}$alkyl, $C_{1-4}$alkylcarbonyl, arylcarbonyl, $C_{1-4}$alkylcarbonyloxy$C_{1-4}$alkylcarbonyl, hydroxy$C_{1-4}$ alkylcarbonyl, $C_{1-4}$alkyloxycarbonylcarbonyl, mono- or di($C_{1-4}$alkyl)amino$C_{1-4}$alkyl, arylaminocarbonyl, arylaminothiocarbonyl, $Het^3$aminocarbonyl, $Het^3$aminothiocarbonyl, $C_{3-7}$cycloalkyl, pyridinyl$C_{1-4}$ alkyl, $Het^3$ and $R^6$;

$R^9$ and $R^{10}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, $C_{1-4}$alkylcarbonyloxy$C_{1-4}$alkylcarbonyl, hydroxy$C_{1-4}$ alkylcarbonyl, $C_{1-4}$alkyloxycarbonylcarbonyl, mono- or di($C_{1-4}$alkyl)amino$C_{1-4}$alkyl, phenylaminocarbonyl, phenylaminothiocarbonyl, $Het^3$aminocarbonyl, $Het^3$aminothiocarbonyl, $C_{3-7}$cycloalkyl, pyridinyl$C_{1-4}$ alkyl, $Het^3$ and $R^6$;

each $R^{11}$ independently being selected from hydroxy, mercapto, cyano, nitro, halo, trihalomethyl, $C_{1-4}$alkyloxy, carboxyl, $C_{1-4}$alkyloxycarbonyl, trihalo$C_{1-4}$ alkylsulfonyloxy, $R^6$, $NR^7R^8$, C(=O)$NR^7R^8$, aryl, aryloxy, arylcarbonyl, $C_{3-7}$cycloalkyl, $C_{3-7}$cycloalkyloxy, phthalimide-2-yl, $Het^3$ and C(=O)$Het^3$;

$R^{12}$ and $R^{13}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, phenylcarbonyl, $C_{1-4}$ alkylcarbonyloxy$C_{1-4}$alkylcarbonyl, hydroxy$C_{1-4}$ alkylcarbonyl, $C_{1-4}$alkyloxycarbonylcarbonyl, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl and $R^6$;

aryl represents phenyl optionally substituted with one, two or three substituents each independently selected from nitro, azido, halo, hydroxy, $C_{1-4}$alkyl $C_{1-4}$alkyloxy, polyhalo$C_{1-4}$alkyl, $NR^9R^{10}$, $R^6$, phenyl, $Het^3$ and $C_{1-4}$alkyl substituted with $NR^9R^{10}$;

$Het^1$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl, imidazo[2,1-b]thiazolyl; wherein said heterocycles each independently may optionally be substituted with one, or where possible, two or three substituents each independently selected from $Het^2$, $R^{11}$ and $C_{1-4}$alkyl optionally substituted with $Het^2$ or $R^{11}$;

$Het^2$ represents a monocyclic heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl and triazinyl; wherein said monocyclic heterocycles each independently may optionally be substituted with one, or where possible, two or three substituents each independently selected from $R^{11}$ and $C_{1-4}$alkyl optionally substituted with $R^{11}$;

$Het^3$ represents a monocyclic heterocycle selected from pyrrolidinyl, piperidinyl, piperazinyl, morpholinyl, thiomorpholinyl; wherein said monocyclic heterocycles each independently may optionally be substituted with, where possible, one, two or three substituents each independently selected from $C_{1-4}$alkyl, $C_{1-4}$alkyloxy, carboxyl, $C_{1-4}$alkyloxycarbonyl, $C_{1-4}$alkylcarbonyl, phenyl$C_{1-4}$alkyl, piperidinyl, $NR^{12}R^{13}$, $R^6$ and $C_{1-4}$alkyl substituted with $R^6$ or $NR^{12}R^{13}$.

As used in the foregoing definitions and hereinafter, halo is generic to fluoro, chloro, bromo and iodo; $C_{3-7}$cycloalkyl is generic to cyclopropyl, cyclobutyl, cyclopentyl, cyclohexyl and cycloheptyl; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl is meant to include $C_{1-4}$alkyl and the higher homologues thereof having 5 or 6 carbon atoms such as, for example, pentyl, 2-methylbutyl, hexyl, 2-methylpentyl and the like; polyhalo$C_{1-4}$alkyl is defined as polyhalosubstituted $C_{1-4}$alkyl, in particular $C_{1-4}$alkyl substituted with 1 to 6 halogen atoms, more in particular difluoro- or trifluoromethyl; polyhalo$C_{1-6}$alkyl is defined as polyhalosubstituted $C_{1-6}$alkyl.

$Het^1$, $Het^2$ and $Het^3$ are meant to include all the possible isomeric forms of the heterocycles mentioned in the definition of $Het^1$, $Het^2$ or $Het^3$, for instance, pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

The heterocycles represented by $Het^1$, $Het^2$ and $Het^3$ may be attached to the remainder of the molecule of formula (I) through any ring carbon or heteroatom as appropriate. Thus, for example, when the heterocycle is imidazolyl, it may be a 1-imidazolyl, 2-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzthiazolyl, it may be 2-benzthiazolyl, 4-benzthiazolyl, 5-benzthiazolyl, 6-benzthiazolyl and 7-benzthiazolyl.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be, converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such firms are e.g. hydrates, alcoholates and the like.

The N-oxide forms of the present compounds are meant to comprise the compounds of formula (I) wherein one or several nitrogen atoms are oxidized to the so-called N-oxide. For example, one or more nitrogen atoms of any of the heterocycles in the definition of $Het^1$, $Het^2$ and $Het^3$ may be N-oxidized.

Some of the compounds of formula (I) may also exist in their tautomeric forms. Such forms although not explicitly indicated in the above formula are intended to be included within the scope of the present invention. For example, a hydroxy substituted triazine moiety may also exist as the corresponding triazinone moiety; a hydroxy substituted pyrimidine moiety may also exist as the corresponding pyrimidinone moiety.

The term "stereochemically isomeric forms" as used hereinbefore defines all the possible stereoisomeric forms in which the compounds of formula (I) can exist. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration, used herein in accordance with Chemical Abstracts nomenclature. Stereochemically isomeric forms of the compounds of formula (I) are obviously intended to be embraced within the scope of this invention.

The compounds of formula (I) and some of the intermediates in the present invention contain one or more asymmetric carbon atoms. The pure and mixed stereochemically isomeric forms of the compounds of formula (I) are intended to be embraced within the scope of the present invention.

Whenever used hereinafter, the term "compounds of formula (I)" is meant to also include their N-oxide forms, their pharmaceutically acceptable addition salts, and their stereochemically isomeric forms.

The numbering of the phenyl ring bearing substituent $R^4$ is given hereinbelow and is used herein as such when indicating the position of the $R^4$ substituents on said phenyl ring, unless otherwise indicated.

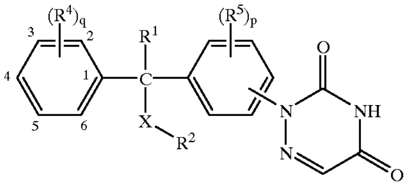

The carbon atom bearing the two phenyl rings and the $R^1$ and —X—$R^2$ substituents will be referred herein as the central carbon atom.

A special group of compounds are those compounds of formula (I) wherein $R^1$ represents hydrogen, hydroxy, halo, amino, mono- or di($C_{1-4}$alkyl)amino, $C_{1-6}$alkyl, $C_{1-6}$alkyloxy, $C_{3-7}$cycloalkyl, aryl or aryl$C_{1-6}$alkyl; $R^2$ represents aryl; $Het^1$; $C_{3-7}$cycloalkyl; $C_{1-6}$alkyl or $C_{1-6}$alkyl substituted with one or two substituents selected from hydroxy, cyano, amino, mono- or di($C_{1-4}$alkyl)amino, $C_{1-6}$alkyloxy, $C_{1-6}$alkyloxycarbonyl, $C_{3-7}$cycloalkyl, aryl and $Het^1$; and if X is $NR^3$, then $R^2$ may also represent $C_{1-4}$alkylcarbonyl or arylcarbonyl; each $R^4$ independently represents halo, polyhalo$C_{1-6}$alkyl, $C_{1-6}$alkyl, hydroxy, $C_{1-6}$alkyloxy, $C_{1-6}$alkylcarbonyloxy, mercapto, $C_{1-6}$alkylthio, $C_{1-6}$alkylsulfonyl, $C_{1-6}$alkylsulfinyl, polyhalo$C_{1-6}$alkylsulfonyl, aryl, cyano, nitro, amino, mono- and di($C_{1-6}$alkyl)amino or ($C_{1-6}$alkylcarbonyl)amino; each $R^5$ independently represents halo, polyhalo$C_{1-6}$alkyl, $C_{1-6}$alkyl, hydroxy, $C_{1-6}$alkyloxy, $C_{1-6}$alkylcarbonyloxy, mercapto, $C_{1-6}$alkylthio, $C_{1-6}$alkylsulfonyl, $C_{1-6}$alkylsulfinyl, polyhalo$C_{1-6}$alkylsulfonyl, aryl, cyano, nitro, amino, mono- and di($C_{1-6}$alkyl)amino or ($C_{1-6}$alkylcarbonyl)amino; aryl represents phenyl or phenyl substituted with one, two or three substituents selected from halo, hydroxy, $C_{1-4}$alkyl, $C_{1-4}$alkyloxy, polyhalo$C_{1-4}$alkyl, amino, mono- or di($C_{1-4}$alkyl)amino and phenyl; $Het^1$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, piperidinyl, piperazinyl, morpholinyl, thiomorpholinyl, dioxanyl, dithianyl, dithianyl, triazinyl, benzothienyl, isobenzothienyl, benzofuranyl, isobenzofuranyl, benzthiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl and thiazolopyridinyl; said heterocycles each independently may be substituted with one, or where possible, two or three $R_{11}$ substituents, each $R^{11}$ independently being selected from hydroxy, mercapto, cyano, nitro, $C_{1-4}$alkyl, $C_{1-4}$alkyloxy, amino, mono- or di($C_{1-4}$alkyl) amino, mono- or di($C_{1-4}$alkyl)aminocarbonyl, mono- or di(aryl) amino, halo, polyhalo$C_{1-4}$alkyl, $C_{1-4}$alkyloxycarbonyl, aryl, furanyl, thienyl, pyridinyl, piperidinyl, $C_{1-4}$alkyl-carbonylpiperidinyl and $C_{1-4}$alkyl substituted with $C_{1-4}$alkyloxy, aryl, hydroxy, piperidinyl, amino, mono- or di($C_{1-4}$alkyl)amino or $C_{3-7}$cycloalkyl.

An interesting group of compounds are those compounds of formula (I) wherein the 6-azauracil moiety is connected to the phenyl ring in the para or meta position relative to the central carbon atom; preferably in the para position.

Suitably, p is 0, 1 or 2; preferably 1 or 2.

Suitably, q is 0, 1 or 2; preferably 1 or 2.

Suitably, $R^1$ represents hydrogen, hydroxy, halo, amino, $C_{1-6}$alkyl, $C_{1-6}$alkyloxy or mono- or di($C_{1-4}$alkyl)amino$C_{1-4}$ alkylamino; in particular, hydrogen, methyl and hydroxy.

Suitably, $R^2$ represents aryl, $Het^1$, $C_{3-7}$cycloalkyl, $C_{1-6}$alkyl or $C_{1-6}$alkyl substituted with one or two substituents selected from hydroxy, cyano, amino, mono- or di($C_{1-4}$ alkyl)amino, $C_{1-6}$alkyloxy, $C_{1-6}$alkylsulfonyloxy, $C_{1-6}$alkyloxycarbonyl, aryl, $Het^1$ and $Het^1$thio; and if X is $NR^3$, then $R^2$ may also represent arylcarbonyl.

Suitably, $R^3$ represents hydrogen or methyl.

Suitably, each $R^4$ independently represents $C_{1-6}$alkyl, halo, polyhalo$C_{1-6}$alkyl or $C_{1-6}$alkyloxy.

Suitably, each $R^5$ independently represents $C_{1-6}$alkyl, halo or $C_{1-6}$alkyloxy.

Suitably, each $R^6$ independently represents $C_{1-6}$alkylsulfonyl, aminosulfonyl or phenyl$C_{1-4}$ alkylsulfonyl.

Suitably, each $R^7$ and each $R^8$ are independently selected from hydrogen, $C_{1-4}$alkyl, hydroxy$C_{1-4}$alkyl, dihydroxy$C_{1-4}$ alkyl, aryl, aryl$C_{1-4}$alkyl, $C_{1-4}$alkyloxy$C_{1-4}$alkyl, mono- or di($C_{1-4}$alkyl)amino$C_{1-4}$alkyl, arylaminocarbonyl, arylaminothiocarbonyl, $C_{3-7}$cycloalkyl, pyridinyl$C_{1-4}$alkyl, $Het^3$ and $R^6$.

Suitably, $R^9$ and $R^{10}$ are each independently selected from hydrogen, $C_{1-4}$alkyl, $C_{1-4}$alkylcarbonyloxy$C_{1-4}$ alkylcarbonyl, hydroxy$C_{1-4}$alkylcarbonyl, $C_{1-4}$alkyloxy carbonylcarbonyl, $Het^3$aminothiocarbonyl and $R^6$.

Suitably, $R^{12}$ and $R^{13}$ are each independently selected from hydrogen and $C_{1-4}$alkyl. Suitably, $Het^1$ represents a heterocycle selected from imidazolyl, triazolyl, furanyl, oxazolyl, thiazolyl, thiazolinyl, thiadiazolyl, oxadiazolyl, pyridinyl, pyrimidinyl, pyrazinyl, piperidinyl, piperazinyl, triazinyl, benzothiazolyl, benzoxazolyl, purinyl, 1H-pyrazolo-[3,4-d]pyrimidinyl, benzimidazolyl, thiazolopyridinyl, oxazolopyridinyl, imidazo-[2,1-b] thiazolyl; wherein said heterocycles each independently may optionally be substituted with one, or where possible, two or three substituents each independently selected from $Het^2$, $R^{11}$ and $C_{1-4}$alkyl optionally substituted with $Het^2$ or $R^{11}$. Suitably, $Het^2$ represents furanyl, thienyl or pyridinyl; wherein said monocyclic heterocycles each independently may optionally be substituted with $C_{1-4}$alkyl. Suitably, $Het^3$ represents pyrrolidinyl, piperidinyl, piperazinyl, morpholinyl, thiomorpholinyl; wherein said monocyclic heterocycles each independently may optionally be substituted with, where possible, one, two or three substituents each independently selected from $C_{1-4}$alkyl, $C_{1-4}$alkyloxy, $C_{1-4}$alkyloxycarbonyl, $C_{1-4}$alkylcarbonyl, phenyl$C_{1-4}$alkyl, piperidinyl, $NR^{12}R^{13}$ and $C_{1-4}$alkyl substituted with $NR^{12}R^{13}$.

Particular compounds are those compounds of formula (I) wherein $R^4$ and $R^5$ each independently are halo, polyhalo$C_{1-}$ 6alkyl, $C_{1-6}$alkyl, $C_{1-6}$alkyloxy or aryl, more in particular, chloro or trifluoromethyl.

Other particular compounds are those compounds of formula (I) wherein $R^2$ represents aryl, $Het^1$, $C_{3-7}$cycloalkyl or $C_{1-6}$alkyl substituted with one or two substituents selected from hydroxy, cyano, amino, mono- or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$, $Het^1$oxy and $Het^1$thio; and if X is O, S or $NR^3$, then $R^2$ may also represent aminocarbonyl, aminothiocarbonyl, $C_{1-4}$alkylcarbonyl, $C_{1-4}$alkylthiocarbonyl, arylcarbonyl or arylthiocarbonyl; more in particular $R^2$ is oxadiazolyl, thiazolyl, pyrimidinyl or pyridinyl; wherein said heterocycles each independently may optionally be, substituted with one, or where possible, two or three substituents each independently selected from $Het^2$, $R^{11}$ and $C_{1-4}$alkyl optionally substituted with $Het^2$ or $R^{11}$.

Yet other particular compounds are those compounds of formula (I) wherein X is O, S, NH or a direct bond, more preferably S or a direct bond, most preferably a direct bond.

Preferred compounds are those compounds of formula (I) wherein q is 1 or 2 and one $R^4$ substituent, preferably chloro, is in the 4 position.

Other preferred compounds are those compounds of formula (I) wherein p is 1 or 2 and the one or two $R^5$ substituents, preferably chloro, are in the ortho position relative to the central carbon atom.

More preferred compounds are those compounds of formula (I) wherein the 6-azauracil moiety is in the para position relative to the central carbon atom; p is 2 and both $R^5$ substituent are chloro positioned ortho relative to the central carbon atom; q is 1 and $R^4$ is chloro positioned in the 4 position.

Most preferred compounds include

2-[3,5-dichloro-4-[(4-chlorophenyl)(2-pyrimidinylthio)methyl]phenyl]-1,2,4-triazine-3,5(2H,4H)-dione;

2-[3,5-dichloro-4-[(4-chlorophenyl)[2-(4-pyridinyl)-4-thiazolyl]methyl]phenyl]-1,2,4-triazine-3,5(2H,4H)-dione monohydrochloride.monohydrate;

2-[3,5-dichloro-4-[(4-chlorophenyl)(5-phenyl-1,3,4-oxadizol-2-yl)methyl]phenyl]-1,2,4-triazine-3,5(2H,4H)-dione;

2-[3,5-dichloro-4-[(4-chlorophenyl)[4-(2-chlorophenyl)-2-thiazolyl]methyl]phenyl]-1,2,4-triazine-3,5(2H,4H)-dione;

2-[3,5-dichloro-4-[(4-chlorophenyl)[4-(3-fluorophenyl)-2-thiazolyl]methyl]phenyl]-1,2,4-triazine-3,5(2H,4H)-dione;

2-[3,5-dichloro-4-[(4-chlorophenyl)(2-pyridinylthio)methyl]phenyl]-1,2,4triazine-3,5(2H,4H)-dione; the N-oxides, the pharmaceutically acceptable addition salts and the stereochemically isomeric forms thereof.

In order to simplify the structural representation of the compounds of formula (I), the group

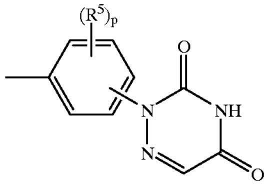

will hereinafter be represented by the symbol D.

Compounds of formula (I) can generally be prepared by reacting an intermediate of formula (II) wherein $W^1$ is a suitable leaving group such as, for example, a halogen atom, with an appropriate reagent of formula (III).

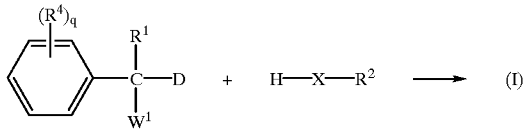

(II) (III)

Said reaction may be performed in a reaction-inert solvent such as, for example, acetonitrile, N,N-dimethylformamide, acetic acid, tetrahydrofuran, ethanol or a mixture thereof. Alternatively, in case the reagent of formula (III) acts as a solvent, no additional reaction-inert solvent is required. The reaction is optionally carried out in the presence of a base such as, for example, 1,8-diazabicyclo[5.4.0]undec-7-ene, sodium bicarbonate, sodiumethanolate and the like. Convenient reaction temperatures range between −70° C. and reflux temperature.

In this and the following preparations, the reaction products may be isolated from the reaction medium and, if necessary, further purified according to methodologies generally known in the art such as, for example, extraction, crystallization, distillation, trituration and chromatography.

Alternatively, compounds of formula (I) may generally be prepared by cyclizing an intermediate of formula (IV) wherein L is a suitable leaving group such as, for example, $C_{1-6}$alkyloxy or halo, and E represents an appropriate electron attracting group such as, for example, an ester, an amide, a cyanide, $C_{1-6}$alkylsulfonyloxy and the like groups; and eliminating the group E of the thus obtained triazinedione of formula (V). Said reaction procedure is analogous to the one described in EP-A-0,170,316.

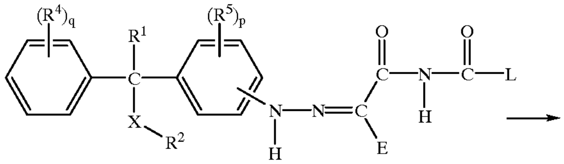

(IV)

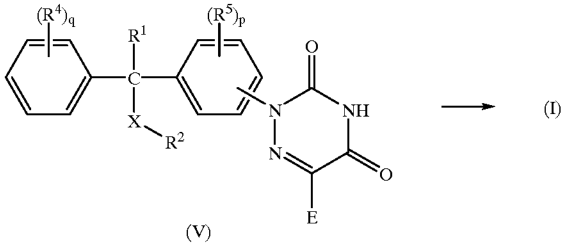

(V)

Some of the compounds and intermediates of the present invention can be prepared according to or analogous to the procedures described in EP-A-0,170,316 and EP-A-0,232,932.

For instance, scheme 1 depicts a reaction pathway for the preparation of compounds of formula (I) wherein $R^1$ is hydrogen and X is a direct bond, said compounds being represented by formula (I-a-1). A ketone of formula (VI) can be reacted with a reagent of formula (VII) wherein $W^2$ is a suitable leaving group such as, for example, a halogen, in a reaction-inert solvent such as, for example, tetrahydrofuran, diethylether, and in the presence of a suitable base such as, for example, butyl lithium, thus forming an intermediate of formula (VII). The hydroxy group of the intermediates of formula (VIII) may be eliminated by using a suitable reagent such as for example, formamide in acetic acid or triethylsilane in trifluoroacetic acid, thus obtaining an intermediate of formula (IX) of which the nitro group may subsequently be reduced to an amino group which in turn may then be converted to the 6-azauracil group as described in EP-A-0,170,316, thus obtaining compounds of formula (I-a-1).

Scheme 1

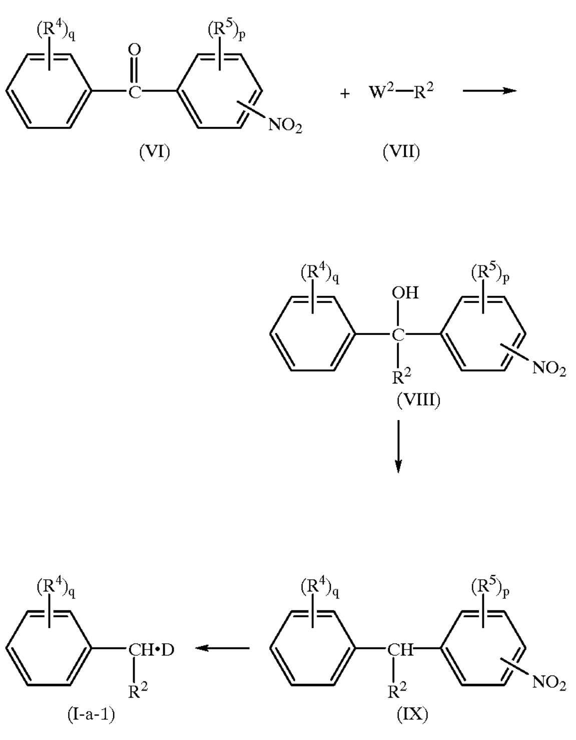

(VI) (VII) (VIII) (IX) (I-a-1)

In addition to the reaction procedure shown in scheme 1, other compounds of formula (I) wherein X is a direct bond may be prepared starting from a ketone of formula (X) (Scheme 2). Reacting said ketone of formula (X) with an intermediate of formula (III) wherein X is a direct bond, said intermediates being represented by formula (III-a), results in a compound of formula (I) wherein $R^1$ is hydroxy and X is a direct bond, said compounds being represented by formula (I-a-2). Said reaction may be performed in a reaction-inert solvent such as, for example, tetrahydrofuran, diethylether, diisopropyl-acetamide or a mixture thereof, in the presence of a base such as, for example, butyl lithium, and optionally in the presence of chlorotriethylsilane. Alternatively, intermediate of formula (III-a) may first be transformed into a Grignard reagent, which may then be reacted with the ketone of formula (X). Said compounds of formula (I-a-2) may further be converted to compounds of formula (I) wherein $R^1$ is a $C_{1-6}$alkyloxy group represented by formula (I-a-3) using art-known group transformation reactions. The compounds of formula (I-a-2) may also be converted to compounds of formula (I) wherein $R^1$ is halo, said compounds being represented by formula (I-a-4). A convenient procedure is converting the hydroxy group to a chlorine atom using a suitable reagent such as, for example, thionyl chloride. Said compounds of formula (I-a-4) may further be converted to compounds of formula (I) wherein $R^1$ is amino, said compounds being represented by formula (I-a-5), using ammonia or a functional derivative thereof, in a reaction-inert solvent such as, for example, tetrahydrofuran; or may be converted to compounds of formula (I-a-3) using art-known group transformation reactions. Reducing the ketone of formula (X) to its corresponding hydroxy derivative of formula (XI) using a suitable reducing agent such as, for example, sodiumborohydride in a reaction-inert solvent such as for example, water, an alcohol, tetrahydrofuran or a mixture thereof; subsequently converting said hydroxy group to a suitable leaving group $W^4$ being for example a halogen, thus obtaining an intermediate of formula (XII), and finally reacting said intermediate of formula (XII) with an intermediate of formula (III) in a suitable solvent such as, for example, tetrahydrofuran, N,N-dimethylformamide, acetonitrile, acetic acid, ethanol or a mixture thereof, and optionally in the presence of a suitable base such as, for example, 1,8-diazabicyclo[5.4.0]undec-7-ene or sodiumbicarbonate, will result in a compound of formula (I) wherein $R^1$ is hydrogen, said compounds being represented by formula (I-b).

Alternatively, intermediates of formula (XI) can be directly transformed to compounds of formula (I-b) wherein X is S, said compounds being represented by formula (I-b-1), using a suitable mercapto containing reagent of formula $R^2$—SH in a suitable reaction solvent such as, for example, trifluoroacetic acid, methanesulfonic acid, trifluoromethanesulfonic acid or the like.

Also starting from a ketone of formula (X), compounds of formula (I) may be prepared wherein $R^1$ is hydrogen and —X—$R^2$ is —NH—C(=O)-(aryl or $C_{1-6}$alkyl), said compounds being represented by formula (I-c). To that effect, a ketone of formula (X) is reacted with formamide in formic acid or a functional derivative thereof, at elevated temperatures. The resulting intermediate of formula (XIII) is hydrolysed to the corresponding amine of formula (XIV), which may then be further reacted with an intermediate of formula (XV) wherein $W^3$ is a suitable leaving group, in the presence of a suitable base, such as, for example pyridine, optionally in the presence of a reaction-inert solvent such as, for example, dichloromethane.

Scheme 2
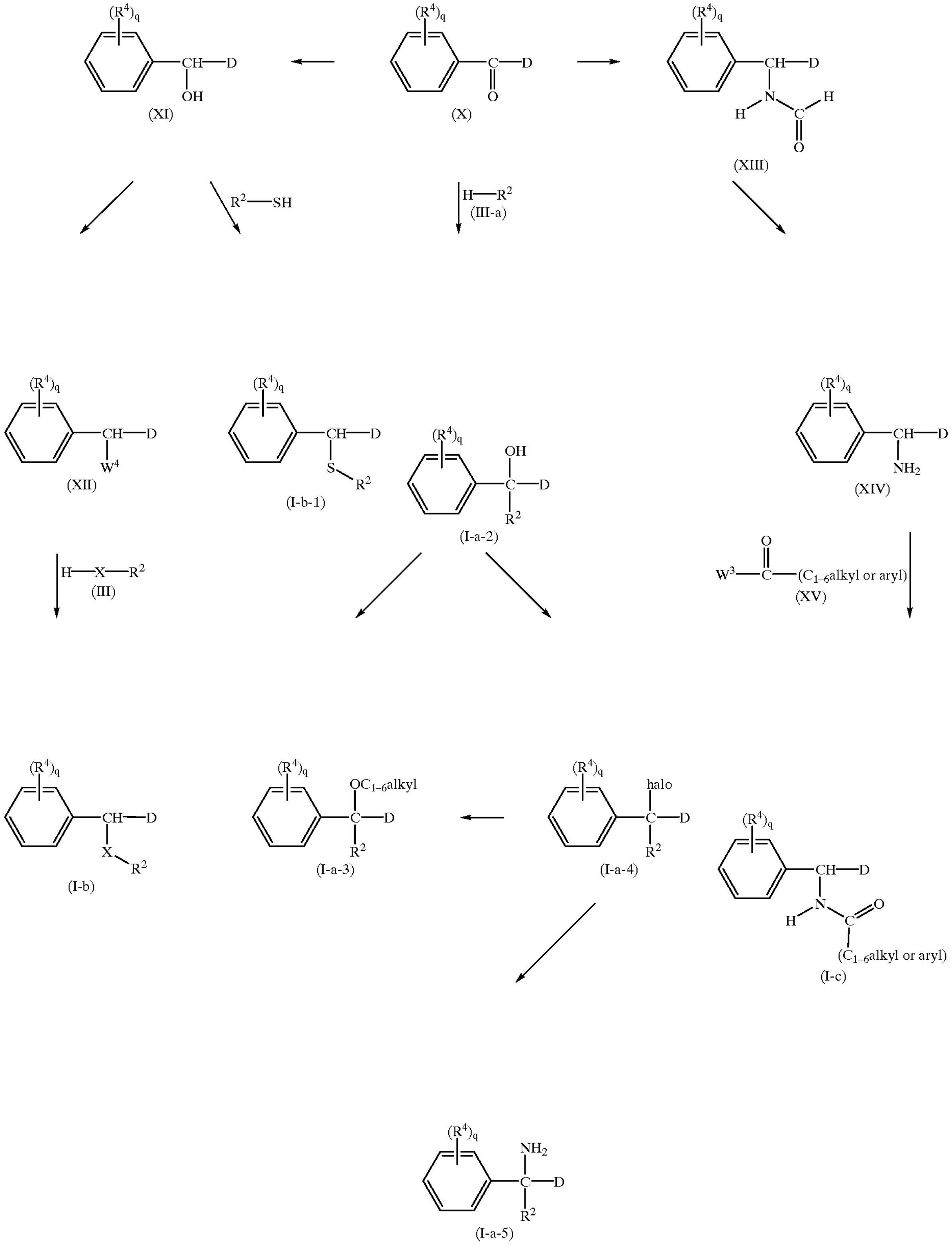

Compounds of formula (I) wherein X is a direct bond and $R^2$ is a heterocycle, said compounds being generally represented by formula (I-d), can conveniently be prepared by cyclization of the appropriate intermediate. Both intramolecular and intermolecular cyclization procedures are feasable and scheme 3 lists several examples.

Starting point is the conversion of the cyano group of an intermediate of formula (XVI) to a carboxyl group thus forming intermediates of formula (XVII) using art-known techniques such as, for example, using a combination of sulfuric- and acetic acid in water, which in turn may be further reacted to acyl halides of formula (XVIII), for instance, the acyl chloride derivative may be prepared using thionyl chloride.

Scheme 3

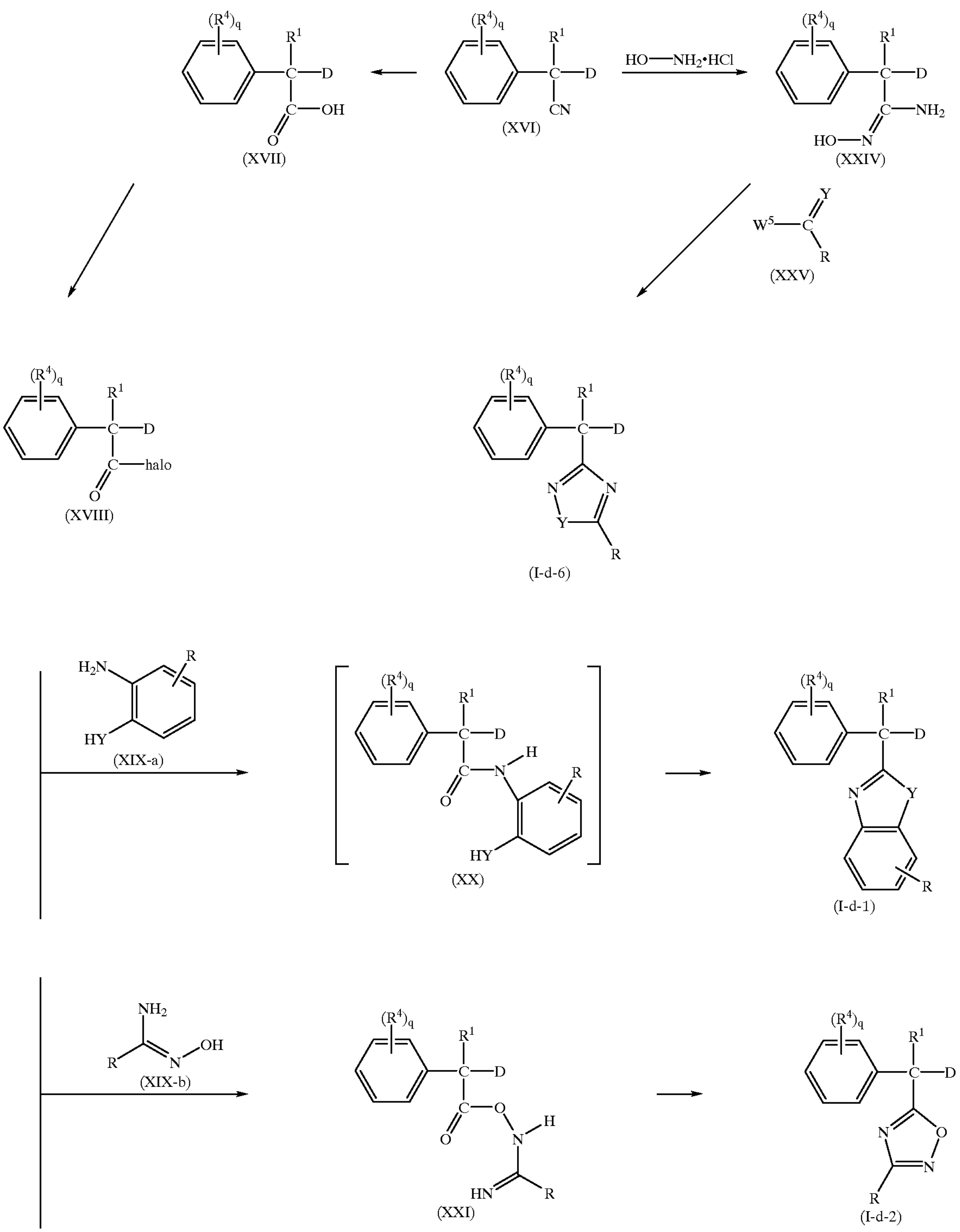

(XVII)
(XVI)
(XXIV)
(XXV)
(XVIII)
(I-d-6)
(XIX-a)
(XX)
(I-d-1)
(XIX-b)
(XXI)
(I-d-2)

-continued

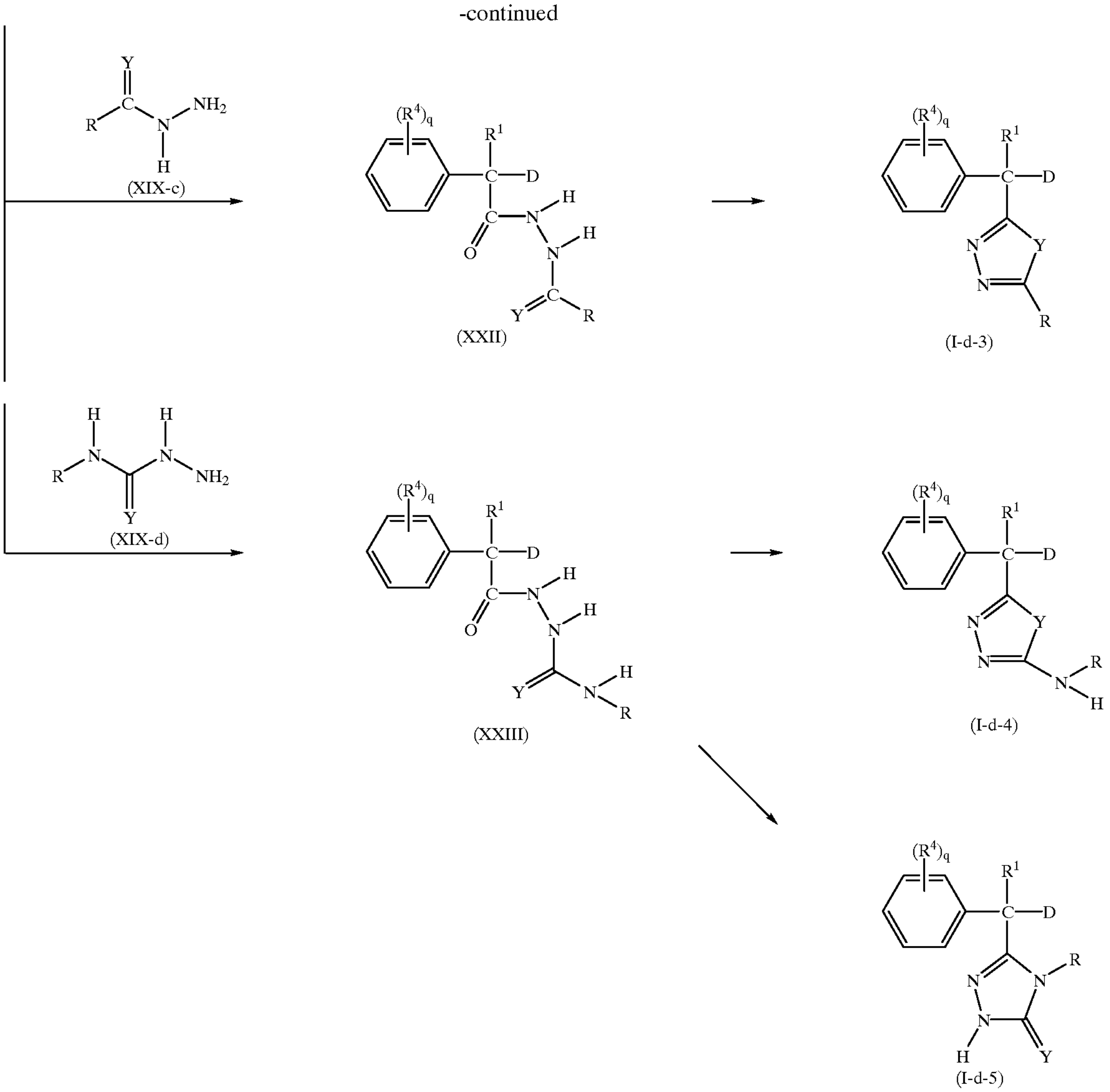

The intermediate of formula (XVIII) may be reacted with an intermediate of formula (XIX-a) wherein Y is O, S or $NR^3$, to form an intermediate of formula (XX) in the presence of a base such as, for example, pyridine. Said intermediate of formula (XX) may further be cyclized to a compound of formula (I) wherein —X—$R^2$ is an optionally substituted benzothiazole or benzoxazole, said compounds being represented by formula (I-d-1), in the presence of a suitable solvent such as, for example, acetic acid, at an elevated temperature, preferably at reflux temperature. It may be convenient to prepare compounds of formula (I-d-1) without isolating intermediates of formula (XX). Analogously, an intermediate of formula (XVIII) may be reacted with an intermediate of formula (XIX-b) to form an intermediate of formula (XXI) which is cyclized to a compound of formula (I) wherein —X—$R^2$ is an optionally 3-substituted 1,2,4-oxadiazole, said compounds being represented by formula (I-d-2), in a reaction-inert solvent such as, for example, toluene, at an elevated temperature, preferably at reflux temperature. Also analogously, an intermediate of formula (XVIII) may be reacted with an intermediate of formula (XIX-c) wherein Y is O, S or $NR^3$, to form an intermediate of formula (XXII) which is cyclized to a compound of formula (I) wherein —X—$R^2$ is an optionally substituted 1,2,4-triazole, 1,3,4-thiadiazole or 1,3,4-oxadiazole, said compounds being represented by formula (I-d-3), in a suitable solvent such as, for example, phosphorousoxychloride.

Also analogously, an intermediate of formula (XVIII) may be reacted with an intermediate of formula (XIX-d) wherein Y is O, S or $NR^3$, to form an intermediate of formula (XXIII) which is cyclized to a compound of formula (I) wherein —X—$R^2$ is an optionally amino substituted 1,2,4-triazole, 1,3,4-thiadiazole or 1,3,4-oxadiazole, said compounds being represented by formula (I-d-4) in a reaction-inert solvent such as, for example; toluene, and in the presence of an acid; or, which is cyclized to a compound of formula (I) wherein —X—$R^2$ is a disubstituted 1,3,4-triazole, said compounds being represented by formula (I-d-5).

The nitrile derivative of formula (XVI) may also be reacted with hydroxylamine hydrochloride or a functional derivative thereof, thus forming an intermediate of formula (XXIV) which may be reacted with an intermediate of formula (XXV) to form a compound of formula (I) wherein —X—$R^2$ is an optionally 5-substituted 1,2,4-triazole, 1,2, 4-thiadiazole or 1,2,4-oxadiazole, said compounds being represented by formula (I-d-6), in a reaction-inert solvent such as, for example, methanol, butanol or a mixture thereof, and in the presence of a base such as, for example, sodium methanolate.

Compounds of formula (I-d) wherein the heterocycle is substituted 2-thiazolyl, said compounds being represented by formula (I-d-7), can be prepared by reacting an intermediate of formula (XVI) with hydrogensulfide or a functional derivative thereof, in a reaction inert solvent such as, for example, pyridine, optionally in the presence of a suitable base such as, for example, triethylamine, thus forming an intermediate of formula (XXVI), which may subsequently be reacted with an intermediate of formula (XXVII) or a functional derivative thereof such as the ketal derivative thereof, in a reaction-inert solvent such as, for example, ethanol, and optionally in the presence of an acid such as, for example, hydrogenchloride.

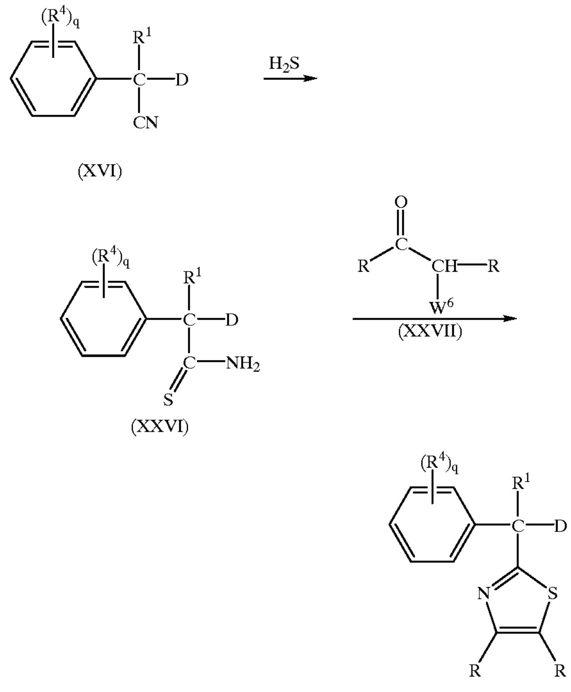

(XVI)

(XXVI)

(XXVII)

(I-d-7)

Compounds of formula (I-d) wherein the heterocycle is substituted 5-thiazolyl and $R^1$ is hydrogen, said compounds being represented by formula (I-d-8), can be prepared following the reaction procedure depicted in scheme 4.

Scheme 4

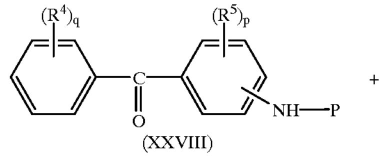
(XXVIII)

-continued

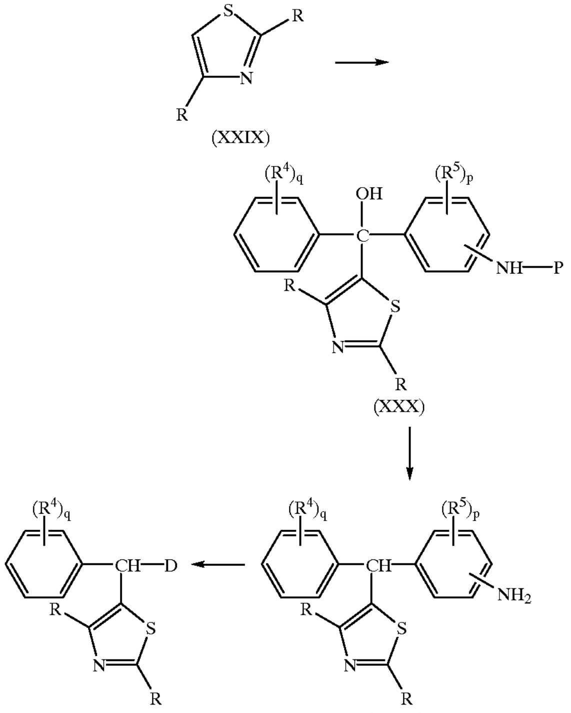
(XXIX)

(XXX)

(I-d-8)

(XXXI)

Initially, an intermediate of formula (XXVIII) wherein P is a protective group such as, for example, a $C_{1-6}$alkylcarbonyl group, is reacted with a thiazole derivative of formula (XXIX) in the presence of a suitable base such as, for example, butyl lithium, in a reaction inert solvent such as, for example, tetrahydrofuran, thus forming an intermediate of formula (XXX). It may be convenient to perform said reaction under an inert atmosphere at lower temperature, preferably at about −70° C. The hydroxy group and the protective group P of said intermediates (XXX) may be removed using art-known procedures such as, for example, stannous chloride and hydrochloric acid in acetic acid, thus forming an intermediate of formula (XXXI), of which the amino group may further be converted to a 6-azauracil moiety according to the procedure described in EP-A-0,170,316, thus forming a compound of formula (I-d-8).

Also, compounds of formula (I-d) wherein the heterocycle is 4-thiazolyl, said compounds being represented by formula (I-d-9), can be prepared following the reaction procedure depicted in scheme 5.

Scheme 5

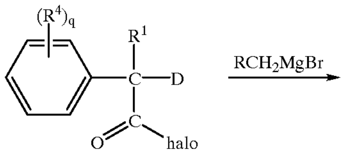

(XVIII)

-continued

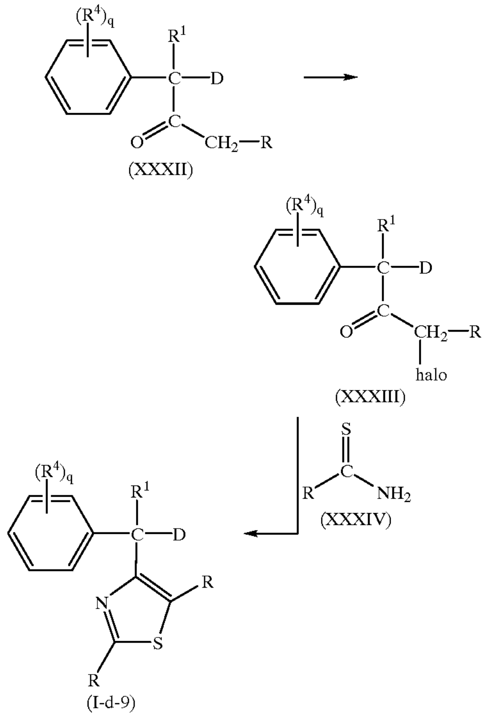

(XXXII)

(XXXIII)

(XXXIV)

(I-d-9)

An intermediate of formula (XVIII) is reacted with a Grignard reagent of formula $RCH_2MgBr$ or a functional derivative thereofto form an intermediate of formula (XXXII), which may be halogenated, preferably brominated, in the a-position using a suitable reagent such as trimethylphenylammonium tribromide in tetrahydrofuran, thus forming an intermediate of formula (XXXIII). Said intermediate (XXXIII) may then be reacted with a thioamide of formula (XXXIV) to form a compound of formula (I-d-9), in a reaction-inert solvent such as, for example, ethanol, at an elevated temperature, preferably reflux temperature.

The compounds of formula (I) can also be converted into each other following art-known procedures of functional group transformation of which some examples are mentioned hereinabove.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

IL-5, also known as eosinophil differentiating factor (EDF) or eosinophil colony stimulating factor (Eo-CSF), is a major survival and differentiation factor for eosinophils and therefore thought to be a key player in eosinophil infiltration into tissues. There is ample evidence that eosinophil influx is an important pathogenic event in bronchial asthma and allergic diseases such as, cheilitis, irritable bowel disease, eczema, urticaria, vasculitis, vulvitis, winterfeet, atopic dermatitis, pollinosis, allergic rhinitis and allergic conjunctivitis; and other inflammatory diseases, such as eosinophilic syndrome, allergic angiitis, eosinophilic fasciitis, eosinophilic pneumonia, PIE syndrome, idiopathic eosinophilia, eosinophilic myalgia, Crohn's disease, ulcerative colitis and the like diseases.

The present compounds also inhibit the production of other chemokines such as monocyte chemotactic protein-1 and -3 (MCP-1 and MCP-3). MCP-1 is known to attract both T-cells, in which IL-5 production mainly occurs, and monocytes, which are known to act synergetically with eosinophils (Carr et al., 1994, Immunology, 91, 3652–3656). MCP-3 also plays a primary role in allergic inflammation as it is known to mobilize and activate basophil and eosinophil leukocytes (Baggiolini et al., 1994, Immunology Today, 15(3), 127–133).

The present compounds have no or little effect on the production of other chemokines such as IL-1, IL-2, IL -3, IL-4, IL-6, IL-10, γ-interferon (IFN-γ) and granulocyte-macrophage colony stimulating factor (GM-CSF) indicating that the present IL-5 inhibitors do not act as broad-spectrum immunosuppressives.

The selective chemokine inhibitory effect of the present compounds can be demonstrated by in vitro chemokine measurements in human blood of which the test results for IL-5 are presented in the experimental part hereinafter. In vivo observations such as the inhibition of eosinophilia in mouse ear, the inhibition of blood eosinophilia in the Ascaris mouse model; the reduction of serum IL-5 protein production and splenic IL-5 mRNA expression induced by anti-CD3 antibody in mice and the inhibition of allergen- or Sephadex-induced pulmonary influx of eosinophils in guinea-pig are indicative for the usefulness of the present compounds in the treatment of eosinophil-dependent inflammatory diseases.

The present inhibitors of IL-5 production are orally active compounds.

In view of the above pharmacological properties, the compounds of formula (I) can be used as a medicine. In particular, the present compounds can be used in the manufacture of a medicament for treating eosinophil-dependent inflammatory diseases as mentioned hereinabove, more in particular bronchial asthma, atopic dertimatitis, allergic rhinitis and allergic conjunctivitis.

In view of the utility of the compounds of formula (I), there is provided a method of treating warm-blooded animals, including humans, suffering from eosinophil-dependent inflammatory diseases, in particular bronchial asthma, atopic dertimatitis, allergic rhinitis and allergic conjunctivitis. Said method comprises the systemic or topical administration of an effective amount of a compound of formula (I), a N-oxide form, a pharmaceutically acceptable addition salt or a possible stereoisomeric form thereof, to warm-blooded animals, including humans.

The present invention also provides compositions for treating eosinophil-dependent inflammatory diseases comprising a therapeutically effective amount of a compound of formula (I) and a pharmaceutically acceptable carrier or diluent.

To prepare the pharmaceutical compositions of this invention, a therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy-$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques, preferably, as measured by mass spectrometry, the M.S. ranges from 0.125 to 10.

The average substitution degree (D.S.) refers to the average number of substituted hydroxyls per anhydroglucose unit. The D.S. value can be determined by various analytical techniques, preferably, as measured by mass spectrometry, the D.S. ranges from 0.125 to 3.

Due to their high degree of selectivity as IL-5 inhibitors, the compounds of formula (I) as defined above, are also useful to mark or identify receptors. To this purpose, the compounds of the present invention need to be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}C$-atom or tritium atom.

One particular group consists of those compounds of formula (I) wherein $R^3$ and/or $R^4$ are a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $^{122}I$, $^{123}I$, $^{125}I$, $^{131}I$; radioactive bromides, e.g. $^{75}Br$, $^{76}Br$, $^{77}Br$ and $^{82}Br$, and radioactive fluorides, e.g. $^{18}F$. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}C$-atom or the substitution of a hydrogen atom by a tritium atom.

Hence, said radiolabelled compounds of formula (I) can be used in a process of specifically marking receptor sites in biological material. Said process comprises the steps of (a) radiolabelling a compound of formula (I), (b) administering this radio-labelled compound to biological material and subsequently (c) detecting the emissions from the radiolabelled compound. The term biological material is meant to comprise every kind of material which has a biological origin. More in particular this term refers to tissue samples, plasma or body fluids but also to animals, specially warm-blooded animals, or parts of animals such as organs.

The radiolabelled compounds of formula (I) are also useful as agents for screening whether a test compound has the ability to occupy or bind to a particular receptor site. The degree to which a test compound will displace a compound of formula (I) from such a particular receptor site will show the test compound ability as either an agonist, an antagonist or a mixed agonist/antagonist of said receptor.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PET) and the like. In this manner the distribution of the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

In general, it is contemplated that a therapeutically effective daily amount would be from 0.01 mg/kg to 50 mg/kg body weight, in particular from 0.05 mg/kg to 10 mg/kg body weight. A method of treatment may also include administering the active ingredient on a regimen of between two or four intakes per day.

Experimental Part

Hereinafter, the term 'RT' means room temperature, 'THF' means tetrahydrofuran, 'EtOAc' means ethylacetate, 'DMF' means N,N-dimethylformamide, 'MIK' means methylisobutyl ketone, 'DIPE' means diisopropylether, and 'HOAc' means acetic acid.

A. Preparation of the Intermediate Compounds

EXAMPLE A1 a) A solution of 4-chloro-3-(trifluoromethyl) benzeneacetonitrile (0.114 mol) in THF (100 ml) was added dropwise at RT to a solution of 1,2,3-trichloro-5-nitrobenzene (0.114 mol) and N,N,N-triethylbenzenemethanaminium chloride (3 g) in NaOH (150 ml) and THF (100 ml). The mixture was stirred for 2 hours, then poured out on ice, acidified with a concentrated HCl solution and extracted with $CH_2Cl_2$. The organic layer was separated, dried, filtered and the solvent was evaporated. The residue was crystallized from DIPE. The precipitate was filtered off and dried, yielding 40.4 g (86.5%) of (±)-2,6-dichloro-α-[4-chloro-3-(trifluoromethyl)phenyl]-4-nitrobenzene-acetonitrile (interm. 1).

b) A solution of intermediate (1) (0.0466 mol), iodomethane (0.0606 mol), KOH (0.1864 mol) and N,N,N-triethylbenzenemethanaminium chloride (0.0466 mol) in toluene (200 ml) was stirred at 50° C. for 2 hours. The mixture was poured out into water, acidified with HCl 3N and extracted with $CH_2Cl_2$. The organic layer was separated, dried, filtered and the solvent was evaporated. The residue was purified by column chromatography over silica gel (eluent: cyclohexane/EtOAc 90/10). The pure fractions were collected and the solvent was evaporated, yielding 11 g (55%) of (±)-2,6-dichloro-α-[4-chloro-3-(trifluoromethyl) phenyl]-α-methyl-4-nitrobenzene-acetonitrile (interm. 2).

c) A mixture of intermediate (2) (0.0259 mol) in methanol (200 ml) was hydrogenated at 40° C. overnight with platinum-on-charcoal catalyst 1% (1 g) as a catalyst in the presence of thiophene 10% in ethanol (1 ml). After uptake of hydrogen (3 equivalents), the catalyst was filtered through celite, washed with $CH_3OH$ and the filtrate was evaporated, yielding 10 g (98%) of (±)-4-amino-2,6-dichloro-α-[4-chloro-3-(trifluoromethyl)phenyl]-α-methylbenzeneacetonitrile (interm. 3).

EXAMPLE A2 a) A solution of $NaNO_2$ (0.0243 mol) in water (10 ml) was added dropwise at 5° C. to a solution of intermediate (3) (0.0243 mol) in HOAc (75 ml) and concentrated HCl (20 ml). The mixture was stirred at 0° C. for 35 minutes and then added dropwise to a solution of ethyl cyanoacetylcarbamoate (0.0326 mol) and sodium acetate (112 g) in water (1300 ml), cooled to 0° C. The mixture was stirred at 0° C. for 45 minutes. The precipitate was filtered off, washed with water and taken up in $CH_2Cl_2$. The organic layer was separated, washed with water, dried, filtered and the solvent was evaporated, yielding 15.2 g of (±)-ethyl 2-cyano-2-[[3,5-dichloro-4-[1-[4-chloro-3-(trifluoromethyl)phenyl]-1-cyanoethyl]phenyl]hydrozono]-1-oxoethylcarbamate (interm. 4).

b) A mixture of intermediate (4) (0.0271 mol) and potassiumacetate (0.0285 mol) in HOAc (150 ml) was stirred and refluxed for 3 hours and then poured out on ice. The precipitate was filtered off, washed with water and taken up in EtOAc. The organic layer was separated, washed with water, dried, filtered and the solvent was evaporated, yielding 12 g (86%) of (±)-2-[3,5-dichloro-4-[1-[4-chloro-3-(trifluoromethyl)phenyl]-1-cyanoethyl]phenyl]-2,3,4,5-tetrahydro-3,5-dioxo-1,2,4-triazine-6-carbonitrile (interm. 5).

c) A mixture of intermediate (5) (0.0223 mol) in HCl (40 ml) and HOAc (150 ml) was stirred and refluxed for 3 hours and then poured out into ice water. The precipitate was filtered off, taken up in $CH_2Cl_2$ and $CH_3OH$, washed with water, dried, filtered and the solvent was evaporated, yielding 11.4 g (96%) of (±)-2-[3,5-dichloro-4-[1-[4-chloro-3-(trifluoromethyl)phenyl]-1-cyanoethyl]phenyl]-2,3,4,5-tetrahydro-3,5-dioxo-1,2,4-triazine-6-carboxylic acid (interm. 6).

d) A mixture of intermediate (6) (0.05 mol) in 2-mercaptoacetic acid (60 ml) was stirred and refluxed for 140 minutes. The reaction mixture was allowed to cool to RT, then poured out into ice-water. The mixture was stirred, then decanted. $CH_2Cl_2/CH_3OH$ (300 ml, 90/10) was added to the residue. The organic layer was separated, washed with an aqueous $NaHCO_3$ solution (200 ml) and with water, then dried, filtered and the solvent was evaporated. The residue was purified over silica gel on a glass filter (eluent: $CH_2Cl_2/CH_3OH$ 99/1). The desired fractions were collected and the solvent was evaporated, yielding 28 g of (±)-2,6-dichloro-α-[4-chloro-3-(trifluoromethyl)phenyl]-4-(4,5-dihydro-3,5-dioxo-1,2,4-triazin-2(3H)-yl)-α-methylbenzeneacetonitrile (interm. 7). (±)-2-chloro-α-[4-chloro-3-(trifluoromethyl)phenyl]-4-(4,5-dihydro-3,5-dioxo-1,2,4-triazin-2(3H)-yl)-5,α-dimethylbenzeneacetonitrile was prepared following the same procedure as described in example A2d (interm. 8).

e) A mixture of intermediate (7) (0.0106 mol) and triethylamine (0.0106 mol) in pyridine (70 ml) was stirred at 60° C. Gaseous $H_2S$ was bubbled through the mixture for 8 hours. The mixture was stirred at 60° C. overnight. Gaseous $H_2S$ was bubbled through the mixture for another 10 hours. The mixture was stirred at 60° C. overnight. The solvent was evaporated. The residue was taken up in EtOAc, washed with a diluted HCl solution and with water, dried, filtered and the solvent was evaporated. The residue was purified by column chromatography over silica gel (eluent: $CH_2Cl_2/CH_3OH$ 98/2). The pure fractions were collected and the solvent was evaporated, yielding 2.5 g (45%) of (±)-2,6-dichloro-α-[4-chloro-3-(trifuoromethyl)phenyl]-4-(4,5-dihydro-3,5-dioxo-1,2,4-triazin-2(3H)-yl)-α-methylbenzeneethanethioamide (interm. 9).

Following the same procedure there were also prepared:

(±)-2-chloro-α-[4-chloro-3-(trifluoromethyl)phenyl]-4-[4,5-dihydro-3,5-dioxo-1,2,4-triazin-2(3H)-yl]-5,α-dimethylbenzeneethanethioamide (interm. 10);

(±)-2,6-dichloro-α-(3,4-dichlorophenyl)-4-(4,5-dihydro-3,5-dioxo-1,2,4-triazin-2(3H)-α-methylbenzeneethanethioamide (interm. 11);

(±)-2-chloro-α-[4-chloro-3-(trifluoromethyl)phenyl]-4-[4,5-dihydro-3,5-dioxo-1,2,4-triazin-2(3H)-yl]-α-methylbenzeneethanethioamide (interm. 12);

(±)-2-chloro-α-(4-chlorophenyl)-α-methyl-4-(4,5-dihydro-3,5-dioxo-1,2,4-triazin-2(3H)-yl) benzeneethanethioamide (interm. 13);

(±)-2,6-dichloro-α-(4-chlorophenyl)-4-(4,5-dihydro-3,5-dioxo-1,2,4-triazin-2(3H)-yl)-α-methylbenzeneethanethioamide (interm. 14);

(±)-2-chloro-α-(4-chlorophenyl)-4-(4,5-dihydro-3,5-dioxo-1,2,4-triazin-2(3H)-yl)benzeneethanethiomide (interm. 15).

EXAMPLE A3 a) A mixture of intermediate (1) (0.138 mol) in methanol (300 ml) was hydrogenated at RT under a 3 bar pressure for 1 hour with Raney Nickel (50 g) as a catalyst in the presence of thiophene solution 10% in ethanol (5 ml). After uptake of hydrogen (3 equivalents), the catalyst was filtered through celite, washed with methanol and $CH_2Cl_2$ and the filtrate was evaporated, yielding 49.5 g (94%) of (±)-4-amino-2,6-dichloro-α-[4-chloro-3-(trifluoromethyl)phenyl] benzeneacetonitrile (interm. 16).

b) (±)-2,6-dichloro-α-[4-chloro-3-(trifluoromethyl) phenyl]-4-(4,5-dihydro-3,5-dioxo-1,2,4-triazin-2(3H)-yl) benzeneethanethioamide was prepared following the same procedure as described in A1c and A2a through A2e (interm. 17).

c) Acetic anhydride (0.1268 mol) was added dropwise at RT to a solution of intermediate (16) (0.0634 mol) in toluene (200 ml). The mixture was stirred and refluxed for 3 hours, then cooled, poured out into $H_2O$ and extracted with EtOAc. The organic layer was separated, washed with $K_2CO_3$ 10% and with $H_2O$, dried, filtered and the solvent was evaporated, yielding 27.9 g (±)-N-[3,5-dichloro-4-[[4-chloro-3-(trifluoromethyl)phenyl]cyanomethyl]phenyl]acetamide (interm. 18; mp. 172° C.).

EXAMPLE A4 a) n-Butyllithium 1.6 M (0.135 mol) was added dropwise at −70° C. under $N_2$ flow to a solution of 3-bromopyridine (0.11 mol) in 1,1'-oxybisethane (250 ml). The mixture was stirred at −70° C. for 1 hour. A solution of 2,4'-dichloro-4-nitrodiphenylmethanone (0.0844 mol) in THF (200 ml) was added dropwise. The mixture was stirred at −70° C. for 3 hours, then poured out into water and extracted with EtOAc. The organic layer was separated, dried, filtered and the solvent was evaporated. The residue was purified by column chromatography over silica gel (eluent: cyclohexane/EtOAc 60/40 to 100/0). The pure fractions were collected and the solvent was evaporated, yielding 13.7 g (43%) of (±)-α-(2-chloro-4-nitrophenyl)-α-(4-chlorophenyl)-3-pyridinemethanol (interm. 19).

b) A mixture of intermediate (19) (0.0373 mol) in methanol (150 ml) was hydrogenated at RT under a 3 bar pressure for 4 hours with Raney Nickel (14 g) as a catalyst in the presence of thiophene solution 1% in ethanol (2.5 ml). After uptake of hydrogen (3 equivalents), the catalyst was filtered through celite and the filtrate was evaporated, yielding 12.06 g (94%) of (±)-α-(4-amino-2-chlorophenyl)-α-(4-chlorophenyl)-3-pyridinemethanol (interm. 20).

c) Formamide (60 ml) was added to a mixture of intermediate (20) (0.0349 mol) in HOAc (60 ml). The mixture was stirred at 150° C. for 6 hours, cooled, poured out into ice water, basified with $NH_4OH$ and extracted with $CH_2Cl_2$. The organic layer was separated, dried, filtered and the solvent was evaporated, yielding 14.1 g of (±)-N-[3-chloro-[4-[(4-chlorophenyl)-3-pyridinylmethyl]phenyl]formamide (interm. 21).

d) A mixture of intermediate (21) (0.0349 mol) in HCl 6N (150 ml) was stirred and refluxed for 4 hours, then cooled, poured out on ice, basified with $NH_4OH$ and extracted with $CH_2Cl_2$. The organic layer was separated, dried, filtered and the solvent was evaporated. The residue was purified by column chromatography over silica gel (eluent: $CH_2Cl_2/CH_3OH/NH_4OH$ 98.5/1.5/0.1). The pure fractions were collected and the solvent was evaporated, yielding 7.2 g (63%) of (±)-3-chloro-4-[(4-chlorophenyl)-3-pyridinylmethyl] benzenamine (interm. 22).

e) (±)-2-[3-chloro-4-[(4-chlorophenyl)-3-pyridinylmethyl]phenyl]-2,3,4,5-tetrahydro-3,5-dioxo-1,2,4-triazine-6-carboxylic acid was prepared following the same procedure as decribed in A1c and A2a through A2c (interm. 23).

EXAMPLE A5 a) A mixture of (±)-α-(2-chloro-4-nitrophenyl)-α-(4-chlorophenyl)-1-methyl-1H-imidazole-2-methanol (0.0397 mol) and $SnCl_2$ (0.2382 mol) in HOAc (150 ml) and HCl (150 ml) was stirred and refluxed for 2 hours, then cooled, poured out on ice, basified with $NH_4OH$, filtered over celite and extracted with $CH_2Cl_2$ and $CH_3OH$. The organic layer was separated, dried, filtered and the solvent was evaporated, yielding 12 g (91%) of (±)-3-chloro-4-[(4-chlorophenyl)(1-methyl-1H-imidazol-2-yl)methyl]benzenamine (interm. 24).

b) (±)-2-[3-chloro-4-[(4-chlorophenyl)(1-methyl-1H-imidazol-2-yl)methyl]phenyl]-2,3,4,5-tetrahydro-3,5-dioxo-1,2,4-triazine-6-carboxylic acid (interm. 25); (±)-2-[3-chloro-4-[(4-chlorophenyl)(1-methyl-1H-1,2,4-triazol-5-yl)methyl]phenyl]-2,3,4,5-tetrahydro-3,5-dioxo-1,2,4-triazine-6-carboxylic acid (interm. 26); and (±)-2-[3-chloro[(4-chlorophenyl)(2-methyl-4-phenyl-5-thiazolyl)methyl]phenyl]-2,3,4,5-tetrahydro-3,5-dioxo-1,2,4-triazine-6-carboxylic acid (interm. 27) were prepared following the same procedure as decribed in A1c and A2a through A2c.

EXAMPLE A6 a) α-(4-chlorophenyl)-4-pyridinemethanol (0.0512 mol), N-(3,5-dichlorophenyl)-acetamide (0.102 mol) and polyphosphoric acid (210 g) were stirred at 140° C. for 90 minutes. The mixture was cooled to 100° C., poured out into ice water, basified with $NH_4OH$ and extracted with $CH_2Cl_2$. The organic layer was separated, dried, filtered and the solvent was evaporated. The residue was taken up in 2-propanone and diethyl ether. The precipitate was filtered off and the filtrate was evaporated. The residue was purified by column chromatography over silica gel (eluent: $CH_2Cl_2$/$CH_3OH$/$NH_4OH$ 97.5/2.5/0.1). The pure fraction was collected and the solvent was evaporated, yielding 17.94 g (87%) of (±)-N-[3,5-dichloro-4-[(4-chlorophenyl)-4-pyridinylmethyl]phenyl]-acetamide (interm. 28).

b) The following products were prepared as described in A4c through A4e:

(±)-2-[3,5-dichloro-4-[(4-chlorophenyl)-4-pyridinylmethyl]phenyl]-2,3,4,5-tetrahydro-3,5-dioxo-1,2,4-triazine-6-carboxylic acid (interm. 29);

(±)-2-[3,5-dichloro-4-[(4-chlorophenyl)-2-pyridinylmethyl]phenyl]-2,3,4,5-tetrahydro-3,5-dioxo-1,2,4-triazine-6-carboxylic acid (interm. 30);

(±)-2-[3-chloro-4-[(2-chlorophenyl)-2-pyridinylmethyl]phenyl]-2,3,4,5-tetrahydro-3,5-dioxo-1,2,4-triazine-6-carboxylic acid (interm. 31);

(±)-2-[3,5-dichloro-4-[(4-chlorophenyl)(1-methyl-1H-imidazol-2-yl)methyl]phenyl]-2,3,4,5-tetrahydro-3,5-dioxo-1,2,4-triazine-6-carboxylic acid (interm. 32); and (±)-2-[3,5-dichloro-4-[(4-chlorophenyl)-3-pyridinylmethyl]phenyl]-2,3,4,5-tetrahydro-3,5-dioxo-1,2,4-triazine-6-carboxylic acid (interm. 33).

EXAMPLE A7 a) A mixture of 4-isothiocyanato-2-(trifluoromethyl)-α-[3-(trifluoromethyl)phenyl]-benzeneacetonitrile (0.0516 mol), NaOH solution, 50% (0.155 mol) and N,N,N-triethylbenzenemethanaminium chloride (0.0052 mol) in toluene (250 ml) was stirred for 4 hours under $O_2$ at RT. Ice-water and HOAc (9.3 ml) were added. Toluene was added and the reaction mixture was stirred vigorously. The layers were separated. The separated organic layer was dried, filtered and the solvent evaporated. The residue was stirred in hexane. The precipitate was filtered off, washed, and dried, yielding 15.8 g (97.2%) of (amino-2-chlorophenyl)[4-chloro-3-(trifluoromethyl)phenyl]methanone (interm. 34).

b) (±)-2-[3-chloro-4-[4-chloro-3-(trifluoromethyl)benzoyl]phenyl]-1,2,4-triazine-3,5(2H,4H)-dione (interm. 35) was prepared following the procedures described in A1c and A2a through A2d.

c) A mixture of intermediate (35) (0.013 mol) in methanol (50 ml) and THF (50 ml) was stirred at RT. $NaBH_4$ (0.013 mol) was added portionwise. The reaction mixture was stirred for 1 hour, then acidified (to pH=±6) with concentrated hydrochloric acid. The solvent was evaporated. The residue was purified by column chromatography over silica gel (eluent: $CH_2Cl_2$/$CH_3OH$ 95/5). The desired fractions were collected and the solvent was evaporated, yielding 5.3 g (94.2%) of (±)-2-[3-chloro-4-[[4-chloro-3-(trifluoromethyl)phenyl]hydroxymethyl]phenyl-1,2,4-triazine-3,5(2H,4H)-dione (intern. 36). In a similar way, there was also prepared 2-[3,5-dichloro-4-[(4-fluorophenyl)hydroxymethyl]phenyl-1,2,4-triazine-3,5(2H,4H)-dione (interm. 37).

d) Thionylchloride (5 ml) was added dropwise to a mixture of intermediate (30) (0.012 mol) in $CH_2Cl_2$ (50 ml), stirred at RT. The resulting reaction mixture was stirred and refluxed for 2 hours. The solvent was evaporated. Toluene was added and azeotroped on the rotary evaporator, yielding 4.9 g (90.4%) of (±)-2-[3-chloro-4-[chloro[4-chloro-3-(trifluoromethyl)phenyl]methyl]phenyl]-1,2,4-triazine-3,5(2H,4H)-dione (interm. 38).

Following the same procedure, there were also prepared:

2-[3,5-dichloro-4-[chloro[4-chloro-3-(trifluoromethyl)phenyl]methyl]phenyl]-1,2,4-triazine-3,5(2H,4H)-dione (interim. 39);

(±)-2-[3-chloro-4-[chloro(4-chlorophenyl)-2-thiazolylmethyl]phenyl]-1,2,4-triazine-3,5(2H,4H)-dione (interm. 40); and (±)-2-[4-[(2-benzothiazolyl)chloro(4-chlorophenyl)methyl-3-chlorophenyl]-1,2,4-triazine-3,5(2H,4H)-dione (interm. 41).

EXAMPLE A8 a) $K_2CO_3$ (0.1786 mol) was added to a solution of intermediate (18) (0.0638 mol) in dimethylsulfoxide (100 ml) and water (10 ml). Air was bubbled through the mixture for 72 hours. The mixture was poured out into $H_2O$. The precipitate was filtered off and taken up in EtOAc. The organic solution was washed with $H_2O$, dried, filtered and the solvent was evaporated. The residue was purified by column chromatography over silica gel (eluent: $CH_2Cl_2$/$CH_3OH$ 99.25/0.75). The pure fractions were collected and the solvent was evaporated, yielding 18.6 g (72%) of N-[3,5-dichloro-4-[4-chloro-3-(trifluoromethyl)benzoyl]phenyl]acetamide (interm. 42).

b) 2-[3,5-dichloro-4-[4-chloro-3-(trifluoromethyl)benzoyl]phenyl]-2,3,4,5-tetrahydro-3,5-dioxo-1,2,4-triazine-6-carboxylic acid (interm. 43) was prepared following the procedure as described in A6b.

c) 2-[3,5-dichloro-4-[4-chloro-3-(trifluoromethyl)benzoyl]phenyl]-1,2,4-triazine-3,5(2H,4H)-dione (interm. 44) was prepared following the procedure as described in A2d.

d) 2-[3,5-dichloro-4-[[4-chloro-3-(trifluoromethyl) phenyl]hydroxymethyl]phenyl]-1,2,4-triazine-3,5(2H,4H)-dione (interm. 45) was prepared following the procedure as described in A7c.

EXAMPLE A9 a) A mixture of 4-chloro-α-[2-chloro-4-(4,5-dihydro-3,5-dioxo-1,2,4-triazin-2(3H)-yl)phenyl]-α-methyl-3-(trifluoromethyl)benzeneacetonitrile (0.009 mol) in $H_2SO_4$ (50 ml), HOAc (50 ml) and $H_2O$ (40 ml) was stirred and refluxed overnight. The mixture was poured out into ice water and extracted with EtOAc. The organic layer was separated, washed with $H_2O$, dried, filtered and the solvent was evaporated, yielding 4.2 g of (±)-2-chloro-α-[4-chloro-3-(trifluoromethyl)phenyl]-4-[4,5-dihydro-3,5-dioxo-1,2,4-triazin-2(3H)-yl]-α-methylbenzeneacetic acid (interm. 46).

b) A mixture of intermediate (46) (0.009 mol) in thionyl chloride (25 ml) was stirred and refluxed for 2.5 hours. The solvent was evaporated, yielding (±)-2-chloro-α-[4-chloro-3-(trifluoromethyl)phenyl]-4-[4,5-dihydro-3,5-dioxo-1,2,4-triazin-2(3H)-yl]-α-methylbenzeneacetyl chloride (interm. 47).

Following the same procedure, there were also prepared:

(±)-2-chloro-α-(4-chlorophenyl)-4-(4,5-dihydro-3,5-dioxo-1,2,4-triazin-2(3H)-yl)benzeneacetyl chloride (interm. 48); and (±)-2-chloro-α-(4-chlorophenyl)-4-(4,5-dihydro-3,5-dioxo-1,2,4-triazin-2(3H)-yl)-α-methylbenzeneacetyl chloride (interm. 49).

c) A solution of intermediate (48) (0.011 mol) in 2-propanone (25 ml) was added at RT to a solution of N-hydroxy benzenecarboximidamide (0.011 mol) and $K_2CO_3$ (0.011 mol) in 2-propanone (25 ml). The mixture was stirred at RT overnight. The precipitate was filtered off, washed with water and taken up in $CH_2Cl_2$. The organic layer was separated, dried, filtered and the solvent was evaporated, yielding 1.4 g (25%) of (±)-(iminophenylmethyl)amino 2-chloro-4-(4,5-dihydro-3,5-dioxo-1,2,4-triazin-2(3H)-yl)-α-(4-chlorophenyl) benzeneacetate (interm. 50).

Following the same procedure, there was also prepared:

(±)-(iminophenylmethyl)amino 2-chloro-α-(4-chlorophenyl)-4-(4,5-dihydro-3,5-dioxo-1,2,4-triazin-2(3H)-yl)-α-methylbenzeneacetate (ester) (interm. 51).

d) A solution of intermediate (48) (0.0365 mol) in $CH_2Cl_2$ (70 ml) was added at RT to a solution of 2-aminophenol (0.073 mol) in $CH_2Cl_2$ (280 ml). The mixture was stirred at RT for 12 hours, then washed with HCl 3N and with $H_2O$, dried, filtered and the solvent was evaporated. The residue was purified by column chromatography over silica gel (eluent: $CH_2Cl_2$/$CH_3OH$ 98/2). The pure fractions were collected and the solvent was evaporated, yielding 3.8 g (21%) of (±)-α-(4-chlorophenyl)-3-chloro-4-(4,5-dihydro-3,5-dioxo-1,2,4-triazin-2(3H)-yl)-N-(2-hydroxyphenyl) benzeneacetamide (interm. 52).

In a similar manner there were also prepared:

(±)-2-chloro-α-(4-chlorophenyl)-4-(4,5-dihydro-3,5-dioxo-1,2,4-triazin-2(3H)-yl)benzeneacetic acid 2-benzoylhydrazide (interm. 53);

(±)-(benzoylamino)-2,6-dichloro-α-(4-chlorophenyl)-4-(4,5-dihydro-3,5-dioxo-1,2,4-triazine-2(3H)-yl) benzeneacetamide (interm. 54);

(±)-2-chloro-α-[4-chloro-3-(trifluoromethyl)phenyl]-4(4,5-dihydro-3,5-dioxo-1,2,4-triazine-2(3H)-yl)-α-methylbenzeneacetic acid 2-benzoylhydrazide (interm. 55);

(±)-2-chloro-α-(4-chlorophenyl)-4-(4,5-dihydro-3,5-dioxo-1,2,4-triazin-2(3H)-yl)-N-(2-hydroxyphenyl)-α-methylbenzeneacetonitrile (interm. 56);

(±)-2-chloro-α-(4-chlorophenyl)-4-(4,5-dihydro-3,5-dioxo-1,2,4-triazin-2(3H)-yl)benzeneacetic acid 2-acetylhydrazide (interm. 57);

(±)-2-chloro-α-(4-chlorophenyl)-4-(4,5-dihydro-3,5-dioxo-1,2,4-triazin-2(3H)-yl)-N-(2-phenyl-2-oxoethyl) benzeneacetamide (interm. 58);

(±)-2-[[2-chloro-4-(4,5-dihydro-3,5-dioxo-1,2,4-triazin-3(2H)-yl)phenyl](4-chlorophenyl)acetyl]-N-phenylhydrazinecarbothiomide (interm. 59);

(±)-2-chloro-α-(4-chlorophenyl)-4-(4,5-dihydro-3,5-dioxo-1,2,4-triazin-2(3H)-yl)-αmethylbenzeneacetic acid 2-benzoylhydrazide (interm. 60); and (±)-2,6-dichloro-α-(4-chlorophenyl)-4-(4,5-dihydro-3,5-dioxo-1,2,4,-triazin-2(3H)-yl)-N-(2-phenyl-2-oxoethyl) benzeneacetamide (interm. 61).

EXAMPLE A10 a) A mixture of 2-[3-chloro-4-[chloro(4-chlorophenyl) methyl]phenyl]-1,2,4-triazine-3,5-(2H,4H)-dione (0.03 mol), thiourea (0.03 mol) and $NaHCO_3$ (0.03 mol) in DMF (75 ml) was stirred for 18 hours at RT. The solvent was evaporated. The residue was stirred in water, filtered off, washed with water, yielding 12.3 g. (±)-[2-chloro-4-(4,5-dihydro-3,5-dioxo-1,2,4-triazin-2(3H)-yl)phenyl]-4-(chloro-phenyl)methyl carbamimidothioate (interm. 62).

b) A mixture of NaOH (0.25 mol) in water (100 ml) was stirred at RT. (0.03 mol) was added and the resulting reaction mixture was stirred for 18 hours at RT, neutralized, and the precipitate was filtered off and dissolved in $CH_2Cl_2$. The aqueous phase was separated. The separated organic layer was dried, filtered, and the solvent evaporated. The residue was purified over silica gel on a glass filter (eluent. $CH_2Cl_2$/$CH_3OH$/THF 92/3/5). The desired fractions were collected and the solvent was evaporated. The residue was purified by column chromatography over silica gel (eluent: $CH_2C_2$/$CH_3OH$/THF 92/3/5). The pure fractions were collected and the solvent was evaporated. The residue was stirred in DIPE, filtered off and dried, yielding 4.2 g (37%) (±)-2-[3-chloro-4-[(4-chlorophenyl)mercaptomethyl]phenyl]-1,2,4-triazine-3,5(2H,4H)-dione (interm. 63).

EXAMPLE A11 a) A mixture of 2-[3-chloro-4-(4-chlorobenzoyl)phenyl]-1,2,4-triazine-3,5(2H,4H)-dione (0.081 mol) in formic acid (120 ml) and formamide (300 ml) was stirred for 16 hours at 160° C. The reaction mixture was cooled, poured out into water (600 ml) and the resulting precipitate was filtered off and dried. This fraction was purified by column chromatography over silica gel (eluent: $CH_2Cl_2$/$CH_3OH$ 95/5). The pure fractions were collected and the solvent was evaporated. The residue was stirred in DIPE, filtered off, and dried, yielding 8.78 g (22.5%) of (±)-N-[[2-chloro-4-(4,5-dihydro-3,5-dioxo-1,2,4-triazin-2(3H)-yl)phenyl](4-chlorophenyl) methyl]formamide (interm. 64).

b) A mixture of intermediate (64) (0.277 mol) in HCl (200 ml, 36%) and HOAc (1000 ml) was stirred and refluxed for 1 hour. The solvent was evaporated. The residue was taken up into water, then basified with $K_2CO_3$. The precipitate was filtered off, dried and stirred in boiling ethanol, cooled, filtered off and dried. The precipitate was purified by column chromatography over silica gel (eluent: $CH_2Cl_2$/$CH_3OH$ 95/5). The pure fractions were collected and the solvent was evaporated. The residue was stirred in boiling $CH_3CN$, then cooled, filtered off and dried, yielding 1.1 g (±)-2-[4-[amino (4-chlorophenyl)methyl]-3-chlorophenyl]-1,2,4-triazine-3,5 (2H,4H)-dione (interm. 65).

EXAMPLE A12

$NaOCH_3$ (0.189 mol; 30% in $CH_3OH$) was added to a solution of hydroxylamine (0.189 mol) in ethanol (105 ml) The mixture was stirred at RT for 15 minutes and then filtered. The filtrate was added to a mixture of 2-chloro-α-(4-chlorophenyl)-4-(4,5-dihydro-3,5-dioxo-1,2,4-triazin-2-(3H)-yl)benzeneacetonitrile (0.054 mol) in ethanol (55 ml). The mixture was stirred at 60° C. for 1 hour, stirred and refluxed for 2 hours and stirred at RT overnight. The solvent was evaporated. The residue was taken up in water and extracted with EtOAc. The organic layer was separated, dried, filtered and the solvent was evaporated, yielding 20.3 g of (±)-2-chloro-α-(4-chlorophenyl)-4-(4,5-dihydro-3,5-dioxo-1,2,4-triazin-2(3H)-yl)-N'-hydroxybenzeneethanimidamide (interm. 66).

EXAMPLE A13 a) Trifluoro acetic acid (100 ml), previously cooled to 5° C., was added dropwise at 0° C./5° C. under $N_2$ flow to (±)-1,1-dimethylethyl-2-[2-[2,6-dichloro-4-(4,5-dihydro-3,5-dioxo-1,2,4-triazin-2(3H)-yl)phenyl]-2-(4-chlorophenyl)acetyl]hydrazinecarboxylate (0.035 mol). The mixture was allowed to warm to RT and then stirred for 1 hour. The solvent was evaporated. The residue was taken up in $H_2O$. The precipitate was filtered off, dried, washed with DIPE and dried, yielding 11 g (70%) of R142321 (interm. 67).

b) A mixture of 3-hydroxy-benzoyl chloride (0.0124 mol) in THF (25 ml) was added dropwise at 10° C. under $N_2$ flow to a solution of intermediate 67 (0.0113 mol) and triethylamine (0.0452 mol) in THF (30 ml). The mixture was brought to RT. HCl 3N was added and the mixture was extracted with $CH_2Cl_2$. The organic layer was separated, dried, filtered and the solvent was evaporated. The residue was taken up in ethanol. The mixture was filtered and the filtrate was evaporated. The residue was purified by column chromatography over silica gel (eluent $CH_2Cl_2/CH_3OH$ 95/5). The pure fractions were collected and the solvent was evaporated, yielding 3 g (47%) of (±)-2-[3,5-dichloro-4-[1-(4-chlorophenyl)-2-[(3-hydroxybenzoyl)hydrazino]-2-oxoethyl]phenyl]-1,2,4-triazine-3,5(2H,4H)-dione (interm. 68)

EXAMPLE A14 a) A mixture of 2,6-dichloro-α-(4-chlorophenyl)-4-(4,5-dihydro-3,5-dioxo-1,2,4,-triazin-2(3H)-yl)-benzeneacetyl chloride (0.05 mol) in THF (200 ml) was stirred at −75° C. A solution of chloroethyl magnesium (0.1 mol; 2 M/THF) in THF (50 ml) was added dropwise at −75° C. The reaction mixture was stirred for 90 minutes, then the temperature was raised to −20° C. A saturated aqueous $NH_4Cl$ solution was added dropwise. Water was added and the product was extracted with $CH_2Cl_2$. The organic layer was separated, dried, filtered and the solvent was evaporated. The residue was filtered over silica gel (eluent: $CH_2Cl_2/CH_3OH$ 98/2). Two fractions were collected and the solvent was evaporated, yielding 3.8 g (±)-2-[3,5-dichloro-4-[1-(4-chlorophenyl)-2-oxobutyl]phenyl]-1,2,4-triazine-3,5(2H,4H)-dione (interm. 69).

b) A mixture of intermediate 69 (0.005 mol) in 1,4-dioxane (10 ml) and diethyl ether (20 ml) was stirred at RT. $Br_2$ (0.005 mol) was added dropwise at RT and the resulting reaction mixture was stirred for 15 hours at RT. This mixture was washed 3 times with water and $CH_2Cl_2$ was added. The separated organic layer was dried, filtered and the solvent evaporated. The residue was dried, yielding 2.6 g (±)-2-[4-[3-bromo-1-(4-chlorophenyl)-2-oxobutyl]-3,5-dichlorophenyl]-1,2,4-triazine-3,5(2H,4H)-dione (interm. 70).

EXAMPLE A15 a) n-Butyl lithium (0.045 mol) was added at −70° C. under $N_2$ flow to a solution of 4-phenyl-thiazole (0.045 mol) in diethyl ether (50 ml). The mixture was stirred at −70° C. for 90 minutes. A solution of 2-[3-chloro-4-(4-chlorobenzoyl)phenyl]-1,2,4-triazine-3,5-(2H,4H)-dione (0.015 mol) in THF (10 ml) was added at −70° C. The mixture was stirred at −70° C. for 1 hour, then poured out into ice water, neutralized with HCl 3N and extracted with EtOAc. The organic layer was separated, dried, filtered and the solvent was evaporated. The residue was purified by column chromatography oversilica gel (eluent: $CH_2Cl_2/CH_3OH$ 98/2). The desired fraction was repurified by HPLC (eluent: $CH_3OH/(NH_4OAc$ 1% in $H_2O)$ 80/20). The pure fractions were collected and the solvent was evaporated, yielding 0.83 g (11%) of (±)-2-[3-chloro-4-[(4-chlorophenyl)hydroxy(4-phenyl-2-thiazolyl)methyl]phenyl]-1,2,4-triazine-3,5(2H, 4H)-dione (interm. 71).

b) A mixture of intermediate 71 (0.0076 mol) in thionyl chloride (35 ml) was stirred at 50° C. for 4 hours and then brought to RT. The solvent was evaporated, yielding (±)-2-[3-chloro-4-[chloro(4-chlorophenyl)(5-chloro-4-phenyl-2-thiazolyl)methyl]-phenyl]-1,2,4-triazine-3,5(2H,4H)-dione (interm. 72).

EXAMPLE A16 a) 1-Chloromethoxy-2-methoxy-ethane (0.147 mol) was added dropwise at 15° C. to a solution of 3-(3-methoxyphenyl)-8-methyl-8-azabicyclo[3.2.1]octan-3-ol (0.134 mol) and $K_2CO_3$ (0.134 mol) in DMF (200 ml). The mixture was stirred at RT for 24 hours, then poured out into $H_2O$ and extracted with diethyl ether. The organic layer was separated, washed with $H_2O$, dried, filtered and the solvent was evaporated, yielding 67.27 g (±)-2-chloro-α-(4-chlorophenyl)-4-[4,5-dihydro-4-[(2-methoxyethoxy)methyl]-3,5-dioxo-1,2,4-triazin-2(3H)-yl]benzeneacetonitrile (interm. 73).

b) NaH (0.063 mol) was added at 10° C. under $N_2$ flow to a solution of intermediate 73 (0.0485 mol) in DMF (100 ml). The mixture was stirred for 30 minutes. A solution of 2-chloromethyl-4-phenyl-thiazole (0.063 mol) in DMF (100 ml) was added. The mixture was allowed to warm to 15° C. over a 2-hour period while stirring, then poured out into ice water and extracted with diethyl ether. The organic layer was separated, washed with $H_2O$, dried, filtered and the solvent was evaporated. The residue was purified by column chromatography over silica gel (eluent: cyclohexane/EtOAc 65/35). The pure fractions were collected and the solvent was evaporated, yielding 15 g (52%) of (±)-α-[2-chloro-4-[4,5-dihydro-4-[(2-methoxyethoxy)methyl]-3,5-dioxo-1,2,4-triazin-2(3H)-yl]phenyl]-α-(4-chlorophenyl)-4-phenyl-2-thiazolpropanenitrile (interm. 74)

c) A mixture of intermediate 74 (0.0186 mol) in $H_2SO_4$ (160 ml), acetic acid (160 ml) and $H_2O$ (25 ml) was stirred and heated for 48 hours. The mixture was cooled and poured out into $H_2O$. The precipitate was filtered off, taken up in EtOAc and the mixture was separated into its layers. The organic layer was dried, filtered and the solvent was evaporated, to give residue 1. The aqueous layer was evaporated partially and then cooled. The precipitate was filtered off and taken up in EtOAc. The organic solution was dried, filtered and the solvent was evaporated, to give residue 2.

Residue 1 and 2 were combined, yielding 8.97 g (86%) of (±)-α-[2-chloro-4-[4,5-dihydro-3,5-dioxo-1,2,4-triazin-2(3H)-yl]phenyl]-α-(4-chlorophenyl)-4-phenyl-2-thiazolpropanoic acid (interm. 75).

EXAMPLE A17 a) NaH (0.0772 mol) was added portionwise at 0° C. under $N_2$ flow to a mixture of 4-chloro-benzeneacetonitrile (0.0643 mol) in DMF (50 ml). The mixture was stirred at 0° C. under $N_2$ flow for 1 hour. A mixture of 1,3-dibromo-2-methoxy-5-nitro-benzene (0.0643 mol) in DMF (50 ml) was added at 0° C. under $N_2$ flow. The mixture was stirred at RT for 3 hours, hydrolized with $H_2O$ and HCl 3N and extracted with EtOAc. The organic layer was separated, dried, filtered and the solvent was evaporated. The residue was purified by column chromatography over silica gel (eluent: $CH_2Cl_2$/cyclohexane 60/40). The pure fractions were collected and the solvent was evaporated, yielding 12.8 g (46%) of (±)-2,6-dibromo-α-(4-chlorophenyl)-4-nitrobenzeneacetonitrile (interm. 76).

b) $TiCl_3$ (0.13 mol; 15% in $H_2O$) was added dropwise at RT to a solution of intermediate 76 (0.026 mol) in THF (200 ml). The mixture was stirred at RT for 2 hours, poured out into $H_2O$ and extracted with $CH_2Cl_2$. The organic layer was separated, washed with $H_2O$ and with $K_2CO_3$ 10%, dried, filtered and the solvent was evaporated. 2 g of this fraction was crystallized from diethyl ether. The precipitate was filtered off and dried, yielding 1.3 g (±)-4-amino-2,6-dibromo-α-(4-chlorophenyl)-benzeneacetonitrile (interm. 77).

B. Preparation of the Final Compounds

EXAMPLE B1

A mixture of 2-[3-chloro-4-[chloro(4-chlorophenyl)methyl]phenyl]-1,2,4-triazine-3,5(2H,4H)-dione (0.0075 mol) and 1,8-diazabicyclo[5.4.0]undec-7-ene (0.025 mol) in 2-methylpropanol (25 ml) was stirred for 72 hours at 80° C. The solvent was evaporated. The residue was purified by column chromatography over silica gel (eluent: $CH_2Cl_2$/$CH_3OH$ 97.5/2.5). The pure fractions were collected and the solvent was evaporated. The residue was dried, yielding 0.8 g (25%) of (±)-2-[3-chloro-4-[(4-chloro-phenyl)(2-methylpropoxy)methyl]phenyl]-1,2,4-triazine-3,5(2H,4H)-dione (compound 133).

EXAMPLE B2 a) A mixture of 2-[3-chloro-4-[chloro(4-chlorophenyl)methyl]phenyl]-1,2,4-triazine-3,5(2H,4H)-dione (0.015 mol) and 2-mercaptopyridine (0.04 mol) in THF (100 ml) was stirred overnight at RT. 1,8-diazabicyclo[5.4.0]undec-7-ene (0.03 mol) was added and the resulting reaction mixture was stirred for 3 hours. NaOH (1 N; 50 ml) was added. The mixture was stirred for 5 minutes, then extracted with EtOAc. The separated organic layer was washed with water, dried, filtered and the solvent evaporated. The aqueous layers were combined, then acidified (pH=6) with HCl (1 N). This mixture was extracted with $CH_2Cl_2$. The separated organic layer was dried, filtered, and the solvent was evaporated. The residue was purified by column chromatography over silica gel (eluent: $CH_2Cl_2$/THF/$CH_3OH$ 94/5/1). The pure fractions were collected and the solvent was evaporated. The residue was stirred overnight in diethyl ether. The solvent was evaporated. The residue was dried, yielding 2.98 g (43%) (±)-2-[3-chloro-4-[(4-chlorophenyl)(2-pyridinyl-thio)methyl]phenyl]-1,2,4-triazine-3,5(2H,4H)-dione (compound 93).

b) (±)-2-[3-chloro-4-[(4-chlorophenyl)(1H-imidazol-2-ylthio)methyl]phenyl]-1,2,4-triazine-3,5(2H,4H)-dione was prepared using the same procedure as in example B2a, but using $NaHCO_3$ as a base and DMF as a solvent (compound 94).

c) Sodium (0.075 mol) was added portionwise to ethanol (50 ml) under $N_2$ atmosphere and this mixture was stirred until complete dissolution. Ethyl 2-amino-3-mercaptopropanoate (0.075 mol) was added and the mixture was stirred for 2 hours at RT. The solvent was evaporated, THF (50 ml) was added to the residue, and a solution of 2-[3-chloro-4-[chloro(4-chlorophenyl)methyl]phenyl]-1,2,4-triazine-3,5(2H,4H)-dione (0.015 mol) in THF (50 ml) was added. 1,8-diazabicyclo[5.4.0]undec-7-ene (0.03 mol) was added and the resulting reaction mixture was stirred overnight at RT. The solvent was evaporated. The residue was stirred in water and extracted with $CH_2Cl_2$. The organic layer was separated, washed with water, dried, filtered and the solvent was evaporated. This fraction was purified by HPLC over silica gel (eluent: $CH_2Cl_2$/$CH_2OH$ 97/3). The pure fractions were collected and the solvent was evaporated. The residue was stirred in DIPE, filtered off, washed and dried, yielding (±)-ethyl α-[[[(4-chlorophenyl)[2-chloro-4-(4,5-dihydro-3,5-dioxo-1,2,4-triazin-2(3H)-yl)phenyl]methyl]thio]methyl]glycine (compound 95).

d) A mixture of intermediate 39 (0.00618 mol), 5-amino-4-phenyl-2(3H)-thiazole-thione (0.00742 mol) and 2,3,4,6,7,8,9,10-octahydropyrimido[1,2-a]azepine (0.0124 mol) in dry THF (50 ml) and DMF (50 ml) was stirred and refluxed for four days under $N_2$ atmosphere. The solvent was evaporated. The residue was taken up into $CH_2Cl_2$/$CH_3OH$ (95/5). The organic solution was washed twice with a saturated aqueous NaCl solution, dried, filtered and the solvent was evaporated. The residue was purified by flash column chromatography over silica gel (eluent: $CH_2Cl_2$/$CH_3OH$ 97.5/2.5). The desired fractions were collected and the solvent was evaporated. The residue was repurified by HPLC over silica gel (eluent: $CH_2Cl_2$/$CH_3OH$ 100/0 first 30 minutes, then 95/5). The pure fractions were collected and the solvent was evaporated. The residue was stirred in boiling $CH_3CN$, then allowed to cool to RT. The precipitate was filtered off, washed with $CH_3CN$, then dried, yielding 0.24 g of (±)-2-[3,5-dichloro-4-[[4-chloro-3-(trifluoromethyl)phenyl][(2,3-dihydro-5-phenyl-2-thioxo-1H-imidazol-4-yl)thio]-methyl]phenyl]-1,2,4-triazine-3,5(2H,4H)-dione (comp. 400).

EXAMPLE B3 a) A mixture of 2-[3-chloro-4-[chloro(4-chlorophenyl)methyl]phenyl]-1,2,4-triazine-3,5(2H,4H)-dione (0.015 mol) and 1-methylpiperazine (0.04 mol) in DMF (100 ml) was stirred for 24 hours at 80° C. The solvent was evaporated. MIK was added and azeotroped on the rotary evaporator. The residue was stirred in water, then extracted with $CH_2Cl_2$. The separated organic layer was washed with water, dried, filtered and the solvent evaporated. The residue was purified by column chromatography over silica gel (eluent: $CH_2Cl_2$/$CH_3OH$/THF 90/5/5 and $CH_2Cl_2$/$CH_3OH$ 90/10). The pure fractions were collected and the solvent was evaporated. The residue was stirred overnight in DIPE, then the solvent was evaporated. The residue was crystallized from EtOAc. The precipitate was filtered off, washed with EtOAc, DIPE, then dried, yielding 1.19 g (±)-2-[3-chloro-4-[(4-chlorophenyl)(4-methyl-1-piperazinyl)methyl]phenyl]-1,2,4-triazine-3,5(2H,4H)-dione (compound 118).

b) A mixture of 2-[3-chloro-4-[chloro(4-chlorophenyl)methyl]phenyl]-1,2,4-triazine-3,5(2H,4H)-dione (0.015 mol), 4-hydroxypiperidine (0.02 mol) and sodiumbicarbonate (0.02 mol) in DMF (100 ml) was stirred for 16 hours at 80° C. The mixture was cooled. The solvent was evaporated. The residue was purified by columnchromatography over silica gel (eluent: $CH_2Cl_2/CH_3OH$ 95/5). The desired fractions were collected and the solvent was evaporated. The residue was stirred in DIPE, filtered off and dried, yielding 0.070 g (±)-2-[3-chloro-4-[(4-chlorophenyl)(4-hydroxy-1-piperidinyl)methyl]phenyl]-1,2,4-triazine-3,5(2H,4H)-dione (compound 119).

c) (±)-2-[3-chloro-4-[(4-chlorophenyl)[(2-hydroxyethyl) amino]methyl]phenyl]-1,2,4-triazin-3,5(2H,4H)-dione was prepared according to the procedure described in example B3a but using $CH_3CN$ as a solvent instead of DMF (compound 51).

d) Methanol (100 ml) was stirred at RT and sodium (0.09 mol) was added. The mixture was stirred until complete dissolution. (1H-imidazol-2-yl)methanamine (0.045 mol) was added. The mixture was stirred for 30 minutes. NaCl was removed by filtration and the filtrate was evaporated. Toluene was added and azeotroped on the rotary evaporator. 2-[3-chloro-4-[chloro(4-chlorophenyl)methyl]phenyl]-1,2,4-triazine-3,5(2H,4H)-dione (0.015 mol) and acetonitrile (50 ml) were added. The resulting reaction mixture was stirred and refluxed for 20 hours. The solvent was evaporated, the residue was stirred in water, and extracted with $CH_2Cl_2/CH_3OH$ (90/10). The separated organic layer was dried, filtered, and the solvent evaporated. The residue was purified over silica gel on a glass filter (eluent: $CH_2Cl_2/CH_3OH$ 90/10). The pure fractions were collected and the solvent was evaporated. The residue was stirred in $CH_3CN$, filtered off, washed with DIPE, then dried, yielding 1.1 g (16.5%) of (±)-2-[3-chloro-4-[(4-chlorophenyl)[(1H-imidazol-2-ylmethyl)amino]methyl]phenyl]-1,2,4-triazine-3,5(2H,4H)-dione (compound 50).

e) (±)-2-[3-chloro-4-[(4-chlorophenyl)(2-pyrimidinylamino)methyl]phenyl]-1,2,4-triazine-3,5(2H,4H)-dione was prepared according to the procedure described in example B3a but using acetic acid as a solvent instead of DMF (compound 49).

f) (±)-2-[3-chloro-4-[(4-chlorophenyl)[(1-methyl)-4-piperidinyl)amino]methyl]phenyl]-1,2,4-triazine-3,5(2H,4H)-dione was prepared according to the procedure described in example B3a but using THF as a solvent instead of DMF (compound 48).

g) A mixture of 2-[4-[chloro(4-chlorophenyl)methyl]-3,5-dichlorophenyl]-1,2,4-triazine-3,5(2H,4H)-dione (0.00719 mol) and 2-pyrimidinamine (0.00863 mol) was heated for 2 hours at 150° C. in an autoclave. The mixture was cooled to RT. This fraction was taken up into $CH_2Cl_2$, washed with water, dried, filtered and the solvent was evaporated. The residue was purified by HPLC (eluent: (0.5% $NH_4OAc$ in $H_2O$)/$CH_3OH/CH_3CN$ gradient elution from 70/15/15 over 0/50/50 to 0/0/100). The desired fractions were collected and the solvent was evaporated. The residue was coevaporated with EtOAc. The residue was stirred in DIPE, filtered off, washed and dried, yielding 0.21 g of (±)-2-[3,5-dichloro-4-[(4-chlorophenyl)[(2-pyrimidinyl)amino]-methyl]phenyl]-1,2,4-triazine-3,5(2H,4H)-dione (comp. 413).

EXAMPLE B4 a) n-Butyllithium, 1.6M (0.0414 mol) was added dropwise at −70° C. under $N_2$ flow to a solution of 1-methyl-1H-imidazole (0.0414 mol) in diethyl ether (50 ml). The mixture was stirred at −70° C. for 90 minutes. A solution of 2-[3-chloro-4-(4-chlorobenzoyl)phenyl]-1,2,4-triazine-3,5(2H,4H)-dione (0.0138 mol) in THF (100 ml) was added dropwise. The mixture was allowed to warm to −40° C., then poured out into ice water, neutralized with HCl 3N and extracted with EtOAc. The organic layer was separated, dried, filtered and the solvent was evaporated. The residue (5.88 g) was purified by column chromatography over silica gel (eluent: $CH_2Cl_2/CH_3OH$ 97/3). The pure fractions were collected and the solvent was evaporated. The residue was taken up in $CH_3CN$ and diethyl ether. The precipitate was filtered off and dried, yielding 1.36 g (±)-2-[3-chloro[4-[(4-chlorophenyl)hydroxy(1-methyl-1H-imidazol-2-yl)methyl] phenyl]-1,2,4-triazine-3,5(2H,4H)-dione monohydrate (compound 120).

b) n-Butyllithium, 1.6M (0.0203 mol) was added dropwise at −70° C. under $N_2$ flow to a solution of 1-methyl-1H-imidazole (0.0203 mol) in THF (60 ml). The mixture was stirred at −70° C. for 40 minutes. Chlorotriethylsilane (0.203 mol) was added quickly and the mixture was allowed to warm to 0° C. on an ice bath. The mixture was cooled to −70° C. and n-butyllithium (0.0203 mol) was added dropwise. The mixture was allowed to warm to −20° C. and cooled to −70° C. A solution of 2-[3-chloro-4-(4-chlorobenzoyl)phenyl-1,2,4-triazine-3,5(2H,4H)-dione (0.00812 mol) in THF (20 ml) was added dropwise. The mixture was allowed to warm to −5° C., then poured out into a satured $NH_4Cl$ solution and ice, and extracted with EtOAc. The organic layer was separated, dried, filtered and the solvent was evaporated. The residue was purified by column chromatography over silica gel (eluent: $CH_2Cl_2/CH_3OH$ 96/4). The pure fractions were collected and the solvent was evaporated. The residue (0.85 g) was crystallized from 2-propanone and diethyl ether. The precipitate was filtered off and dried, yielding 0.47 g (13%) of (±)-2-[3-chloro-4-[(chlorophenyl)hydroxy(1-methyl-1H-imidazol-5-yl) methyl]phenyl]-1,2,4-triazine-3,5(2H,4H)-dione monohydrate (compound 121).

c) n-Butyllithium (0.1 mol) was added dropwise at −70° C. under $N_2$ flow to a solution of N,N-dimethylethanamine (0.1 mol) in THF (100 ml). The mixture was stirred at −20° C. for 30 minutes and cooled again to −70° C. Acetonitrile (0.1 mol) was added dropwise. The mixture was stirred at −20° C. for 1 hour and cooled again to −70° C. A solution of 2-[3,5-dichloro-4-(4-chlorobenzoyl)phenyl]-1,2,4-triazine-3,5(2H,4H)-dione (0.05 mol) in THF (100 ml) was added dropwise. The mixture was stirred at −70° C. for 1 hour, then poured out into $NH_4Cl$ 10% and extracted with EtOAc. The organic layer was separated, dried, filtered and the solvent was evaporated. The residue was purified by column chromatography over silica gel (eluent: $CH_2Cl_2/CH_3OH$ 98/2). Two pure fractions were collected and their solvents were evaporated, yielding 1.62 g (8%) of (±)-2,6-dichloro-α-(4-chlorophenyl)-4-[4,5-dihydro-3,5-dioxo-1,2,4-triazin-2(3H)-yl]-α-hydroxybenzenepropanenitrile (compound 122).

EXAMPLE B5 a) A mixture of intermediate (25) (0.0289 mol) in 2-mercaptoacetic acid (15 ml) was stirred at 150° C. for 3 hours and then cooled. The mixture was poured out in water, neutralized, and extracted with EtOAc. The organic layer was separated, dried, filtered and the solvent was evaporated. The residue was purified by column chromatography (eluent: $CH_2Cl_2/CH_3OH$ 98/2). The pure fractions were collected and the solvent was evaporated. A sample of this product was crystallized from 2-propanone and diethyl ether. The precipitate was filtered off and dried, yielding 1.2 g (±)-2-[3-chloro-4-[(4-chlorophenyl)(1-methyl-1H- imidazol-2-yl)methyl]phenyl]-1,2,4-triazine-3,5(2H,4H)-dione (compound 123).

b) (±)-2-[3-chloro-4-[(4-chlorophenyl)-3-pyridinylmethyl]phenyl]-1,2,4-triazine-3,5(2H,4H)-dione was prepared according to the procedure described in example B5a but using 1,2-dimethoxyethane instead of 2-mercaptoacetic acid (compound 124).

EXAMPLE B6 a) A mixture of intermediate (50) (0.0027 mol) in toluene (100 ml) was stirred and refluxed using a Dean-Stark apparatus. The mixture was decanted and the solvent evaporated. The residue was purified by column chromatography over silica gel (eluent: $CH_2Cl_2/CH_3OH$ 99/1). The pure fractions were collected and the solvent was evaporated. The residue was crystallized from diethyl ether. The precipitate was filtered off and dried, yielding 1.04 g (78%) (±)-2-[(3-chloro-4-[(4-chlorophenyl)(3-phenyl-1,2,4-oxadiazol-5-yl)methyl]phenyl]-1,2,4-triazine-3,5(2H,4H)-dione (compound 125).

b) (±)-2-[3,5-dichloro-4-[(4-chlorophenyl)(3-phenyl-1,2,4-oxadiazol-5-yl)methyl]phenyl]-1,2,4-triazin-3,5(2H,4H)-dione (comp. 429; mp. 128° C.) was prepared analogous to the procedure described in example B6.a except that the starting product was mixed with p-toluenesulfonic acid and dimethylsulfoxide instead of toluene.

EXAMPLE B7

A mixture of intermediate (66) (0.022 mol) and sodium methoxide, 30% in methanol (0.033 mol) in 1-butanol (350 ml) was stirred at RT for 30 minutes. Molecular sieves (12.6 g) and then EtOAc (0.033 mol) were added. The mixture was stirred and refluxed overnight, filtered over celite and the solvent was evaporated. The residue was taken up in $CH_2Cl_2$, washed with HCl 3N and then with water, dried, filtered and the solvent was evaporated. The residue was purified by column chromatography over silica gel (eluent: $CH_2Cl_2/CH_3OH$ 99/1). The pure fractions were collected and the solvent was evaporated. The residue was crystallized from 2-propanone and DIPE. The precipitate was filtered off and dried, yielding 2.1 g (±)-2-[3-chloro-4-[(4-chlorophenyl)(5-methyl-1,2,4-oxadiazol-3-yl)methyl]phenyl]-1,2,4-triazine-3,5(2H,4H)-dione (compound 126).

EXAMPLE B8 a) Intermediate (54) (0.00294 mol) was added portionwise at 5° C. to phosphoryl chloride (15 ml). The mixture was allowed to warm to RT, then stirred at 80° C. overnight and cooled. The solvent was evaporated. Ice water was added and the mixture was extracted with $CH_2Cl_2$. The organic layer was separated, washed with $H_2O$, dried, filtered and the solvent was evaporated. The residue was purified by column chromatography over silica gel (eluent: $CH_2Cl_2/CH_3OH$ 97.5/2.5). The pure fractions were collected and the solvent was evaporated. The residue was crystallized from 2-propanone and diethyl ether. The precipitate was filtered off and dried, yielding 0.5 g (±)-2-[3,5-dichloro-4-[(4-chlorophenyl)(5-phenyl-1,3,4-oxadizol-2-yl)methyl]-phenyl]-1,2,4-triazine-3,5(2H,4H)-dione (compound 127).

b) Compound 127 (0.0114 mol) was dissolved in hexane/ethanol/methanol 50/25/25 (400 ml), then separated into its enantiomers by chiral column chromatography over a Chiralpak AS column (230 g, 20 μm, I.D.: 5 cm; eluent: hexane/ethanol+0.1% $CF_3COOH$/methanol 66/17/17). Two fraction groups were collected. Fraction 1 was added to water. The organic solvent was evaporated and the aqueous concentrate was extracted with $CH_2Cl_2$. The solvent of the separated organic phase was evaporated. Fraction 2 was treated analogously. Both residues, each individually, were post-purified over Lichroprep 200 (eluent gradient: $CH_2Cl_2/CH_3OH$). Two pure fraction groups were collected and the solvent was evaporated, yielding 2.86 g (A)-2-[3,5-dichloro-4-[(4-chlorophenyl)(5-phenyl-1,3,4-oxadizol-2-yl)methyl]phenyl]-1,2,4-triazine-3,5(2H,4H)-dione (compound 189; $\alpha_{20}^{D}$=+50.98° (c=24.42 mg/5 ml in $CH_3OH$)) and 1.75 g (B)-2-[3,5-dichloro-4-[(4-chlorophenyl)(5-phenyl-1,3,4-oxadizol-2-yl)methyl]phenyl]-1,2,4-triazine-3,5(2H,4H)-dione (compound 190; $\alpha_{20}^{D}$=−50.83° (c=22.92 mg/5 ml in $CH_3OH$)).

EXAMPLE B9

A mixture of intermediate (59) (0.0108 mol) in toluene (120 ml) and methanesulfonic acid (1.05 ml) was stirred and refluxed for 4 hours, cooled, poured out into water, decanted, and basified to pH=8 with $NH_4OH$, while stirring. The aqueous layer was neutralized and extracted with $CH_2Cl_2$. The organic layer was washed with water, dried, filtered, and the solvent was evaporated. The residue was purified by column chromatography over silica gel (eluent: $CH_2Cl_2/CH_3OH$ 98/2). The desired fractions were collected and the solvent was evaporated. The residue was repurified by HPLC (eluent: $CH_3OH/H_2O$ 80/20). Two pure fractions were collected and their solvents were evaporated, yielding 0.44 g (8%) of (±)-2-[3-chloro-4-[(4-chlorophenyl)-[5-(phenylamino)-1,3,4-thiadizol-2-yl]methyl]phenyl]-1,2,4-triazine-3,5(2H,4H)-dione (compound 129), and 0.27 g (5%) of (±)-2-[3-chloro-4-[(4-chlorophenyl)(4,5-dihydro-4-phenyl-5-thioxo-1H-1,2,4-triazol-3-yl)methyl]phenyl]-1,2,4-triazine-3,5(2H,4H)-dione (compound 128)

EXAMPLE B10 a) A mixture of intermediate (65) (0.00275 mol) and triethylamine (0.003 mol) in THF (20 ml) was stirred at RT. Benzoyl chloride (0.00275 mol) in THF (10 ml) was added dropwise and the reaction mixture was stirred at RT for 3 hours. The solvent was evaporated. The residue was stirred in $H_2O$ and $CH_2Cl_2$. The organic layer was dried, filtered, and the solvent was evaporated. The residue was purified over silica gel on a glass filter (eluent: $CH_2Cl_2/CH_3OH$ 98/2). The desired fractions were collected and the solvent was evaporated. The residue was repurified by column chromatography over silica gel (eluent: $CH_2Cl_2/CH_3OH$ 98/2). The desired fractions were collected and the solvent was evaporated. The residue was stirred in DIPE, filtered off, washed with DIPE and dried. The residue was repurified by HPLC over silica gel (eluent: $CH_2Cl_2/CH_3OH$ 98/2). The desired fractions were collected and the solvent was evaporated. The residue was stirred in DIPE. The precipitate was filtered off, washed and dried, yielding 0.4 g (±)-N-[[2-chloro-4-(4,5-dihydro-3,5-dioxo-1,2,4-triazin-3(2H)-yl)phenyl](4-chlorophenyl)methyl]benzamide (compound 47).

b) A mixture of intermediate 65 (0.00275 mol) and 2-methylthiothiazolo[5,4-b]pyridine (0.0035 mol) was heated up to 170° C. and stirred for 2 days. The reaction mixture was dissolved in $CH_2Cl_2/CH_3OH$ (90/10). The precipitate was filtered off and the filtrate was evaporated. The residue was purified by flash column chromatography over silica gel (eluent: $CH_2Cl_2/CH_3OH$ 99/1). The desired fractions were collected and the solvent was evaporated. The residue was stirred in DIPE, filtered off, washed and dried, yielding 0.1 g of (±)-2-[3-chloro-4-[(4-chlorophenyl)[(thiazolo[5,4-b]pyridin-2-yl)amino]methyl]phenyl]-1,2,4-triazine-3,5(2H,4H)-dione. (comp. 410)

EXAMPLE B11

A solution of intermediate (63) (0.0080 mol), 6-chloro-2,4-dimethoxypyrimidine (0.0084 mol) and 1,8-diazabicyclo[5.4.0]undec-7-ene (0.0088 mol) in DMF (50 ml) was stirred for 4 days at RT. The solvent was evaporated and the residue was stirred in water and this mixture was extracted with $CH_2Cl_2/CH_3OH$ 90/10. The separated organic layer was dried, filtered, and the solvent was evaporated. The residue was purified by column chromatography over silica gel (eluent: $CH_2Cl_2/CH_3OH$ 98/2). The desired fractions were collected and the solvent was evaporated. The residue was repurified by reversed-phase liquid chromatography over silica gel (eluent: (0.5% $NH_4OAc$ in $H_2O$)/$CH_3OH/CH_3CN$ 28/36/36, upgrading to 0/50/50). The desired fractions were collected and the solvent was evaporated. The residue was stirred in DIPE, filtered off, washed, then dried, yielding 0.4 g (±)-2-[3-chloro-4-[(4-chlorophenyl)[(2,6-dimethoxy-2-pyrimidinyl)thio]methyl]phenyl]-1,2,4-triazine-3,5(2H,4H)-dione (compound 96).

EXAMPLE B12

A solution of intermediate (48) (0.012 mol) in pyridine (45 ml) was added to a solution of 2-mercapto-2-benzenamine (0.0132 mol) in pyridine (30 ml). The mixture was stirred and heated at 60° C. for 18 hours, poured out into HCl 3N, and extracted with $CH_2Cl_2$. The organic layer was separated, washed with $H_2O$, dried, filtered and the solvent was evaporated. The residue was purified by column chromatography over silica gel (eluent: $CH_2Cl_2/CH_3OH$ 99/1). The pure fractions were collected and the solvent was evaporated, yielding 1.23 g (21%) (±)-2-[4-[2-benzothiazolyl-(4-chlorophenyl)methyl]-3-chlorophenyl]-1,2,4-triazine-3,5(2H,4H)-dione (compound 130).

EXAMPLE B13 a) A mixture of 2,6-dichloro-α-(4-chlorophenyl)-4-(4,5-dihydro-3,5-dioxo-1,2,4-triazin-2(3H)-yl) benzeneethanethionate (0.00453 mol) and 2-bromo-1-phenylethanone (0.00498 mol) in ethanol (80 ml) was stirred and refluxed for 2 hours. The solvent was evaporated. The residue was taken up in $CH_2Cl_2$, washed with $K_2CO_3$ 10% and then with water, dried, filtered and the solvent was evaporated. The residue was purified by column chromatography over silica gel (eluent $CH_2Cl_2/CH_3OH/NH_4OH$ 90/10/0.5;). The pure fractions were collected and the solvent was evaporated. The residue was crystallized from DIPE. The precipitate was filtered off and dried, yielding 1.05 g (43%) of (±)-2-[3,5-dichloro-4-[(4-chlorophenyl)(4-phenyl-2-thiazolyl)methyl]phenyl]-1,2,4-triazine-3,5(2H,4H)-dione (compound 38).

b) (±)-2-[3,5-dichloro-4-[(4-chlorophenyl)[5-(1-methylethyl)-4-phenyl-2-thiazolyl]methyl]-phenyl-1,2,4-triazin-3,5(2H,4H)-dione (comp. 241) was prepared according to example B13.a and in addition triethylamine was used as a base.

c) 2,6-Dichloro-α-(4-chlorophenyl)-4-(4,5-dihydro-3,5-dioxo-1,2,4-triazin-2(3H)-yl)benzeneethanethiomide (0.031 mol) was added at RT to a solution of (±)-1,1-dimethylethyl α-bromo-β-oxo-benzenepropanoate (0.0465 mol) and $K_2CO_3$ (0.093 mol) in $CH_3CN$ (190 ml). The mixture was stirred at RT for 3.5 hours. $H_2O$ was added. The mixture was acidified with HCl 3N and extracted with EtOAc. The organic layer was separated, dried, filtered and the solvent was evaporated. The residue was purified by column chromatography over silica gel (eluent: $CH_2Cl_2/CH_3OH$ 99/1). The pure fractions were collected and the solvent was evaporated, yielding 11 g (54%) of (±)-1,1-dimethylethyl 2-[(4-chlorophenyl)[2,6-dichloro-4-(4,5-dihydro-3,5-dioxo-1,2,4-triazin-2(3H)-yl)phenyl]methyl]-4-phenyl-5-thiazolcarboxylate (comp. 298).

EXAMPLE B14

A mixture of 2,6-dichloro-α-(4-chlorophenyl)-4-(4,5-dihydro-3,5-dioxo-1,2,4-triazin-2(3H)-yl) benzeneethanethionate (0.0197 mol) and 1-bromo-2,2-diethoxyethane (0.0256 mol) in HCl 3N (10 ml) and ethanol (145 ml) was stirred and refluxed for 5 hours. The solvent was evaporated. The residue was taken up in $CH_2Cl_2$, washed with $K_2CO_3$ 10% and extracted with $CH_2Cl_2$. The organic layer was separated, washed with water, dried, filtered and the solvent was evaporated. The residue was purified by column chromatography over silica gel (eluent: $CH_2Cl_2/CH_3OH/NH_4OH$ 85/15/1). The pure fractions were collected and the solvent was evaporated. The residue was crystallized from DIPE. The precipitate was filtered off, dried and recrystallized from 2-propanone and diethyl ether. The precipitate was filtered off and dried, yielding 1.32 g (±)-2-[3,5-dichloro-4-[(4-chlorophenyl)-2-thiazolylmethyl]-phenyl]-1,2,4-triazine-3,5(2H,4H)-dione (compound 39).

EXAMPLE B15 a) A mixture of intermediate (52) (0.0076 mol) in EtOAc (45 ml) was stirred and refluxed for 18 hours, then poured out into $H_2O$ and extracted with EtOAc. The organic layer was separated, washed with $K_2CO_3$ 10% and with $H_2O$, dried, filtered and the solvent was evaporated. The residue was purified by column chromatography over silica gel (eluent: $CH_2Cl_2/CH_3OH$ 99/1). The pure fractions were collected and the solvent was evaporated, yielding 0.9 g (25%) of (±)-2-[4-[2-benzoxazolyl(4-chlorophenyl)methyl]-3-chlorophenyl]-1,2,4-triazine-3,5(2H,4H)-dione (compound 131).

b) (±)-2-[3-chloro-4-[1-(4-chlorophenyl)-1-(2-benzoxazolyl)ethyl]phenyl]-1,2,4-triazine-3,5(2H,4H)-dione was prepared using the same procedure as in example B15a but by using methanesulfonic acid instead of acetic acid (compound 132).

EXAMPLE B16

A mixture of compound (33) (0.0231 mol) in methanol (100 ml) and sulfonic acid (2 ml) was stirred and refluxed for 3 days, then cooled, poured out on ice, neutralized and extracted with $CH_2C_2$. The organic layer was separated, dried, filtered and the solvent was evaporated. The residue was purified by column chromatography over silica gel (eluent: $CH_2Cl_2/CH_3OH$ 99/1 to 98/2). The pure fractions were collected and the solvent was evaporated, yielding 4 g (38%) of (±)-2-[3-chloro-4-[(4-chlorophenyl)-methoxy(2-thiazolyl)methyl]phenyl]-1,2,4-triazine-3,5(2H,4H)-dione (compound 37).

EXAMPLE B17 a) Compound (33) (0.00425 mol) was dissolved in thionyl chloride (20 ml) at 10° C., and the mixture was stirred at RT for 4 hours. The solvent was evaporated, yielding (±)-2-[3-chloro-4-[chloro(4-chlorophenyl)-2-thiazolylmethyl]phenyl]-1,2,4-triazine-3,5(2H,4H)-dione (compound 36).

b) A solution of compound (36) (0.00425 mol) in THF (20 ml) was added dropwise at 5° C. to $NH_4OH$ (20 ml) and the mixture was stirred at RT for 2 hours, then poured out on ice, neutralized with HCl 6N and extracted with EtOAc. The organic layer was separated, dried, filtered and the solvent was evaporated. The residue was purified by column chromatography over silica gel (eluent: $CH_2Cl_2/CH_3OH$ 97/3). The pure fractions were collected and the solvent was evaporated. The residue was repurified by column chromatography over Kromasil C18 (eluent: $CH_3OH/H_2O/HOAc$ 70/30/1). The pure fractions were collected and the solvent was evaporated. The residue was taken up in $H_2O$ and $NH_4OH$ (pH=8) was added. The precipitate was filtered off, washed with $H_2O$ and diethyl ether, and dried, yielding 0.3 g (±)-2-[3-chloro-4-[amino-(4-chlorophenyl)-2-thiazolylmethyl]phenyl]-1,2,4-triazine-3,5(2H,4H)-dione (compound 35).

EXAMPLE B18

A mixture of 2-[3,5-dichloro-4-[(4-chlorophenyl) hydroxymethyl]phenyl]-1,2,4-triazine-3,5(2H,4H)-dione (0.005 mol) and 5-phenyl-1,3,4-oxadiazole-2(3H)-thione (0.006 mol) in methanesulfonic acid (20 ml) was stirred for 18 hours at RT. The reaction mixture was poured out into water/ice (150 ml), and the resulting precipitate was filtered off, stirred in water, treated with $NaHCO_3$ and this mixture was extracted with $CH_2Cl_2$. The separated organic layer was dried, filtered and the solvent evaporated. The residue was purified by flash column chromatography over silica gel (eluent: $CH_2Cl_2/CH_3OH$ 97.5/2.5). The pure fractions were collected and the solvent was evaporated. The residue was stirred in DIPE, filtered off and dried, yielding 1 g of (±)-2-[3,5-dichloro-4-[(4-chlorophenyl)[(5-phenyl-1,3,4-oxadiazol-2-yl)thio]methyl]phenyl]-1,2,4-triazine-3,5(2H,4H)-dione (comp. 406).

EXAMPLE B19 a) A solution of 2,6-dichloro-α-(4-chlorophenyl)-4-(4,5-dihydro-3,5-dioxo-1,2,4-triazin-2(3H)-yl)benzeneacetyl chloride (0.188 mol) in 1,4-dioxane (900 ml) was stirred at RT. $NaBH_4$ (36.25 g) was added portionwise over 2.5 hours. The resulting reaction mixture was stirred for 3 hours at RT. The reaction mixture was cooled and acidified till pH 6 with 1 N HCl. The precipitated salts were removed by filtration. The filtrate was washed with water, and the precipitate was filtered off, stirred in DIPE, filtered off and dried, yielding 22.5 g of (±)-2-[3,5-dichloro-4-[1-(4-chlorophenyl)-2-hydroxyethyl]phenyl]-1,2,4-triazine-3,5(2H,4H)-dione (comp. 420). The biphasic filtrate was separated into its layers. The organic layer was dried, filtered and the solvent was evaporated. The residue was purified by HPLC over silica gel (eluent: $CH_2Cl_2/CH_3OH$ 98.5/1.5 and 97/3). The pure fractions were collected and the solvent was evaporated. The residue was stirred in DIPE, filtered off, washed, and dried, yielding 24 g of (±)-2-[3,5-dichloro-4-[1-(4-chlorophenyl)-2-hydroxyethyl]phenyl]-1,2,4-triazin-3,5(2H,4H)-dione (comp. 420).

b) A solution of compound 420 (0.01 mol) and N-ethyl-N-(1-methylethyl)-2-propanamine (0.02 mol) in 1,4-dioxane (80 ml) was stirred at 5–10° C. under $N_2$ atmosphere. A solution of methanesulfonyl chloride (0.02 mol) in 1,4-dioxane (10 ml) was added dropwise at 5–10° C. The resulting reaction mixture was stirred for one hour at RT. The solvent was evaporated under reduced pressure. The residue was dissolved in $CH_2C_2$, washed with water, dried, filtered and the solvent was evaporated, yielding 4.9 g of (±)-2-[2,6-dichloro-4-(4,5-dihydro-3,5-dioxo-1,2,4-triazin-2(3H)-yl)phenyl]-2-(4-chlorophenyl)ethanol methanesulfonate (ester) (comp. 435).

c) A mixture of compound 435 (0.001 mol), 2-pyridinethiol (0.0012 mol) and $NaHCO_3$ (0.0012 mol) in DMF (30 ml) was stirred at RT under $N_2$ flow, then heated to 60° C. and stirred for 48 hours. 2-pyridinethiol (0.0012 mol) and $NaHCO_3$ (0.0012 mol) were added again. The mixture was stirred for 1 day. 2-pyridinethiol (0.006 mol) was added again and the mixture was stirred and refluxed for 1 day. The solvent was evaporated under reduced pressure. The residue was dissolved in $CH_2Cl_2$ and extracted with water. The organic layer was separated, dried, filtered and the solvent was evaporated. The residue was purified by HPLC (eluent: $NH_4OAc$ 0.5% in $H_2O/CH_3OH/CH_3CN$ 67.5/7.5/25 to 0/50/50 after 10 minutes to 0/0/100 after 10 minutes). The desired fractions were collected and the solvent was evaporated. The residue was stirred in DIPE. The precipitate was filtered off, washed and dried, yielding 0.05 g (10%) of (±)-2-[3,5-dichloro[1-(4-chlorophenyl)-2-(2-pyridinylthio)ethyl]phenyl-1,2,4-triazine-3,5(2H,4H)-dione (comp. 422).

EXAMPLE B20

A mixture of intermediate 75 (0.0159 mol) in dimethylsulfoxide (170 ml) and $H_2O$ (20 ml) was stirred at 160° C. for 3 hours. The mixture was cooled and poured out on ice. The precipitate was filtered off, washed with $H_2O$ and taken up in EtOAc. The organic solution was dried, filtered and the solvent was evaporated. The residue was purified by column chromatography over silica gel (eluent: $CH_2Cl_2/CH_3OH$ 99.5/0.5 to 96/4). The desired fraction was collected and the solvent was evaporated, yielding 2015 g of (±)-2-[3-chloro-4-[(4-chlorophenyl)(4-phenyl-2-thiazolyl)methyl]phenyl]-1,2,4-triazine-3,5(2H,4H)-dione (comp. 419; mp. 90° C.).

EXAMPLE B21

A mixture of (±)-2-[4-[3-bromo-1-(4-chlorophenyl)-2-oxopropyl]-3,5-dichlorophenyl]-1,2,4-triazin-3,5(2H,4H)-dione (0.0025 mol) and benzenecarbothioamide (0.0025 mol) in ethanol (25 ml) was stirred and refluxed for 3 hours, then stirred overnight at RT. The solvent was evaporated. The residue was purified twice by column chromatography over silica gel (eluent: $CH_2Cl_2/CH_3OH$ (1) 97/3 and (2) 98/2 v/v). The desired fractions were collected and the solvent was evaporated. The residue was repurified by column chromatography over silica gel (eluent: $CH_2Cl_2/CH_3OH$ 99/1). The pure fractions were collected and the solvent was evaporated. The residue was stirred in hexane, filtered off, then dried, yielding 0.3 g (22%) of (±)-2-[3,5-dichloro-4-[(4-chlorophenyl)(2-phenyl-4-thiazoyl)methyl]phenyl]-1,2,4-triazine-3,5(2H,4H)-dione (comp. 363).

EXAMPLE B22 a) Compound 298 (0.0137 mol) was added at 10° C. under $N_2$ flow to trifluoroacetic acid (120 ml). The mixture was allowed to warm to RT and stirred for 1 hour. $H_2O$ was added. The precipitate was filtered off, washed with $H_2O$ and taken up in $CH_2Cl_2$ and a small amount of $CH_3OH$. The organic layer was separated, dried, filtered and the solvent was evaporated. The residue was crystallized from $CH_3CN$. The precipitate was filtered off and the filtrate was evaporated. The residue was purified by column chromatography over silica gel (eluent: $CH_2Cl_2/CH_3OH/HOAc$ 97/3/0.1). The pure fractions were collected and the solvent was evaporated. This fraction was crystallized from $CH_3CN$. The precipitate was filtered off and dried, yielding 1.34 g (67%) of (±)-2-[(4-chlorophenyl)[2,6-dichloro-4-(4,5-dihydro-3,5-dioxo-1,2,4-triazin-2(3H)-yl)phenyl]-methyl]-4-phenyl-5-thiazolcarboxylic acid (Comp. 299; mp 206° C.).

b) 1,1'-Carbonylbis-1H-imidazole (0.0081 mol) was added to a suspension of compound 299 (0.00324 mol) in $CH_2Cl_2$ (25 ml). The mixture was stirred at RT for 2 hours. Dimethylamine (0.00324 mol) was added. The mixture was stirred at RT for 48 hours. $H_2O$ was added. The mixture was acidified with HCl 3N and extracted with $CH_2Cl_2$. The organic layer was separated, dried, filtered and the solvent was evaporated. The residue was purified by column chromatography over silica gel (eluent: $CH_2Cl_2/CH_3OH$ 98.5/1.5). The pure fractions were collected and the solvent was evaporated. The residue was crystallized from DIPE. The precipitate was filtered off and dried, yielding 1.04 g (52%) of (±)-N,N-dimethyl-2-[(4-chlorophenyl)[2,6-dichloro-4-(4,5-dihydro-3,5-dioxo-1,2,4-triazin-2(3H)-yl)phenyl]methyl]-4-phenylthiazol-5-carboxamide (Comp. 303; mp 150° C.).

EXAMPLE B23 a) A solution of compound 350 (0.014 mol) in 2,6-dimethylpyridine (1.63 ml) and THF (80 ml) was stirred and cooled to −78° C. Trifluoromethanesulfonic anhydride (0.014 mol) was added dropwise and the mixture was stirred for 7 hours at −78° C., yielding (±)-2-[[(4-chlorophenyl)[2,6-dichloro-4-(4,5-dihydro-3,5-dioxo-1,2,4-triazin-2(3H)-yl)phenyl]methyl]thio]4-pyrimidinol trifluoromethanesulfonate (ester) (comp. 356).

b) A mixture of compound 356 (0.0047 mol) in THF (35 ml) was stirred at RT. 2-Aminoethanol (0.0235 mol) was added. The reaction mixture was stirred for one hour at 50° C., then for 16 hours at RT. The solvent was evaporated. The residue was purified by flash column chromatography over silica gel (eluent: $CH_2Cl_2/CH_3OH$ 99/1, 98/2 and 93/7). The desired fractions were collected and the solvent was evaporated. The residue was repurified by HPLC over silica gel (eluent: $CH_2Cl_2/CH_3OH$ from 100/0 over 30 minutes to 92/8). The desired fractions were collected and the solvent was evaporated. The residue was stirred in DIPE, filtered off, washed and dried, yielding 0.3 g of (±)-2-[3,5-dichloro-4-[(4-chlorophenyl)[[4-[(2-hydroxyethyl)amino]-2-pyrimidinyl]-thio]methyl]phenyl]-1,2,4-triazine-3,5(2H,4H)-dione (comp. 357).

EXAMPLE B24 a) LiCl (0.035 mol) was added portionwise at 80° C. to a mixture of compound 285 (0.007 mol) and $KBH_4$ (0.035 mol) in THF (45 ml). The mixture was stirred at 80° C. for 4 hours. $KBH_4$ (0.035 mol) and then LiCl (0.035 mol) were added. The mixture was stirred at 80° C. for 4 hours, at RT overnight, then poured out into ice water, acidified with HCl 3N and extracted with $CH_2Cl_2$. The organic layer was separated, dried, filtered and the solvent was evaporated. The residue was purified by column chromatography over silica gel (eluent: $CH_2C_2/CH_3OH$ 97/3; 20–45 $\mu$m). The pure fractions were collected and the solvent was evaporated, yielding 2.1 g (51%) of (±)-2-[3,5-dichloro-4-[(4-chlorophenyl)[4-(2-fluorophenyl)-5-(hydroxymethyl)-2-thiazolyl]methyl]phenyl]-1,2,4-triazin-3,5(2H,4H)-dione (comp. 323).

b) Thionylchloride (0.0113 mol) was added at 10° C. to a mixture of compound 323 (0.0094 mol) in $CH_2Cl_2$ (30 ml). The mixture was stirred at RT for 2.5 hours, washed with $H_2O$ and with $K_2CO_3$ 10%, dried, filtered and the solvent was evaporated, yielding 2 g of (±)-2-[4-[[5-(chloromethyl)-4-(2-fluorophenyl)-2-thiazolyl](4-chlorophenyl)methyl]-3,5-dichloropropenyl]-1,2,4-triazine-3,5(2H,4H)-dione (comp. 324).

c) A mixture of compound 324 (0.0034 mol), dimethylamine (0.0068 mol) and $K_2CO_3$ (0.0102 mol) in $CH_3CN$ (100 ml) was stirred and refluxed for 3 hours and then cooled. The solvent was evaporated. The residue was taken up in $CH_2Cl_2$. The organic solution was washed with $H_2O$, dried, filtered and the solvent was evaporated. The residue was purified by column chromatography over silica gel (eluent: $CH_2Cl_2/CH_3OH/H_2O$ 97/3/0.4). The pure fractions were collected and the solvent was evaporated. The residue was crystallized from diethyl ether and $CH_3CN$. The precipitate was filtered off and dried, yielding 0.84 g of (±)-2-[4-[(4-chlorophenyl)[5-[(dimethylamino)methyl]-4-(2-fluorophenyl)-2-thiazolyl]methyl]-3,5-dichlorophenyl]-1,2,4-triazine-3,5(2H,4H)-dione (comp. 325; mp 250° C.).

EXAMPLE B25

A mixture of compound 229 (0.0041 mol) and triethylamine (0.0082 mol) in $CH_2Cl_2$ (45 ml) was stirred at RT for 1 hour. A solution of acetyl chloride (0.0041 mol) in $CH_2Cl_2$ (5 ml) was added at 10° C. The mixture was stirred at RT for 12 hours, then poured out into $H_2O$ and decanted. The organic layer was washed with HCl 3N and with $H_2O$, dried, filtered and the solvent was evaporated. The residue was purified by column chromatography over silica gel (eluent: $CH_2C_2/CH_3OH$ 95/5). The pure fractions were collected and the solvent was evaporated. The residue was crystallized from $CH_3CN$ and DIPE. The precipitate was filtered off and dried, yielding 0.52 g of (±)-2-[3,5-dichloro-4-[(4-chlorophenyl)[4-(4-piperidinyl)-2-thiazolyl]methyl]phenyl]-1,2,4-triazin-3,5-(2H,4H)-dione monohydrochloride (comp. 230; mp 212° C.).

EXAMPLE B26

A mixture of compound 212 (0.00646 mol) in $NH_3/CH_3OH$ 7N (100 ml) was stirred and refluxed for 3 hours and then cooled. The solvent was evaporated. The residue was taken up in EtOAc and a small amount of $CH_3OH$. The organic layer was separated, washed with HCl 3N, dried, filtered and the solvent was evaporated. The residue was purified by column chromatography over silica gel (eluent: $CH_2Cl_2/CH_3OH$ 97/3). The pure fractions were collected and the solvent was evaporated. The residue was crystallized from 2-propanone and diethyl ether. The precipitate was filtered off and dried, yielding 0.85 g of (±)-N-[2-[5-[(4-chlorophenyl)[2,6-dichloro-4-(4,5-dihydro-3,5-dioxo-1,2,4-triazin-2(3H)-yl)phenyl]methyl]-1,3,4-oxadiazol-2-yl]phenyl]-2-hydroxyacetamide (comp. 213; mp 235° C.).

EXAMPLE B27

A mixture of compound 352 (0.005 mol) in HBr (75 ml; 48%) was stirred at RT. The mixture was warmed to 140° C. on an oil bath and stirred for 30 minutes. The mixture was cooled. The solvent was evaporated. $H_2O$ was added. The mixture was neutralized with NaOH 50% and extracted with $CH_2Cl_2$. The product was filtered off and stirred in $CH_3OH$, in $CH_3CN$ and then in $CH_2Cl_2$, and dried. This fraction was stirred in $H_2O$ (20 ml), and $CH_3COOH$ (±1 equiv) was addded. The product was filtered off, washed with $H_2O$ and dried, yielding 1.3 g of (±)-2-[3,5-dichloro-4-[(4-chlorophenyl)[[4-(1-piperazinyl)-2-pyrimidinyl]thio]methyl]phenyl]-1,2,4-triazine-3,5(2H,4H)-dione monohydrate (comp. 360).

EXAMPLE B28 a) A mixture of compound 192 (0.014 mol) in THF (100 ml) and methanol (100 ml) was hydrogenated at 50° C. with platina on activated charcoal (2 g; 10%) as a catalyst in the presence of a thiophene solution (2 ml). After uptake of $H_2$, the catalyst was filtered off and the filtrate was evaporated. Toluene was added and azeotroped on the rotary evaporator, yielding 6.2 g of (±)-2-[4-[[5-(3-aminophenyl)-1,3,4-oxadiazol-2-yl](4-chlorophenyl)methyl]-3,5-dichlorophenyl]-1,2,4-triazine-3,5(2H,4H)-dione (comp. 193).

b) Compound 193 (0.012 mol) was dissolved in acetic acid (40 ml) and HCl (3.6 ml) at about 5° C. A solution of $NaNO_2$ (0.0126 mol) in $H_2O$ (10 ml) was added dropwise at 5° C. The reaction mixture was stirred for 1 hour at 5° C. $NaN_3$ (0.0126 mol) was added portionwise. The reaction mixture was stirred for 30 minutes, then poured out onto ice. The precipitate was filtered off, washed with water, then dissolved in $CH_2Cl_2$. The organic solution was dried, filtered, and the solvent was evaporated. The residue was purified by HPLC over silica gel (eluent: $CH_2Cl_2/CH_3OH$ 98/2). The pure fractions were collected and the solvent was evaporated. The residue was stirred in boiling ethanol, filtered off and washed with ethanol/DIPE, then dried, yielding 2.1 g of (±)-2-[4-[[5-(3-azidophenyl)-1,3,4-oxadiazol-2-yl](4-chlorophenyl)methyl]-3,5-dichlorophenyl]-1,2,4-triazine-3,5(2H,4H)-dione (comp. 194).

EXAMPLE B29 a) A mixture of compound 328 (0.00271 mol) in HBr (20 ml; 33% in HOAc) and HBr (20 ml; 48% in $H_2O$) was stirred and refluxed overnight, then cooled, poured out into ice water, neutralized with a concentrated NaOH solution and centrifuged. The residue was washed with $H_2O$ and dried. The residue was purified by column chromatography over silica gel (eluent: $CH_2Cl_2/CH_3OH$ 95/5). The pure fractions were collected and the solvent was evaporated. The residue was taken up in $CH_3OH$ and $CH_2Cl_2$. The organic solution was washed with a solution at pH 4 and a solution at pH 7, then dried. Activated charcoal was added. The mixture was filtered over celite. The solvent was evaporated. The residue was crystallized from $CH_3CN$ and diethyl ether. The precipitate was filtered off and dried, yielding 0.27 g of (±)-2-[4-[[5-(aminomethyl)-4-phenyl-2-thiazolyl](4-chlorophenyl)methyl]-3,5-dichlorophenyl]-1,2,4-triazine-3,5(2H,4H)-dione (comp. 329; mp 170° C.).

b) A solution of compound 329 (0.0035 mol) and isothiocyanatobenzene (0.0042 mol) in THF (25 ml) was stirred at RT for 90 minutes. The solvent was evaporated. The residue was dissolved in $CH_2Cl_2$. The organic solution was washed with $H_2O$, dried, filtered and the solvent was evaporated. The residue was purified by column chromatography over silica gel (eluent: $CH_2Cl_2/CH_3OH$ 98/2). The pure fractions were collected and the solvent was evaporated. The residue was taken up in DIPE. The precipitate was filtered off and dried, yielding 0.64 g (±)-N-[[2-[(4-chlorophenyl)[2,6-dichloro-(4,5-dihydro-3,5-dioxo-1,2,4-triazin-2(3H)-yl)phenyl]methyl]4-phenyl-5-thiazolyl]methyl]-N'-phenylthiourea (comp. 331; mp 159° C.).

EXAMPLE B30 a) $TiCl_3$ (0.034 mol; 15% aqueous solution) was added dropwise at RT to a mixture of compound 216 (0.0034 mol) in THF (60 ml). The mixture was stirred at RT for 5 hours, poured out into $H_2O$ and extracted with EtOAc. The organic layer was separated, washed with $H_2O$, dried, filtered and the solvent was evaporated, yielding 1.9 g of (±)-2-[4-[[5-(3-amino-2-methylphenyl)-1,3,4-oxadiazol-2-yl](4-chlorophenyl)methyl]-3,5-dichlorophenyl]-1,2,4-triazine-3,5(2H,4H)-dione (comp. 217).

b) A mixture of (acetyloxy)acetyl chloride (0.0121 mol) in $CH_2Cl_2$ (15 ml) was added at 10° C. under $N_2$ flow to a mixture of compound 217 (0.011 mol) and N-ethyl-N-(1-methylethyl)-2-propanamine (0.0165 mol) in $CH_2Cl_2$ (60 ml). The mixture was stirred at RT for 12 hours, poured out into $H_2O$, acidified with HCl 3N and extracted with $CH_2Cl_2$. The organic layer was separated, dried, filtered and the solvent was evaporated. The residue was purified by column chromatography over silica gel (eluent: $CH_2Cl_2/CH_3OH$ 97/3). The pure fractions were collected and the solvent was evaporated. Part of the residue (0.9 g) was crystallized from diethyl ether and $CH_3CN$. The precipitate was filtered off and dried, yielding 0.65 g of (±)-2-(acetyloxy)-N-[3-[5-[(4-chlorophenyl)[2,6-dichloro-(4,5-dihydro-3,5-dioxo-1,2,4-triazin-2(3H)yl)phenyl]methyl]-1,3,4-oxadiazol-2-yl]-2-methylphenyl]acetamide. (comp. 223; mp 206° C.).

Tables 1 to 8 list compounds of the present invention as prepared according to one of the above examples. These all are racemic mixtures unless otherwise mentioned.

TABLE 1

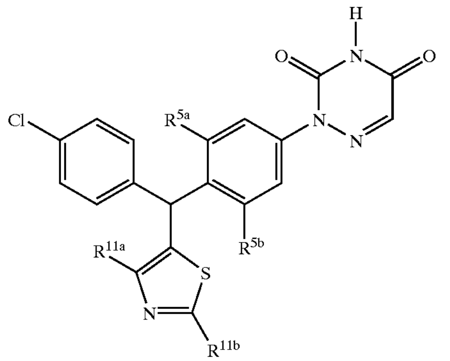

| Co. No. | Ex. No. | $R^{5a}$ | $R^{5b}$ | $R^{11a}$ | $R^{11b}$ | Melting-point ° C. |
|---|---|---|---|---|---|---|
| 134 | B5a | Cl | H | phenyl | CH3 | 180° C. |
| 135 | B5a | Cl | Cl | 2-Cl-phenyl | CH3 | 170° C. |
| 136 | B5a | Cl | Cl | phenyl | $CH_3$ | 175° C. |
| 137 | B5a | Cl | Cl | $CH_3$ | 2-Cl-phenyl | 120° C. |
| 138 | B5a | Cl | Cl | $CH_3$ | phenyl | 120° C. |
| 139 | B5a | Cl | H | 2-Cl-phenyl | $CH_3$ | >260° C. |
| 140 | B5a | Cl | H | phenyl | phenyl | 186–188° C. |
| 141 | B5a | Cl | H | H | phenyl | 168° C. |
| 142 | B5a | Cl | Cl | H | phenyl | |
| 143 | B5a | Cl | H | 3-F-phenyl | $CH_3$ | 146° C. |
| 144 | B5a | H | Cl | 2-Cl-phenyl | phenyl | 140° C. |
| 145 | B5a | Cl | Cl | 2-Cl-phenyl | phenyl | 160° C. |
| 146 | B5a | H | H | phenyl | $CH_3$ | 230° C. |
| 147 | B5a | Cl | Cl | 2-Cl-phenyl | 2-Cl-phenyl | 158° C. |
| 148 | B5a | Cl | H | 3-F-phenyl | H | 155° C. |
| 149 | B5a | Cl | H | 4-Cl-phenyl | $CH_3$ | 145° C. |
| 150 | B5a | Cl | H | phenyl | 2-Cl-phenyl | 220° C. |
| 151 | B5a | Cl | H | 2-Cl-phenyl | 2-Cl-phenyl | 150° C. |
| 152 | B5a | Cl | Cl | 2-F-phenyl | $CH_3$ | 185° C. |
| 153 | B5a | H | $OCH_3$ | phenyl | $CH_3$ | 163° C. |
| 154 | B5a | Cl | H | $CH_3$ | 2-Cl-phenyl | 190° C. |

TABLE 2

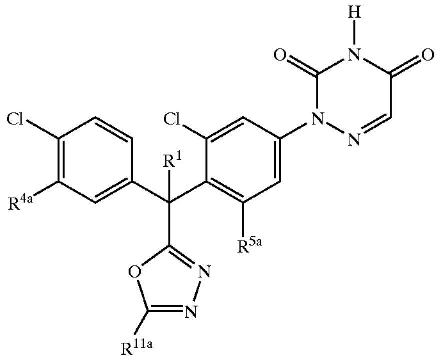

| Co. No. | Ex. No. | $R^1$ | $R^{4a}$ | $R^{5a}$ | $R^{11a}$ | salt form/ stereochemistry/ melting point |
|---|---|---|---|---|---|---|
| 155 | B8a | $CH_3$ | $CF_3$ | H | phenyl | 126° C. |
| 156 | B8a | H | H | Cl | 2-F-phenyl | 169° C. |
| 157 | B8a | H | H | Cl | 3-Cl-phenyl | 188° C. |
| 158 | B8a | H | H | Cl | 4-pyridinyl | $H_2O$ (1:1)/ 170° C. |
| 159 | B8a | H | H | Cl | cyclohexyl | 164° C. |
| 160 | B8a | H | H | Cl | 3-F-phenyl | 156° C. |
| 161 | B8a | H | H | Cl | 2-furanyl | 170° C. |
| 162 | B8a | H | H | Cl | methyl | 120° C. |
| 163 | B8a | H | H | Cl | 2-Cl-phenyl | $H_2O$ (1:1)/ 160° C. |
| 164 | B8a | H | H | Cl | propyl | 135° C. |
| 165 | B8a | H | $CF_3$ | Cl | phenyl | 212° C. |
| 166 | B8a | H | H | Cl | 2-thienyl | 180° C. |
| 167 | B8a | H | H | Cl | 4-Cl-phenyl | 230° C. |
| 168 | B8a | H | H | Cl | 4-Br-phenyl | |
| 169 | B8a | H | H | Cl | 2-pyridinyl | 182° C. |
| 170 | B8a | H | H | Cl | 3-methoxyphenyl | 208° C. |
| 171 | B8a | H | H | Cl | 2-methoxyphenyl | 212° C. |
| 172 | B8a | H | H | Cl | phenylethyl | 148° C. |
| 173 | B8a | H | H | Cl | phenyl-$CH_2$— | 190° C. |
| 174 | B8a | H | H | Cl | 2-(methoxy)phenyl | 164° C. |
| 175 | B8a | H | H | Cl | (2-Cl-phenyl)-O—$CH_2$— | 135° C. |
| 176 | B8a | H | H | Cl | $C_2H_5$—O—CO—$CH_2$— | 177° C. |
| 177 | B8a | H | H | Cl | 4-$CH_3$-phenyl | >260° C. |
| 178 | B8a | H | H | Cl | 3-$CH_3$-phenyl | 188° C. |
| 179 | B8a | H | H | Cl | NC—$CH_2$— | 222° C. |
| 180 | B8a | H | H | Cl | 4-[$N(CH_3)_2$]-phenyl | 224° C. |
| 181 | B8a | H | H | Cl | $C_2H_5$—O—$(CH_2)_2$— | 130° C. |
| 182 | B8a | H | H | Cl | 3-[$N(CH_3)_2$]-phenyl | 240° C. |
| 183 | B2a | H | H | Cl | 4-nitrophenyl | |
| 184 | B28 | H | H | Cl | 4-aminophenyl | |
| 185 | B28b | H | H | Cl | 4-(—$N{=}N^+{=}N^-$)-phenyl | |
| 186 | B8a | H | H | Cl | $C_2H_5$—O—CO— | 137° C. |
| 187 | B8a | H | H | Cl | phenyl-O—$(CH_2)_2$— | 215° C. |
| 188 | B8a | H | H | Cl | 2-$CH_3$-phenyl | 150° C. |
| 189 | B8b | H | H | Cl | phenyl | (A) |
| 190 | B8b | H | H | Cl | phenyl | (B) |
| 191 | B8a | H | H | Cl | 1-($C_2H_5$—O—CO)-4-piperidinyl | 230° C. |
| 192 | B8a | H | H | Cl | 3-nitrophenyl | |
| 193 | B28a | H | H | Cl | 3-aminophenyl | |
| 194 | B28b | H | H | Cl | 3-(—$N{=}N^+{=}N^-$)-phenyl | |
| 195 | B8a | H | H | Cl | 1-$CH_3$-4-piperidinyl | |
| 196 | B8a | H | H | Cl | 1-$CH_3$-3-piperidinyl | 150° C. |
| 197 | B8a | H | H | Cl | Cl—$CH_2$— | |
| 198 | B24c | H | H | Cl | $(CH_3)_2$—N—$CH_2$— | 188° C. |
| 199 | B8a | H | H | Cl | 4-(4-$CH_3$-1-piperazinyl)phenyl | 150° C. |
| 200 | B8a | H | H | Cl | 3-OH-phenyl | 159° C. |
| 201 | B8a | H | H | Cl | 3-pyridinyl | 190° C. |
| 202 | B8a | H | H | Cl | 2-hydroxyphenyl | 180° C. |

TABLE 2-continued

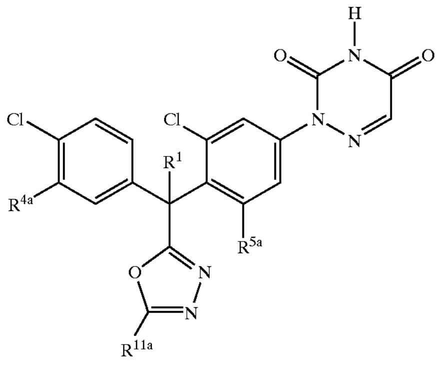

| Co. No. | Ex. No. | $R^1$ | $R^{4a}$ | $R^{5a}$ | $R^{11a}$ | salt form/ stereochemistry/ melting point |
|---|---|---|---|---|---|---|
| 203 | B8a | H | H | Cl | 3-$CH_3$-2-thienyl | 161° C. |
| 204 | B8a | H | H | Cl | 3-(NH—$SO_2$)-phenyl | $H_2O$ (1:1)/ 196° C. |
| 205 | B8a | H | H | Cl | 3-($CH_3$—$SO_2$)-phenyl | 185° C. |
| 206 | B8a | $CH_3$ | H | Cl | phenyl | 180° C. |
| 207 | B8a | H | H | Cl | 3-$CH_3$-2-furanyl | 188° C. |
| 208 | B30b | H | H | Cl | 3-($CH_3$—$SO_2$—NH)-phenyl | >250° C. |
| 209 | B8a | H | H | Cl | 2-($CH_3$—$SO_2$) | 230° C. |
| 210 | B8a | H | H | Cl | 2-nitrophenyl | 180° C. |
| 211 | B30a | H | H | Cl | 2-aminophenyl | |
| 212 | B30b | H | H | Cl | 2-($CH_3$—CO—O—$CH_2$—CO—NH)-phenyl | |
| 213 | B26 | H | H | Cl | 2-(HO—$CH_2$—CO—NH)-phenyl | 235° C. |
| 214 | B30b | H | H | Cl | 3-($CH_3$—CO—O—$CH_2$—CO—NH)-phenyl | |
| 215 | B26 | H | H | Cl | 3-(HO—$CH_2$—CO—NH)-phenyl | >250° C. |
| 216 | B8a | H | H | Cl | 2-$CH_3$-3-nitrophenyl | |
| 217 | B30a | H | H | Cl | 3-amino-2-methylphenyl | |
| 218 | B30b | H | H | Cl | 2-$CH_3$-3-($NH_2$—$SO_2$—NH)-phenyl | 180° C. |
| 219 | B30b | H | H | Cl | 3-($C_2H_5$—O—CO—CO—NH)-phenyl | $H_2O$ (1:1)/ 208° C. |
| 220 | B29b | H | H | Cl | 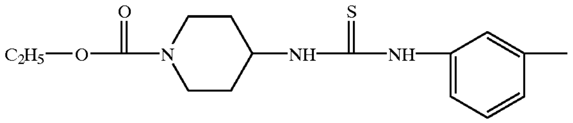 | 180° C. |
| 221 | B30b | H | H | Cl | 3-($NH_2$—$SO_2$—NH)-phenyl | $H_2O$ (1:1)/ 220° C. |
| 222 | B8a | H | H | Cl | 2-$CH_3$-3-pyridinyl | 160° C. |
| 223 | B30b | H | H | Cl | 2-$CH_3$-3-($CH_3$—CO—O—$CH_2$—CO—NH)-phenyl | 206° C. |

TABLE 3

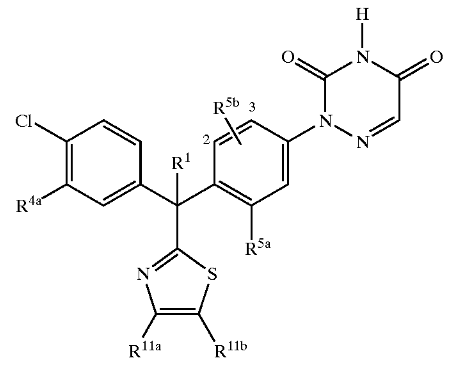

| Co. No. | Ex. No. | $R^1$ | $R^{4a}$ | $R^{5a}$ | $R^{5b}$ | $R^{11a}$ | $R^{11b}$ | Salt from stereochem/ mp. |
|---|---|---|---|---|---|---|---|---|
| 1 | B16 | $CH_3O$ | H | Cl | H | phenyl | H | 126° C. |
| 2 | B14 | H | H | Cl | H | H | H | |
| 3 | B14 | $CH_3$ | H | Cl | H | H | H | |
| 4 | B13a | H | H | Cl | H | phenyl | H | |
| 5 | B13a | H | H | Cl | H | 4-pyridinyl | H | HBr (1:1)/ $H_2O$ (1:1) |
| 6 | B13a | H | H | Cl | 2-Cl | phenyl | phenyl | |
| 7 | B13a | H | H | Cl | 2-Cl | phenyl | $CH_3$ | |
| 8 | B13a | $CH_3$ | H | Cl | 2-Cl | phenyl | H | 110° C. |
| 9 | B13a | H | H | Cl | 2-Cl | 4-Cl-phenyl | H | |
| 10 | B13a | H | H | Cl | H | $CH_3$ | H | |
| 11 | B13a | H | H | Cl | H | phenyl | phenyl | |
| 12 | B13a | $CH_3$ | H | Cl | H | phenyl | H | |
| 13 | B13a | H | H | Cl | H | 4-Cl-phenyl | H | |
| 14 | B13a | H | H | Cl | 2-Cl | $CH_3$ | H | |
| 15 | B13a | H | H | Cl | 2-Cl | 4-pyridinyl | H | |
| 16 | B13a | H | H | Cl | 2-Cl | $CH_3$ | $CH_3$ | |
| 17 | B13a | H | H | Cl | 2-Cl | 4-[$N(C_2H_5)$]-phenyl | H | |
| 18 | B13a | $CH_3$ | H | Cl | 2-Cl | phenyl | phenyl | |
| 19 | B13a | H | H | Cl | 2-Cl | 3-Cl-phenyl | H | 148° C. |
| 20 | B13a | H | H | Cl | 2-Cl | 3-$CF_3$-phenyl | H | 155° C. |
| 21 | B13a | H | H | Cl | 2-Cl | 3-F-phenyl | H | 167° C. |
| 22 | B13a | H | H | Cl | 2-Cl | 3-$CH_3$-phenyl | H | 162° C. |
| 23 | B13a | $CH_3$ | $CF_3$ | Cl | 2-Cl | phenyl | H | 130° C. |
| 24 | B13a | H | H | Cl | 2-Cl | 3-$OCH_3$-phenyl | H | 130° C. |
| 25 | B13a | H | H | Cl | 2-Cl | 2-Br-5-$OCH_3$-phenyl | H | 130° C. |
| 26 | B13a | H | H | Cl | 2-Cl | 4-OH-phenyl | H | 255° C. |

TABLE 3-continued

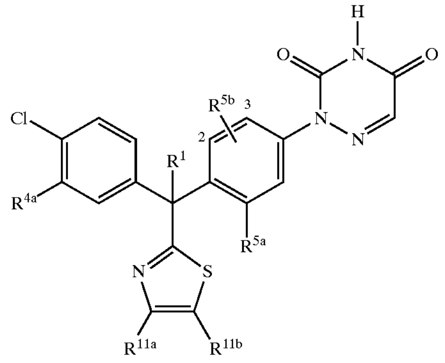

| Co. No. | Ex. No. | $R^1$ | $R^{4a}$ | $R^{5a}$ | $R^{5b}$ | $R^{11a}$ | $R^{11b}$ | Salt from stereochem/ mp. |
|---|---|---|---|---|---|---|---|---|
| 27 | B13a | H | H | Cl | 2-Cl | $C_2H_5O—CO—$ | H | 220° C. |
| 28 | B13a | H | H | Cl | 2-Cl | 3,4-diCl-phenyl | H | 170° C. |
| 29 | B13a | H | H | Cl | 2-Cl | phenyl | $C_2H_5O—CO—$ | 144° C. |
| 30 | B13a | H | H | Cl | 2-Cl | 4-phenyl-phenyl | H | 205° C. |
| 31 | B13a | H | H | Cl | 2-Cl | 2-thienyl | H | 164° C. |
| 32 | B13a | H | H | Cl | 2-Cl | 2-Cl-phenyl | H | 110° C. |
| 33 | B4a | OH | H | Cl | H | H | H | |
| 34 | B4a | OH | H | Cl | H | phenyl | H | 141° C. |
| 35 | B17b | $NH_2$ | H | Cl | H | H | H | |
| 36 | N17b | Cl | H | Cl | H | H | H | |
| 37 | B16 | $CH_3O$ | H | Cl | H | H | H | |
| 38 | B13a | H | H | Cl | 2-Cl | phenyl | H | |
| 39 | B14 | H | H | Cl | 2-Cl | H | H | |
| 224 | B13a | H | H | Cl | 2-Cl | phenyl | ethyl | 260° C. |
| 225 | B13a | H | H | Cl | 2-Cl | phenyl-$CH_2$— | H | 135° C. |
| 226 | B13a | H | $CF_3$ | Cl | 2-Cl | phenyl | H | 175° C. |
| 227 | B13a | $CH_3$ | Cl | Cl | 2-Cl | phenyl | H | 120° C. |
| 228 | B13a | $CH_3$ | Cl | Cl | 2-Cl | phenyl | phenyl | 130° C. |
| 229 | B13a | H | H | Cl | 2-Cl | 4-piperidinyl | H | HCl (1:1)/ 200–210° C. |
| 230 | B25 | H | H | Cl | 2-Cl | 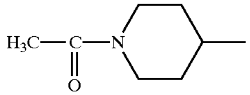 | H | 212° C. |
| 231 | B13a | H | H | Cl | 2-Cl | $Cl—CH_2—$ | H | |

TABLE 3-continued

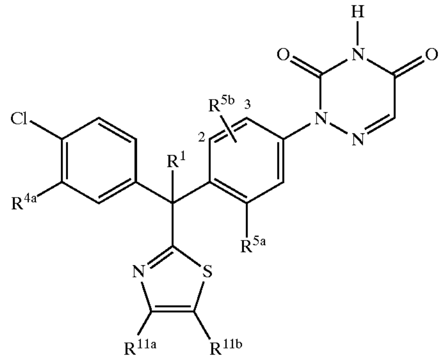

| Co. No. | Ex. No. | $R^1$ | $R^{4a}$ | $R^{5a}$ | $R^{5b}$ | $R^{11a}$ | $R^{11b}$ | Salt from stereochem/ mp. |
|---|---|---|---|---|---|---|---|---|
| 232 | B24c | H | H | Cl | 2-Cl | 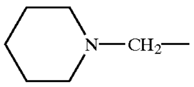 | H | 175° C. |
| 233 | B13a | $CH_3$ | Cl | Cl | 2-Cl | phenyl | $CH_3$ | 130° C. |
| 234 | B13a | $CH_3$ | $CF_3$ | Cl | 2-Cl | phenyl | $CH_3$ | 110° C. |
| 235 | B13a | $CH_3$ | $CF_3$ | Cl | 3-$CH_3$ | phenyl | H | 188° C. |
| 236 | B13a | H | H | Cl | 2-Cl | 2-furanyl | H | 126° C. |
| 237 | B13a | $CH_3$ | $CF_3$ | Cl | 2-Cl | phenyl | phenyl | 120° C. |
| 238 | B13a | $CH_3$ | $CF_3$ | Cl | 3-$CH_3$ | phenyl | $CH_3$ | 130° C. |
| 239 | B13a | $CH_3$ | $CF_3$ | Cl | H | phenyl | H | 126° C. |
| 240 | B24c | H | H | Cl | 2-Cl | $(CH_3)_2N—CH_2—$ | H | 226° C. |
| 241 | B13b | H | H | Cl | 2-Cl | phenyl | $(CH_3)_2CH—$ | 250° C. |
| 242 | B13a | H | H | Cl | 2-Cl | 2-F-phenyl | H | 85° C. |
| 243 | B13a | H | H | Cl | 2-Cl | 2-$CH_3$-phenyl | H | 92° C. |
| 244 | B13a | H | H | Cl | 2-Cl | 2-Br-phenyl | H | 90° C. |
| 245 | B13a | H | H | Cl | 2-Cl | phenyl | propyl | 246° C. |
| 246 | B13a | H | $CF_3$ | Cl | 2-Cl | phenyl | $CH_3$ | 180° C. |
| 247 | B13a | $CH_3$ | $CH_3$ | Cl | H | phenyl | H | 150° C. |
| 248 | B13a | H | H | Cl | 2-Cl | $CH_3$ | phenyl | 146° C. |
| 249 | B13a | H | H | Cl | 2-Cl | phenyl | phenyl-$CH_2$— | 176° C. |
| 250 | B13a | H | H | Cl | 2-Cl | 3-Br-phenyl | H | 116° C. |
| 251 | B13a | $CH_3$ | Cl | Cl | 2-Cl | phenyl | ethyl | 132° C. |
| 252 | B13a | H | H | Cl | 2-Cl | 2,3-diCl-phenyl | H | 98° C. |
| 253 | B13a | H | H | Cl | 2-Cl | phenyl | $(CH_3)_2N—CH_2—$ | 228° C. |
| 254 | B13a | H | $CF_3$ | Cl | 2-Cl | 2-Cl-phenyl | H | 104° C. |
| 255 | B13a | $CH_3$ | $CF_3$ | H | 2-$OCH_3$ | phenyl | H | 89° C. |
| 256 | B13a | H | H | Cl | 2-Cl | phenyl | $C_2H_5O—CO—CH_2—$ | 170° C. |
| 257 | B13a | H | H | Cl | 2-Cl | 2,5-diCl-phenyl | H | 130° C. |

TABLE 3-continued

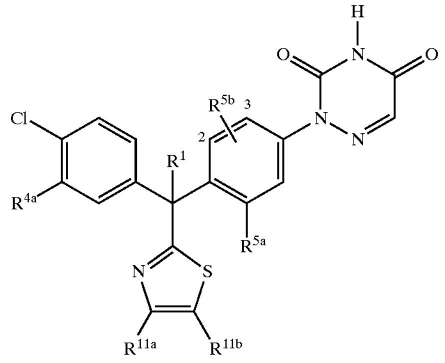

| Co. No. | Ex. No. | $R^1$ | $R^{4a}$ | $R^{5a}$ | $R^{5b}$ | $R^{11a}$ | $R^{11b}$ | Salt from stereochem/ mp. |
|---|---|---|---|---|---|---|---|---|
| 258 | B13a | H | H | Cl | 2-Cl | 3-F-phenyl | $CH_3$ | 202° C. |
| 259 | B13a | H | H | Cl | 2-Cl | 2-F- phenyl | $CH_3$ | 178° C. |
| 260 | B13a | H | H | Cl | 2-Cl | 3-F-phenyl | ethyl | 255° C. |
| 261 | B13a | H | H | Cl | 2-Cl | 2-F-phenyl | ethyl | 152° C. |
| 262 | B13a | H | H | Cl | Cl | 2-Cl-phenyl | ethyl | 180° C. |
| 263 | B13a | H | H | Cl | 2-Cl | 2-$CH_3O$-phenyl | H | 120° C. |
| 264 | B13a | H | H | Cl | 2-Cl | 2,6-diCl-phenyl | H | 200° C. |
| 265 | B17a | Cl | H | Cl | H | phenyl | Cl | |
| 266 | B3f | $(CH_3)_2N—(CH_2)_2—NH—$ | H | Cl | H | phenyl | Cl | 168° C. |
| 267 | B13a | H | H | Cl | 2-Cl | H | phenyl | 175° C. |
| 268 | B13a | H | H | Cl | 2-Cl | 2,6-diF-phenyl | $CH_3$ | 170° C. |
| 269 | B13a | H | $CH_3$ | Cl | 2-Cl | phenyl | H | 126° C. |
| 270 | B13a | H | Cl | $CH_3$ | 2-$CH_3$ | phenyl | H | 181° C. |
| 271 | B13a | H | Cl | $CH_3$ | 2-$CH_3$ | phenyl | $CH_3$ | 140° C. |
| 272 | B13a | H | H | Cl | 2-Cl | 2-Cl-phenyl | $CH_3$ | 182° C. |
| 273 | B13a | H | H | Cl | 2-Cl | phenyl | phenyl-CO— | 148° C. |
| 274 | B13a | H | H | Cl | 2-Cl | 2-Cl-phenyl | $C_2H_5O—CO—$ | 232° C. |
| 275 | B13a | H | H | Cl | 2-Cl | phenyl | $(CH_3)_2N—CO—CH_2—$ | 216° C. |
| 276 | B13a | H | H | Cl | 2-Cl | phenyl | 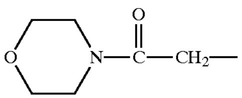 | 203° C. |
| 277 | B13a | H | H | Cl | 2-Cl | phenyl | $C_2H_5O—CO—(CH_3)_2—$ | 184° C. |
| 278 | B13c | H | H | Cl | 2-Cl | phenyl | $CH_3O—CH_2—$ | 228° C. |
| 279 | B13a | H | H | Cl | 2-Cl | phenyl | $(CH_3)_2N—(CH_2)_2—$ | 229° C. |
| 280 | B13a | H | H | Cl | 2-Cl | 3-F-phenyl | $(CH_3)_2N—CH_2—$ | 219° C. |

TABLE 3-continued

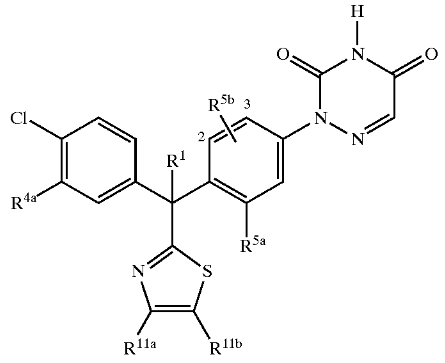

| Co. No. | Ex. No. | $R^1$ | $R^{4a}$ | $R^{5a}$ | $R^{5b}$ | $R^{11a}$ | $R^{11b}$ | Salt from stereochem/ mp. |
|---|---|---|---|---|---|---|---|---|
| 281 | B13a | H | H | Cl | 2-Cl | phenyl | $(CH_3)_2N—CO—(CH_2)_2—$ | 204° C. |
| 282 | B24a | H | H | Cl | 2-Cl | phenyl | $HO—CH_2—$ | 142° C. |
| 283 | B13a | H | H | Cl | 2-Cl | phenyl | 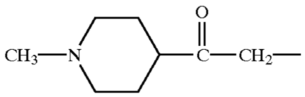 | 160° C. |
| 284 | B13a | H | H | Cl | 2-Cl | phenyl | cyclohexyl | 250° C. |
| 285 | B13a | H | H | Cl | 2-Cl | 2-F-phenyl | $C_2H_5O—CO—$ | 222° C. |
| 286 | B13a | H | H | Cl | 2-Cl | 3,5-diF-phenyl | H | 95° C. |
| 287 | B13a | H | H | Cl | 2-Cl | 3-F-phenyl | $CH_3$ | 95° C. |
| 288 | B13a | $CH_3$ | F | Cl | 2-Cl | phenyl | H | 100° C. |
| 289 | B13a | H | $OCH_3$ | Cl | 2-Cl | phenyl | H | 158° C. |
| 290 | B13a | H | H | Cl | 2-Cl | 2,5-diF-phenyl | H | 120° C. |
| 291 | B24b | H | H | Cl | 2-Cl | phenyl | $Cl—CH_2—$ | |
| 292 | B24c | H | H | Cl | 2-Cl | phenyl | 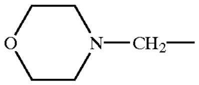 | 105° C. |
| 293 | B13a | H | H | Cl | 2-Cl | 2-Cl-phenyl | $C_2H_5O—CO—CH_2—$ | 174° C. |
| 294 | B13a | H | H | Cl | 2-Cl | 4-Br-phenyl | H | |
| 295 | B13c | H | H | Cl | 2-Cl | phenyl | $C_2H_5—O—CH_2—$ | 210° C. |
| 296 | B24c | H | H | Cl | 2-Cl | phenyl | $CH_3—NH—CH_2—$ | HCl (1:1); $H_2O$ (1:3)/ 205° C. |
| 297 | B13a | H | H | Cl | 2-Cl | phenyl | phenyl-$CH_2—N(CH_3)—CH_2—$ | 210° C. |

TABLE 3-continued
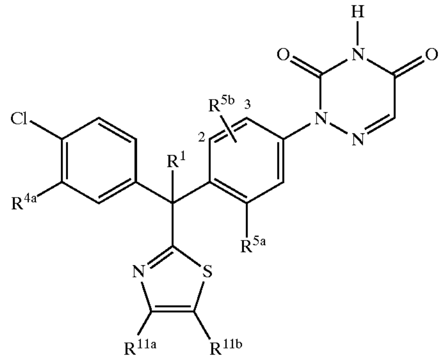
| Co. No. | Ex. No. | $R^1$ | $R^{4a}$ | $R^{5a}$ | $R^{5b}$ | $R^{11a}$ | $R^{11b}$ | Salt from stereochem/ mp. |
|---|---|---|---|---|---|---|---|---|
| 298 | B13c | H | H | Cl | 2-Cl | phenyl | $(CH_3)_3C—O—CO—$ | |
| 299 | B22a | H | H | Cl | 2-Cl | phenyl | HOOC— | 206° C. |
| 300 | B13a | H | H | Cl | 2-Cl | phenyl | $HOOC—CH_2—$ | 186° C. |
| 301 | B13c | H | H | Cl | 2-Cl | phenyl | $CH_3—NH—CO—CH_2—$ | 158° C. |
| 302 | B24c | H | H | Cl | 2-Cl | phenyl | 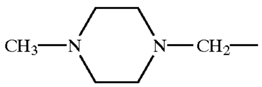 | 186° C. |
| 303 | B22b | H | H | Cl | 2-Cl | phenyl | $(CH_3)_2N—CO—$ | 150° C. |
| 304 | B22b | H | H | Cl | 2-Cl | phenyl | 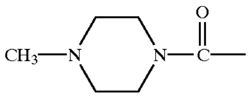 | 170° C. |
| 305 | B22b | H | H | Cl | 2-Cl | phenyl | 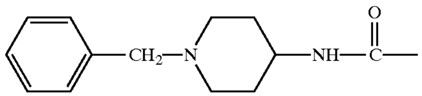 | 210° C. |
| 306 | B22b | H | H | Cl | 2-Cl | phenyl | 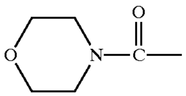 | 156° C. |
| 307 | B22b | H | H | Cl | 2-Cl | phenyl | $CH_3O—(CH_2)_2—NH—CO—$ | 248° C. |

TABLE 3-continued

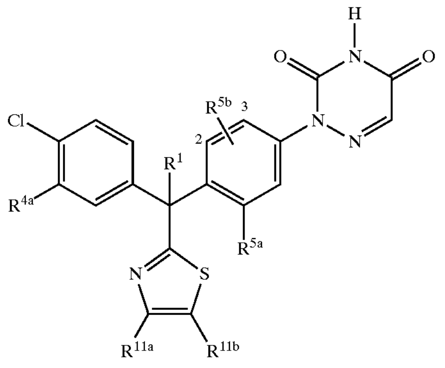

| Co. No. | Ex. No. | $R^1$ | $R^{4a}$ | $R^{5a}$ | $R^{5b}$ | $R^{11a}$ | $R^{11b}$ | Salt from stereochem/ mp. |
|---|---|---|---|---|---|---|---|---|
| 308 | B13a | H | H | Cl | 2-Cl | phenyl | $Cl—(CH_2)_2—$ | |
| 309 | B24c | H | H | Cl | 2-Cl | phenyl | 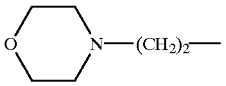 | trifluoro acetate (1:1) |
| 310 | B13c | H | H | Cl | 2-Cl | phenyl | $c.C_6H_{11}—O—CH_2—$ | 200° C. |
| 311 | B24c | H | H | Cl | 2-Cl | phenyl | $(CH_3)_2N—(CH_2)_2—N(CH_3)—CH_2—$ | 170° C. |
| 312 | B22b | H | H | Cl | 2-Cl | phenyl | $(CH_3)_2N—(CH_2)_2—NH—CO—$ | $H_2O$ (1:1)/ 160° C. |
| 313 | B24c | H | H | Cl | 2-Cl | phenyl | 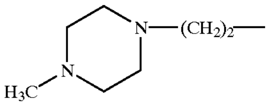 | $H_2O$ (1:1)/ 216° C. |
| 314 | B24c | H | H | Cl | 2-Cl | phenyl | 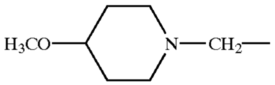 | HCl (1:1)/$H_2O$ (1:1)/190° C. |
| 315 | B24c | H | H | Cl | 2-Cl | phenyl | $CH_3O—CH(CH_3)—$ | >260° C. |
| 316 | B24c | H | H | Cl | 2-Cl | phenyl | $CH_3O—(CH_2)_2—NH—CH_2—$ | 110° C. |
| 317 | B22b | H | H | Cl | 2-Cl | phenyl | $(CH_3)_2N—(CH_2)_2—NH—CO—CH_2—$ | 156° C. |
| 318 | B13a | H | H | Cl | 2-Cl | 3-F-phenyl | H | (A)/120° C. |
| 319 | B13a | H | H | Cl | 2-Cl | 3-F-phenyl | H | (B)/120° C. |
| 320 | B22b | H | H | Cl | 2-Cl | phenyl | $CH_3O—(CH_2)_2—NH—CO—CH_2—$ | 170–172° C. |

TABLE 3-continued
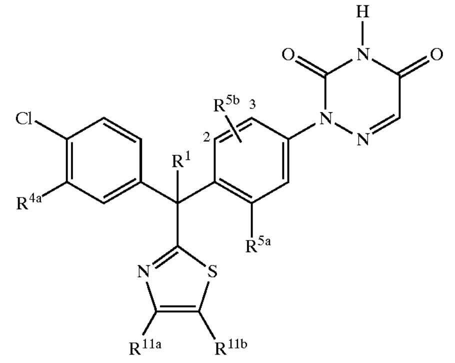
| Co. No. | Ex. No. | $R^1$ | $R^{4a}$ | $R^{5a}$ | $R^{5b}$ | $R^{11a}$ | $R^{11b}$ | Salt from stereochem/ mp. |
|---|---|---|---|---|---|---|---|---|
| 321 | B24c | H | H | Cl | 2-Cl | phenyl | 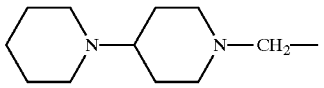 | 210° C. |
| 322 | B24c | H | H | Cl | 2-Cl | phenyl | 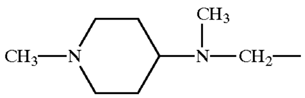 | 168° C. |
| 323 | B24a | H | H | Cl | 2-Cl | 2-F-phenyl | $HO—CH_2—$ | |
| 324 | B24b | H | H | Cl | 2-Cl | 2-F-phenyl | $Cl—CH_2—$ | |
| 325 | B24c | H | H | Cl | 2-CL | 2-F-phenyl | $(CH_3)_2N—CH_2—$ | 250° C. |
| 326 | B22b | H | H | Cl | 2-Cl | phenyl | 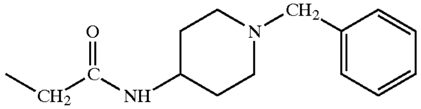 | 140° C. |
| 327 | B24c | H | H | Cl | 2-Cl | phenyl | 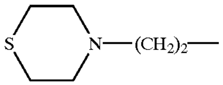 | 170° C. |

TABLE 3-continued

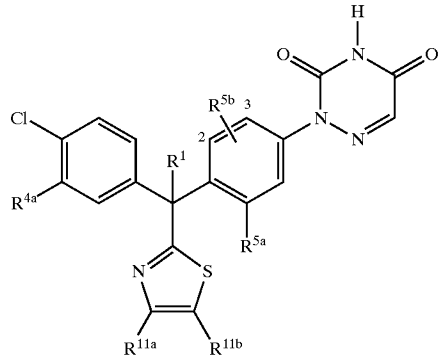

| Co. No. | Ex. No. | $R^1$ | $R^{4a}$ | $R^{5a}$ | $R^{5b}$ | $R^{11a}$ | $R^{11b}$ | Salt from stereochem/ mp. |
|---|---|---|---|---|---|---|---|---|
| 328 | B13a | H | H | Cl | 2-Cl | phenyl | 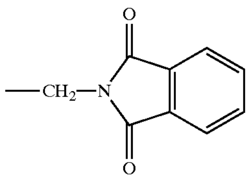 | |
| 329 | B29a | H | H | Cl | 2-Cl | phenyl | $NH_2$—$CH_2$— | $H_2O$ (1:1)/ 170° C. |
| 330 | B13a | H | H | Br | 2-Br | phenyl | $CH_3$ | 228° C. |
| 331 | B29b | H | H | Cl | 2-Cl | phenyl | phenyl-NH—C(=S)—NH—$CH_2$— | 159° C. |
| 332 | B24c | H | H | Cl | 2-Cl | phenyl | phenyl-$(CH_2)_2$—N($CH_3$)—$CH_2$— | 187° C. |
| 333 | B29b | H | H | Cl | 2-Cl | phenyl | (4-Cl-phenyl)-NH—CO—NH—$CH_2$— | 202° C. |
| 334 | B24c | H | H | Cl | 2-Cl | phenyl | c.$C_6H_{11}$—N($CH_3$)—$CH_2$— | 176° C. |
| 335 | B13a | H | H | Cl | 2-Cl | phenyl | $(CH_3)_2N$—$(CH_2)_2$—N($CH_3$)—CO—$CH_2$— | 132° C. |
| 336 | B30b | H | H | Cl | 2-Cl | phenyl | phenyl-$CH_2$—$SO_2$—NH—$CH_2$— | 158° C. |
| 337 | B13a | H | H | Cl | 2-Cl | 2,3-diF-phenyl | H | 110° C. |

TABLE 4

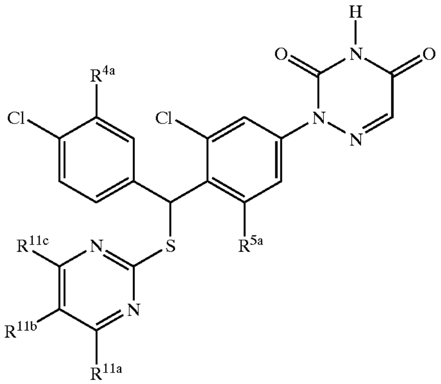

| Co. No. | Ex. No. | $R^{4a}$ | $R^{5a}$ | $R^{11a}$ | $R^{11b}$ | $R^{11c}$ | Salt form/ stereochemistry |
|---|---|---|---|---|---|---|---|
| 338 | B2a | H | H | OH | c.$C_3H_5$—$CH_2$— | $CH_3$ | |
| 339 | B2a | H | H | H | $C_2H_5O$—CO— | OH | |
| 340 | B2a | H | Cl | H | H | H | |
| 341 | B2a | $CF_3$ | Cl | H | H | H | |
| 342 | B2a | $CF_3$ | Cl | phenyl | H | H | |
| 343 | B2a | H | H | H | H | $NH_2$ | |
| 344 | B18 | H | Cl | H | H | 4-morpholinyl | $CH_3SO_3H$ (1:1) $H_2O$ (1:2) |
| 345 | B18 | H | Cl | H | H | 4-$CH_3$-1-piperazinyl | |
| 346 | B8b | H | Cl | H | H | H | (A); $\alpha_{20}^{D}$ = −346.46° (c = 6.35 mg/5 ml in $CH_3OH$) |
| 347 | B8b | H | Cl | H | H | H | (B); $\alpha_{20}^{D}$ = +326.15° (c = 6.73 mg/5 ml in $CH_3OH$) |
| 348 | B18 | H | Cl | $NH_2$ | H | H | |
| 349 | B23 | H | Cl | H | H | 4-morpholinyl | |
| 350 | B18 | H | Cl | H | H | OH | |
| 351 | B18 | H | Cl | H | H | 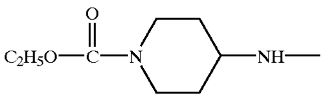 | |
| 352 | B18 | H | Cl | H | H | 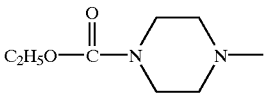 | |
| 353 | B18 | H | Cl | H | H | 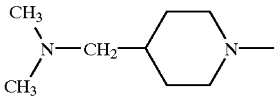 | |
| 354 | B18 | H | Cl | H | H | 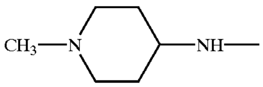 | HCl (1:1); $H_2O$ (1:1) |
| 355 | B18 | H | Cl | $(CH_3)_2$—N— | H | H | |
| 356 | B23a | H | Cl | H | H | $CF_3$—$SO_2$—O— | |
| 357 | B23b | H | Cl | H | H | HO—$(CH_2)_2$—NH— | |
| 358 | B23b | H | Cl | H | H | [HO—$(CH_2)_2]_2$N— | |

TABLE 4-continued

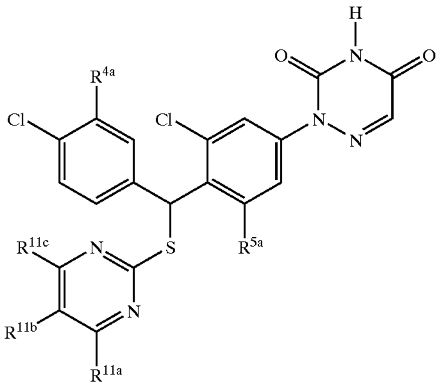

| Co. No. | Ex. No. | $R^{4a}$ | $R^{5a}$ | $R^{11a}$ | $R^{11b}$ | $R^{11c}$ | Salt form/ stereochemistry |
|---|---|---|---|---|---|---|---|
| 359 | B18 | H | Cl | 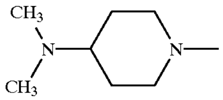 | H | H | $CH_3SO_3H$ (1:1) |
| 360 | B27 | H | Cl | H | H | 1-piperazinyl | $H_2O$ (1:1) |
| 361 | B23 | H | Cl | H | H | $(HO—CH_2)_2CH—NH—$ | |
| 362 | B18 | H | Cl | H | H | 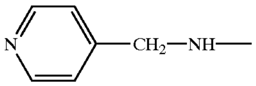 | |

TABLE 5

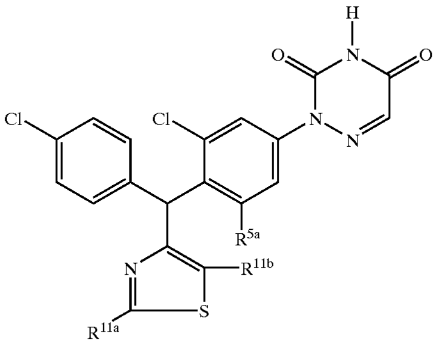

| Co. No. | Ex. No. | $R^{5a}$ | $R^{11a}$ | $R^{11b}$ | Salt form/ stereochemistry |
|---|---|---|---|---|---|
| 363 | B21 | Cl | phenyl | H | |
| 364 | B21 | Cl | 2-F-phenyl | H | |
| 365 | B21 | Cl | phenyl | $CH_3$— | |
| 366 | B21 | Cl | 4-pyridinyl | H | HCl (1:1); $H_2O$ (1:1) |
| 366a | B8a | Cl | 4-pyridinyl | H | HCl (1:1); $H_2O$ (1:1); (A) |
| 366b | B8a | Cl | 4-pyridinyl | H | HCl (1:1); $H_2O$ (1:1); (B) |
| 367 | B21 | Cl | 2-Cl-phenyl | H | |
| 368 | B21 | Cl | 3-F-phenyl | H | |
| 369 | B21 | H | $CH_3$ | phenyl | |
| 370 | B21 | Cl | 3-F-phenyl | $CH_3$— | |

TABLE 5-continued

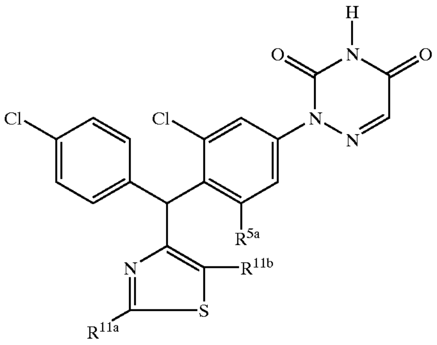

| Co. No. | Ex. No. | $R^{5a}$ | $R^{11a}$ | $R^{11b}$ | Salt form/ stereochemistry |
|---|---|---|---|---|---|
| 371 | B21 | Cl | 3-Cl-phenyl | H | |
| 372 | B21 | Cl | 3-$CH_3$-phenyl | H | |
| 373 | B21 | H | phenyl | phenyl | |
| 374 | B21 | Cl | 2-$CH_3$-phenyl | H | |
| 375 | B21 | Cl | 3-pyridinyl | H | |

TABLE 6

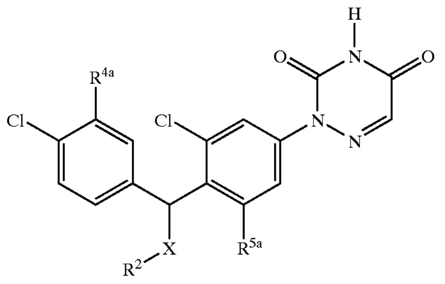

| Co. No. | Ex. No. | X | $R^2$ | $R^{4a}$ | $R^{5a}$ | salt form/ stereochemistry melting point |
|---|---|---|---|---|---|---|
| 52 | B2a | S | 1H-benzimidazol-2-yl | H | H | |
| 53 | B2a | S | 4-$CH_3$-1,2,4-triazol-3-yl | H | H | |
| 54 | B2a | S | $(CH_3)_2N—(CH_2)_2—$ | H | H | |
| 55 | B2az | S | 1H-1,2,4-triazol-3-yl | H | H | |
| 56 | B2a | S | 5-$CH_3$-1,3,4-thiadiazol-2-yl | H | H | |
| 57 | B2a | S | 4-F-phenyl | H | H | |
| 58 | B2a | S | 1-$CH_3$-2-imidazolyl | H | H | |
| 59 | B2a | S | 4-aminophenyl | H | H | |
| 60 | B2a | S | 4-OH-6-$CH_3$-2-pyrimidinyl | H | H | |
| 61 | B2a | S | 4-OH-2-pyrimidinyl | H | H | $H_2O$ (1:1) |
| 62 | B2a | S | 5-$CH_3$-1H-benzimidazol-2-yl | H | H | |
| 63 | B2a | S | 2-thiazolyl | H | H | |
| 64 | B2a | S | 2-furanyl-$CH_2$— | H | H | |
| 65 | B2a | S | 4-pyridinyl | H | H | |
| 66 | B2a | S | 4,6-di$CH_3$-2-pyrimidinyl | H | H | |
| 67 | B2a | S | 4-Cl-phenyl-$CH_2$— | H | H | |
| 68 | B2a | S | 2,4-diamino-6-pyrimidinyl | H | H | |
| 69 | B2a | S | 1H-purin-6-yl | H | H | |
| 70 | B2a | S | 4,6-diamino-2-pyrimidinyl | H | H | |
| 71 | B2a | S | 2-benzoxazolyl | H | H | |
| 72 | B2a | S | 4-OH-6-propyl-2-pyrimidinyl | H | H | |
| 73 | B2a | S | 2-pyridinyl, N-oxide | H | H | |
| 74 | B2a | S | 1H-pyrazolo[3,4-d]pyrimidin-4-yl | H | H | |
| 75 | B2a | S | 4-$HC_3$-2-pyrimidinyl | H | H | |
| 76 | B2a | S | $C_2H_5—O—C(=O)—CH_2—$ | H | H | |
| 77 | B2a | S | 2-benzothiazolyl | H | H | |
| 78 | B2a | S | 4,5-dihydro-2-thiazolyl | H | H | |
| 79 | B2a | S | 4-(4-$OCH_3$-phenyl)-2-pyrimidinyl | H | H | |
| 80 | B2a | S | $CH_3—O—C(=O)—(CH_2)_2—$ | H | H | |
| 81 | B2a | S | thiazolo[5,4-b]pyridin-2-yl | H | H | |
| 82 | B2a | S | 4-OH-6-($CH_3OCH_2$)-2-pyrimidinyl | H | H | |
| 83 | B2a | S | 2-amino-1H-purin-4-yl | H | H | |
| 84 | B2a | S | 4-(2-thienyl)-2-pyrimidinyl | H | H | |
| 85 | B2a | S | 6-$CH_3$-5-oxo-4H-1,2,4-triazin-3-yl | H | H | |
| 86 | B2a | S | 2-pyridinyl | $CF_3$ | H | |
| 87 | B2a | S | 4-amino-6-OH-2-pyrimidinyl | H | H | |
| 88 | B2a | S | 5-$CF_3$-2-pyridinyl | H | H | |
| 89 | B2a | S | 5-$CF_3$-4H-1,2,4-triazol-3-yl | H | H | |
| 90 | B2a | S | cyclohexyl | H | H | |
| 91 | B2a | S | 5-ethyl-4-oxo-2(3H)-pyrimidinyl | H | H | |
| 92 | B1b | S | 2-pyrimidinyl | H | H | |
| 93 | B2a | S | 2-pyridinyl | H | H | |
| 94 | B2b | S | 1H-imidazol-2-yl | H | H | |
| 95 | B2c | S | $C_2H_5—O—C(=O)—CH(NH_2)—$ | H | H | |
| 96 | B11 | S | 2,4-di$OCH_2$-6-pyrimidinyl | H | H | |
| 98 | B1 | O | $CH_3$ | H | H | |
| 133 | B1 | O | $(CH_3)_2CH—CH_2$ | H | H | |
| 376 | B2a | S | thiazolo[5,4-b]pyridin-2-yl | H | Cl | |
| 377 | B2a | S | 2-pyridinyl | H | Cl | |
| 377a | B8a | S | 2-pyridinyl | H | Cl | (A); $\alpha_{20}^{D}$ = +354.70° (c = 5.85 mg/5 ml in $CH_3OH$) |
| 377b | B8a | S | 2-pyridinyl | H | Cl | (B); $\alpha_{20}^{D}$ = −356.73° (c = 6.91 mg/5 ml in $CH_3OH$) |
| 378 | B2a | S | 2-pyridinyl | $CF_3$ | Cl | |
| 379 | B2a | S | 2-benzoxazolyl | $CF_3$ | Cl | |
| 380 | B2a | S | 4-phenyl-2-thiazolyl | H | Cl | |

TABLE 6-continued

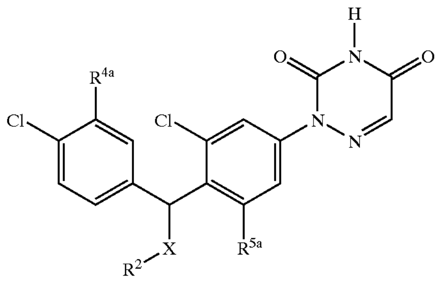

| Co. No. | Ex. No. | X | $R^2$ | $R^{4a}$ | $R^{5a}$ | salt form/ stereochemistry melting point |
|---|---|---|---|---|---|---|
| 381 | B2a | S | 4-phenyl-2-thiazolyl | $CF_3$ | Cl | |
| 382 | B2a | S | thiazolo[5,4-b]pyridin-2-yl | $CF_3$ | Cl | |
| 383 | B2a | S | 2-benzoxazolyl | H | Cl | |
| 384 | B2a | S | 2-benzothiazolyl | H | Cl | |
| 385 | B2a | S | 2-benzothiazolyl | $CF_3$ | Cl | |
| 386 | B2a | S | 4,5-dihydro-2-thiazolyl | $CF_3$ | Cl | |
| 387 | B2a | S | 4-thiazolyl | $CF_3$ | Cl | |
| 388 | B2a | S | 6-nitro-2-benzothiazolyl | $CF_3$ | Cl | |
| 389 | B2a | S | 6-$NH_2$-2-benzothiazolyl | $CF_3$ | Cl | |
| 390 | B2a | S | 4-(2-thienyl)-2-thiazolyl | $CF_3$ | Cl | |
| 391 | B2a | S | 5-phenyl-1,3,4-oxadiazol-2-yl | $CF_3$ | Cl | |
| 392 | B2a | S | 5$CH_3$-4-phenyl-2-thiazolyl | $CF_3$ | Cl | |
| 393 | B2a | S | 4-$NH_2$-phenyl | $CF_3$ | Cl | |
| 394 | B2a | S | 6-ethoxy-2-benzothiazolyl | $CF_3$ | Cl | |
| 395 | B2a | S | pyrido[3,4-d]thiazol-2-yl | $CF_3$ | Cl | |
| 396 | B2a | S | 1H-benzimidazol-2-yl | $CF_3$ | Cl | |
| 397 | B2a | S | 4-(2,4-diF-phenyl)-2-thiazolyl | $CF_3$ | Cl | |
| 398 | B2a | S | 4-($CH_3$—CO—NH)-phenyl | $CF_3$ | Cl | |
| 399 | B2a | S | 4-(2-furanyl)-2-thiazolyl | $CF_3$ | Cl | |
| 400 | B2d | S | 1,3-dihydro-4-phenyl-2H-imidazole-2-thion-5-yl | $CF_3$ | Cl | |
| 401 | B2a | S | 2-pyrazinyl | $CF_3$ | Cl | |
| 402 | B2a | S | 5-Cl-2-benzothiazolyl | $CF_3$ | Cl | |
| 403 | B2a | S | pyrido[3,4-d]oxazol-2-yl | $CF_3$ | Cl | |
| 404 | B2a | S | 3-phenyl-1,2,4-oxadiazol-5-yl | $CF_3$ | Cl | |
| 405 | B2a | S | 5-$CH_3$-4-phenyl-2-thiazolyl | $CF_3$ | Cl | |
| 406 | B18 | S | 5-phenyl-1,3,4-oxadiazol-2-yl | H | Cl | |
| 407 | B2a | S | (2-pyrazinyl)-$CH_2$— | H | Cl | 216° C. |
| 408 | B18 | S | 3-phenyl-1,2,4-oxadiazol-5-yl | H | Cl | |
| 409 | B18 | S | 4-pyrimidinyl | H | Cl | |

TABLE 7

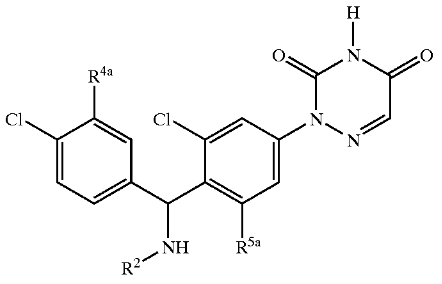

| Co. No. | Ex. No. | $R^2$ | $R^{4a}$ | $R^{5a}$ | salt form |
|---|---|---|---|---|---|
| 40 | B3e | 5-$CH_3$-3-isoxazol | H | H | |
| 41 | B3c | $CH_3$—O—$(CH_2)_2$— | H | H | |
| 42 | B3c | 4-$CH_3$-6-$OCH_3$-2-pyrimidinyl | H | H | |
| 43 | B3c | 2-furanylethyl | H | H | HCl (1:1) |
| 44 | B3c | 2-thiazolyl | H | H | |
| 46 | B3a | cyclohexyl | H | H | |
| 47 | B10b | benzoyl | H | H | |

TABLE 7-continued

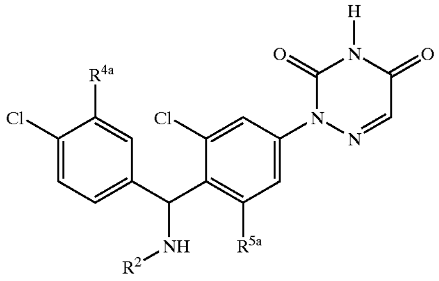

| Co. No. | Ex. No. | $R^2$ | $R^{4a}$ | $R^{5a}$ | salt form |
|---|---|---|---|---|---|
| 48 | B3f | 1-$CH_3$-4-piperidinyl | H | H | |
| 49 | B3e | 2-pyrimidinyl | H | H | |
| 50 | B3d | 1H-imidazol-2-yl | H | H | |
| 51 | B3c | $C_2H_4OH$ | H | H | |
| 410 | B10b | thiazolo[5,4-b]pyridin-2-yl | H | H | |
| 411 | B3g | 4-phenyl-2-thiazolyl | $CF_3$ | Cl | |

TABLE 7-continued

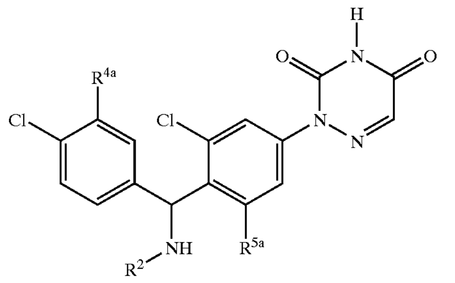

| Co. No. | Ex. No. | $R^2$ | $R^{4a}$ | $R^{5a}$ | salt form |
|---|---|---|---|---|---|
| 412 | B3c | 5-$CH_3$-4-phenyl-2-thiazolyl | H | H | |
| 413 | B3g | 2-pyrimidinyl | H | Cl | |

TABLE 8

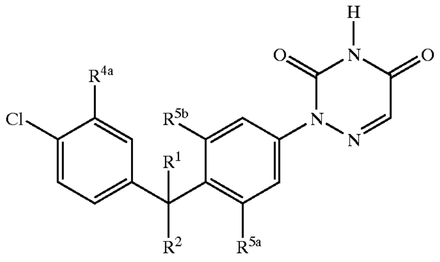

| Co. No. | Ex. No. | $R^1$ | $R^2$ | $R^{4a}$ | $R^{5a}$ | $R^{5b}$ | Salt form melting point |
|---|---|---|---|---|---|---|---|
| 45 | B3a | H | $N(CH_3)_2$ | H | Cl | H | |
| 97 | B3c | H | 1,2,4-triazol-1-yl | H | Cl | H | |
| 99 | B3c | H | 1,2,4-triazol-4-yl | H | Cl | H | |
| 100 | B3c | H | 1H-imidazolyl-1-yl | H | Cl | H | |
| 101 | B8a | H | 5-phenyl-1,3,4-oxadiazol-2-yl | H | Cl | H | |
| 102 | B8a | H | 5-$CH_3$-1,3,4-oxadiazol-2-yl | H | Cl | H | |
| 103 | B8a | H | 5-phenyl-2-oxazolyl | H | Cl | H | |
| 104 | B8a | $CH_3$ | 5-phenyl-1,3,4-oxadiazol-2-yl | H | Cl | H | |
| 105 | B8a | H | 5-phenyl-2-oxazolyl | H | Cl | Cl | |
| 106 | B6 | $CH_3$ | 3-phenyl-1,2,4-oxadiazol-5-yl | H | Cl | H | |
| 107 | B7 | H | 5-phenyl-1,2,4-oxadiazol-3-yl | H | Cl | H | |
| 108 | B5a | H | 2-$CH_3$-1,2,4-triazol-3-yl | H | Cl | H | |
| 109 | B5a | H | 1-$CH_3$-2-imidazolyl | H | Cl | Cl | 164° C. |
| 110 | B4a | OH | 2-$CH_3$-1,2,4-triazol-3-yl | H | Cl | H | $H_2O$ (1:1) |
| 111 | B4a | OH | 2-benzothiazolyl | H | Cl | H | |
| 112 | B5a | H | 4-pyridinyl | H | Cl | H | |
| 113 | B5a | H | 4-pyridinyl | H | Cl | Cl | |
| 114 | B5a | H | 2-pyridinyl | H | Cl | H | 130° C. |
| 115 | B5a | H | 2-pyridinyl | H | Cl | Cl | 205° C. |
| 116 | B5a | H | 3-pyridinyl | H | Cl | Cl | 166° C. |
| 117 | B4a | OH | 3-pyridinyl | H | Cl | H | |
| 118 | B3a | H | 4-$CH_3$-1-piperazinyl | H | Cl | H | |
| 119 | B3b | H | 4-OH-1-piperidinyl | H | Cl | H | |
| 120 | B4a | OH | 1-$CH_3$-2-imidazolyl | H | Cl | H | $H_2O$ (1:1) |
| 121 | B4b | OH | 3-$CH_3$-4-imidazolyl | H | Cl | H | $H_2O$ (1:1) |
| 122 | B4c | OH | CN—$CH_2$— | H | Cl | Cl | |
| 123 | B5a | H | 1-$CH_3$-2-imidazolyl | H | Cl | H | |
| 124 | B5b | H | 3-pyridinyl | H | Cl | H | |
| 125 | B6 | H | 3-phenyl-1,2,4-oxazdiazol-5-yl | H | Cl | H | |
| 126 | B7 | H | 5-$CH_3$-1,2,4-oxadiazol-2-yl | H | Cl | H | |
| 127 | B8a | H | 5-phenyl-1,3,4-oxadiazol-2-yl | H | Cl | Cl | |
| 128 | B9 | H | 5-SH-4-phenyl-1,2,4-triazol-3-yl | H | Cl | H | |
| 129 | B9 | H | 5-(phenyl-NH)-1,3,4-thiadiazol- | H | Cl | H | |

TABLE 8-continued

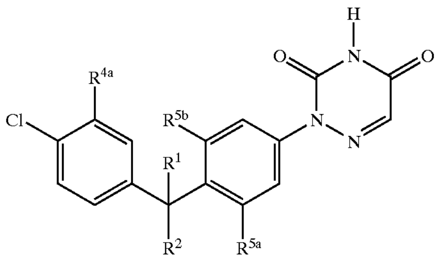

| Co. No. | Ex. No. | $R^1$ | $R^2$ | $R^{4a}$ | $R^{5a}$ | $R^{5b}$ | Salt form melting point |
|---|---|---|---|---|---|---|---|
| | | | 2-yl | | | | |
| 130 | B12 | H | 2-benzothiazolyl | H | Cl | H | |
| 131 | B15a | H | 2-benzothiazolyl | H | CL | H | |
| 132 | B15b | $CH_3$ | 2-benzothiazolyl | H | Cl | H | 240° C. |
| 414 | B12 | H | 5-phenyl-1,3,4-thiazol-2-yl | H | H | Cl | 128° C. |
| 415 | B17a | Cl | 2-benzothiazolyl | H | Cl | H | |
| 416 | B17b | $NH_2$ | 2-benzothiazolyl | H | Cl | H | 140° C. |
| 417 | B4c | HO | $CN—CH_2—$ | $CF_3$ | Cl | Cl | |
| 418 | B16 | $CH_3O$ | 2-benzothiazolyl | H | Cl | H | 100° C. |
| 419 | B20 | H | (4-phenyl-2-thiazolyl)-$CH_2$— | H | H | Cl | 90° C. |
| 420 | B19a | H | $HO—CH_2—$ | H | Cl | Cl | |
| 421 | B5a | H | 2-benzothiazolyl | H | Cl | Cl | 208° C. |
| 422 | B19c | H | (2-pyrimidinyl)thio-$CH_2$— | H | H | Cl | |
| 423 | B19a | H | $HO—CH_2—$ | $CF_3$ | Cl | Cl | |
| 424 | B19b | H | $H_3C—SO_2—O—CH_2—$ | $CF_3$ | Cl | Cl | |
| 425 | B5a | H | 1-$CH_3$-4-phenyl-2-imidazolyl | H | Cl | Cl | >250° C. |
| 426 | B8a | H | 5-$CH_3$-4-phenyl-2-oxazolyl | H | Cl | Cl | 150° C. |
| 427 | B12 | H | 5-phenyl-1,3,4-thiadiazol-2-yl | H | Cl | Cl | 140° C. |
| 428 | B5a | H | 4-$CH_3$-5-phenyl-1,2,4-triazol-3-yl | H | Cl | Cl | $H_2O$ (1:1)/ 245° C. |
| 429 | B6b | H | 3-phenyl-1,2,4-oxadiazol-5-yl | H | Cl | Cl | 128° C. |
| 430 | B5a | H | 1-$CH_3$-2-phenyl-5-imidazolyl | H | Cl | Cl | >260° C. |
| 431 | B8a | H | 5-$CH_3$-4-(4-F-phenyl)-2-oxazolyl | H | Cl | Cl | 220° C. |
| 432 | B21 | H | 5-phenylimidazo[2,1-b]thiazol-6-yl | H | H | Cl | |
| 433 | B21 | H | 5,6-dihydro-2-phenylimidazo-[2,1-b]thiazol-3-yl | H | H | Cl | |
| 434 | B5a | H | 2,4-diphenyl-5-oxazolyl | H | Cl | Cl | 195° C. |
| 435 | B19b | H | $H_3C—SO_2—O—CH_2—$ | H | Cl | Cl | |

C. Pharmacological Example

EXAMPLE C1

In Vitro Inhibition of IL-5 Production in Human Blood

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 μg/ml streptomycin, and 300 μl fractions were distributed in 24-well multidisc plates. Blood samples were preincubated (60 minutes at 37° C.) in a humidified 6% $CO_2$-atmosphere with 100 μl of drug solvent (final concentration 0.02% dimethylsulfoxide in RPMI 1640) or with 100 μl of an appropriate dose of test compound before being stimulated by the addition of 100 μl of phytohemagglutinin HA17 (Murex, UK) at a final concentration of 2 μg/ml. After 48 hours, cell-free supernatant fluids were collected by centrifugation and stored at −70° C. until tested for the presence of IL-5.

IL-5-Measurements

IL-5 measurements were conducted as described in Van Wauwe et al. (1996, Inflamm Res, 45, 357–363) on page 358 using ELISA.

Table 9 lists the percentage inhibition of IL-5 production (column "% inh") at a test dose of $1\times10^{-6}$ M, or in case the percentage inhibition is marked with an "*" $1\times10^{-5}$ M, the compounds of the present invention.

TABLE 9

| Comp No | % inh. |
|---|---|
| 1 | 77 |
| 2 | 55* |
| 3 | 46 |
| 4 | 83 |
| 5 | 77 |
| 6 | 91 |
| 7 | 95 |
| 8 | 93 |
| 9 | 85 |
| 10 | 64 |
| 11 | 91 |
| 12 | 77 |
| 13 | 61 |
| 14 | 83 |
| 15 | 86 |
| 16 | 89 |
| 17 | 81 |
| 18 | 88 |
| 19 | 83 |
| 20 | 70 |

TABLE 9-continued

| Comp No | % inh. |
|---|---|
| 21 | 91 |
| 22 | 93 |
| 23 | 83 |
| 24 | 74 |
| 25 | 88 |
| 26 | 85 |
| 27 | 64 |
| 28 | 73 |
| 29 | 95 |
| 30 | 57 |
| 31 | 93 |
| 32 | 90 |
| 34 | 58 |
| 35 | 56 |
| 37 | 61 |
| 38 | 92 |
| 39 | 68 |
| 40 | 31 |
| 41 | 11 |
| 42 | 57 |
| 43 | 37 |
| 44 | 40 |
| 46 | 64 |
| 47 | 33 |
| 48 | 29 |
| 49 | 61 |
| 50 | 20* |
| 51 | 10 |
| 52 | 57* |
| 53 | 53* |
| 54 | 14 |
| 55 | 26 |
| 56 | 41 |
| 57 | 50 |
| 58 | 5 |
| 59 | 76 |
| 60 | 24* |
| 61 | 14 |
| 62 | 30 |
| 63 | 68 |
| 64 | 64 |
| 65 | 50 |
| 66 | 64 |
| 67 | 69 |
| 68 | 60 |
| 70 | 51 |
| 71 | 84 |
| 73 | 21 |
| 74 | 69 |
| 75 | 72 |
| 76 | 2 |
| 77 | 65 |
| 78 | 70 |
| 79 | 74 |
| 81 | 76 |
| 82 | 19 |
| 84 | 73 |
| 85 | 38 |
| 86 | 84 |
| 87 | 9 |
| 88 | 26 |
| 89 | 19 |
| 90 | 60 |
| 93 | 86 |
| 94 | 18 |
| 95 | 17 |
| 96 | 62 |
| 97 | 26 |
| 101 | 66 |
| 102 | 14 |
| 103 | 63 |
| 104 | 60 |
| 105 | 88 |
| 106 | 77 |
| 107 | 81 |
| 109 | 35 |

TABLE 9-continued

| Comp No | % inh. |
|---|---|
| 110 | 6 |
| 111 | 61 |
| 112 | 62 |
| 113 | 76 |
| 114 | 40 |
| 115 | 71 |
| 116 | 74 |
| 117 | 34 |
| 118 | 34 |
| 119 | 72* |
| 120 | 10 |
| 123 | 13 |
| 124 | 42 |
| 125 | 52 |
| 126 | 40 |
| 127 | 94 |
| 130 | 70 |
| 131 | 76 |
| 132 | 55 |
| 133 | 50 |
| 134 | 95 |
| 135 | 88 |
| 136 | 93 |
| 137 | 64 |
| 138 | 81 |
| 139 | 60 |
| 140 | 45 |
| 141 | 64 |
| 142 | 80 |
| 143 | 81 |
| 144 | 40 |
| 145 | 37 |
| 146 | 83 |
| 147 | 50 |
| 148 | 79 |
| 149 | 89 |
| 150 | 48 |
| 151 | 17 |
| 152 | 87 |
| 153 | 72 |
| 154 | 42 |
| 155 | 80 |
| 156 | 91 |
| 157 | 85 |
| 158 | 92 |
| 159 | 87 |
| 160 | 91 |
| 161 | 91 |
| 162 | 63 |
| 163 | 90 |
| 164 | 84 |
| 165 | 80 |
| 166 | 87 |
| 167 | 82 |
| 168 | 80 |
| 169 | 81 |
| 170 | 62 |
| 171 | 59 |
| 172 | 17 |
| 173 | 44 |
| 174 | 83 |
| 175 | 58 |
| 176 | 3 |
| 177 | 69 |
| 178 | 78 |
| 179 | 21 |
| 180 | 54 |
| 181 | 55 |
| 182 | 75 |
| 184 | 83 |
| 185 | 81 |
| 186 | 8 |
| 187 | 25 |
| 188 | 95 |
| 189 | 82 |
| 190 | 83 |

TABLE 9-continued

| Comp No | % inh. |
|---|---|
| 191 | 19 |
| 194 | 83 |
| 195 | 7 |
| 196 | 35 |
| 198 | 46 |
| 199 | 43 |
| 200 | 43 |
| 201 | 87 |
| 203 | 82 |
| 204 | 36 |
| 205 | 80 |
| 206 | 82 |
| 207 | 94 |
| 208 | 48 |
| 209 | 77 |
| 210 | 79 |
| 211 | 83 |
| 213 | 32 |
| 215 | 54 |
| 218 | 4 |
| 219 | 8 |
| 220 | 25 |
| 221 | −2 |
| 224 | 95 |
| 225 | 80 |
| 226 | 93 |
| 227 | 78 |
| 228 | 81 |
| 230 | 79 |
| 232 | 47 |
| 233 | 84 |
| 234 | 83 |
| 235 | 79 |
| 236 | 92 |
| 237 | 82 |
| 238 | 74 |
| 239 | 72 |
| 240 | 54 |
| 241 | 95 |
| 242 | 98 |
| 243 | 97 |
| 244 | 95 |
| 245 | 98 |
| 246 | 94 |
| 247 | 80 |
| 248 | 91 |
| 249 | 80 |
| 250 | 84 |
| 251 | 90 |
| 252 | 80 |
| 253 | 96 |
| 254 | 86 |
| 255 | 67 |
| 256 | 94 |
| 257 | 82 |
| 258 | 98 |
| 259 | 95 |
| 260 | 98 |
| 261 | 93 |
| 262 | 93 |
| 263 | 92 |
| 264 | 79 |
| 266 | 46 |
| 267 | 81 |
| 268 | 83 |
| 269 | 90 |
| 270 | 86 |
| 271 | 88 |
| 272 | 87 |
| 273 | 77 |
| 274 | 89 |
| 275 | 94 |
| 276 | 91 |
| 277 | 66 |
| 278 | 97 |
| 279 | 92 |

TABLE 9-continued

| Comp No | % inh. |
|---|---|
| 280 | 96 |
| 281 | 91 |
| 282 | 93 |
| 283 | 93 |
| 284 | 91 |
| 285 | 89 |
| 286 | 86 |
| 287 | 94 |
| 288 | 90 |
| 289 | 96 |
| 290 | 92 |
| 292 | 94 |
| 293 | 59 |
| 294 | 85 |
| 295 | 90 |
| 296 | 92 |
| 297 | 90 |
| 299 | 38 |
| 300 | 27 |
| 301 | 33 |
| 302 | 87 |
| 303 | 85 |
| 304 | 35 |
| 305 | 51 |
| 306 | 92 |
| 307 | 78 |
| 309 | 82 |
| 310 | 79 |
| 311 | 64 |
| 312 | 57 |
| 313 | 86 |
| 314 | 81 |
| 315 | 93 |
| 316 | 85 |
| 317 | 67 |
| 318 | 81 |
| 319 | 84 |
| 320 | 94 |
| 321 | 92 |
| 322 | 96 |
| 325 | 95 |
| 326 | 89 |
| 327 | 84 |
| 329 | 88 |
| 330 | 94 |
| 331 | 95 |
| 332 | 86 |
| 333 | 61 |
| 334 | 75 |
| 335 | 52 |
| 336 | 88 |
| 337 | 96 |
| 338 | −15 |
| 339 | 35 |
| 340 | 88 |
| 341 | 96 |
| 342 | 93 |
| 343 | 66 |
| 344 | 82 |
| 345 | 88 |
| 346 | 86 |
| 347 | 8 |
| 348 | 83 |
| 349 | 87 |
| 351 | 62 |
| 352 | 85 |
| 353 | 91 |
| 354 | 70 |
| 355 | 83 |
| 357 | 69 |
| 358 | 63 |
| 359 | 88 |
| 360 | 84 |
| 361 | 28 |
| 363 | 91 |
| 364 | 95 |

TABLE 9-continued

| Comp No | % inh. |
|---|---|
| 365 | 88 |
| 366 | 93 |
| 367 | 74 |
| 368 | 88 |
| 369 | 66 |
| 370 | 76 |
| 371 | 88 |
| 372 | 86 |
| 373 | 40 |
| 374 | 94 |
| 375 | 91 |
| 376 | 92 |
| 377 | 87 |
| 378 | 91 |
| 379 | 95 |
| 380 | 95 |
| 381 | 95 |
| 382 | 95 |
| 383 | 78 |
| 384 | 95 |
| 385 | 95 |
| 386 | 97 |
| 387 | 93 |
| 388 | 90 |
| 389 | 91 |
| 390 | 89 |
| 391 | 97 |
| 392 | 87 |
| 393 | 93 |
| 394 | 93 |
| 395 | 94 |
| 396 | 28 |
| 397 | 83 |
| 398 | 96 |
| 399 | 93 |
| 400 | 76 |
| 401 | 92 |
| 402 | 90 |
| 403 | 97 |
| 404 | 92 |
| 405 | 80 |
| 406 | 84 |
| 407 | 71 |
| 408 | 88 |
| 409 | 88 |
| 410 | 15 |
| 411 | 94 |
| 412 | 16 |
| 413 | 59 |
| 414 | 30 |
| 416 | 79 |
| 418 | 47 |
| 419 | 5 |
| 420 | 33 |
| 421 | 86 |
| 422 | 87 |
| 425 | 70 |
| 426 | 92 |
| 427 | 72 |
| 428 | 66 |
| 429 | 78 |
| 430 | 89 |
| 431 | 67 |
| 432 | 82 |
| 433 | 53 |
| 434 | 72 |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

EXAMPLE D1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10,000 tablets, each comprising 10 mg of the active ingredient.

Coating

To a solution of methyl cellulose (10 g) in denaturated ethanol (75 ml) there was added a solution of ethyl cellulose (5 g) in $CH_2C_2$ (150 ml). Then there were added $CH_2Cl_2$(75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

EXAMPLE D2

2% Topical Cream

To a solution of hydroxypropyl β-cyclodextrine (200 mg) in purified water is added A.I. (20 mg) while stirring. Hydrochloric acid is added until complete dissolution and next sodium hydroxide is added until pH 6.0. While stirring, glycerol (50 mg) and polysorbate 60 (35 mg) are added and the mixture is heated to 70° C. The resulting mixture is added to a mixture of mineral oil (100 mg), stearyl alcohol (20 mg), cetyl alcohol (20 mg), glycerol monostearate (20 mg) and sorbate 60 (15 mg) having a temperature of 70° C. while mixing slowly. After cooling down to below 25° C., the rest of the purified water q.s. ad 1 g is added and the mixture is mixed to homogenous.

What is claimed is:

1. A compound of formula (I)

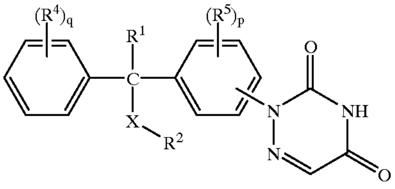

a N-oxide, a pharmaceutically acceptable addition salt or a stereochemically isomeric form thereof, wherein:

p represents an integer being 0, 1, or 2;

q represents an integer being 0, 1, or 2;

X represents O, S, $NR^3$ or a direct bond;

$R^1$ represents hydrogen, hydroxy, halo, amino, $C_{1-6}$alkyl, $C_{1-6}$alkyloxy or mono- or di($C_{1-4}$alkyl)amino$C_{1-4}$alkylamino; in particular, hydrogen, methyl and hydroxy;

$R^2$ represents oxadiazolyl, thiazolyl, pyrimidinyl or pyridinyl; wherein said heterocycles each independently may optionally be substituted with one, or where possible, two or three substituents each independently selected from $Het^2$, $R^{11}$ and $C_{1-4}$alkyl optionally substituted with $Het^2$ or $R^{11}$;

each $R^4$ independently represents $C_{1-6}$alkyl, halo, polyhalo$C_{1-6}$alkyl or $C_{1-6}$alkyloxy;

each $R^5$ independently represents $C_{1-6}$alkyl, halo or $C_{1-6}$alkyloxy;

each $R^6$ independently represents $C_{1-6}$alkylsulfonyl, aminosulfonyl or phenyl$C_{1-6}$alkylsulfonyl;

each $R^7$ and each $R^8$ are independently selected from hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, mono- or di($C_{1-4}$alkyl)amino$C_{1-4}$alkyl, arylaminocarbonyl, arylaminothiocarbonyl, $C_{3-7}$cycloalkyl, pyridinyl$C_{1-4}$alkyl, $Het^3$ and $R^6$;

$R^9$ and $R^{10}$ are each independently selected from hydrogen, $C_{1-4}$alkyl, $C_{1-4}$alkylcarbonyloxy$C_{1-4}$alkylcarbonyl, hydroxy$C_{1-4}$alkylcarbonyl, $C_{1-4}$alkyloxycarbonylcarbonyl, $Het^3$aminothiocarbonyl and $R^6$;

each $R^{11}$ independently being selected from hydroxy, mercapto, cyano, nitro, halo, trihalomethyl, $C_{1-4}$alkyloxy, carboxyl, $C_{1-4}$alkyloxycarbonyl, trihalo$C_{1-4}$alkylsulfonyloxy, $R^6$, $NR^7R^8$, C(=O)$NR^7R^8$, aryl, aryloxy, arylcarbonyl, $C_{3-7}$cycloalkyl, $C_{3-7}$cycloalkyloxy, phthalimide-2-yl, $Het^3$ and C(=O)$Het^3$;

$R^{12}$ and $R^{13}$ are each independently selected from hydrogen and $C_{1-4}$alkyl;

aryl represents phenyl optionally substituted with one, two or three substituents each independently selected from nitro, azido, halo, hydroxy, $C_{1-4}$alkyl, $C_{1-4}$alkyloxy, polyhalo$C_{1-4}$alkyl, $NR^9R^{10}$, $R^6$, phenyl, $Het^3$ and $C_{1-4}$alkyl substituted with $NR^9R^{10}$;

$Het^1$ represents a heterocycle selected from a heterocycle selected from imidazolyl, triazolyl, furanyl, oxazolyl, thiazolyl, thiazolinyl, thiadiazolyl, oxadiazolyl, pyridinyl, pyrimidinyl, pyrazinyl, piperidinyl, piperazinyl, triazinyl, benzothiazolyl, benzoxazolyl, purinyl, 1H-pyrazolo-[3,4-d]pyrimidinyl, benzimidazolyl, thiazolopyridinyl, oxazolopyridinyl, imidazo-[2,1-b]thiazolyl; wherein said heterocycles each independently may optionally be substituted with one, or where possible, two or three substituents each independently selected from $Het^2$, $R^{11}$ and $C_{1-4}$alkyl optionally substituted with $Het^2$ or $R^{11}$;

$Het^2$ represents furanyl, thienyl or pyridinyl; wherein said monocyclic heterocycles each independently may optionally be substituted with $C_{1-4}$alkyl;

$Het^3$ represents pyrrolidinyl, piperidinyl, piperazinyl, morpholinyl, thiomorpholinyl; wherein said monocyclic heterocycles each independently may optionally be substituted with, where possible, one, two or three substituents each independently selected from $C_{1-4}$alkyl, $C_{1-4}$alkyloxy, $C_{1-4}$alkyloxycarbonyl, $C_{1-4}$alkylcarbonyl, phenyl$C_{1-4}$alkyl, piperidinyl, $NR^{12}R^{13}$ and $C_{1-4}$alkyl substituted with $NR^{12}R^{13}$.

2. A compound according to claim 1 wherein the 6-azauracil moiety is in the para position relative to the central carbon atom.

3. A compound according to claim 2 wherein q is 1 or 2 and one $R^4$ substituent is in the 4 position; and p is 1 or 2 and the one or two $R^5$ substituents are in the ortho position relative to the central carbon atom.

4. A composition comprising a pharmaceutically acceptable carrier and, as active ingredient, a therapeutically effective amount of a compound as claimed in claim 1.

5. A process for preparing a composition as claimed in claim 4, wherein a pharmaceutically acceptable carrier is intimately mixed with a therapeutically effective amount of a compound as defined in claim 1.

6. A method for treating bronchial asthma, atopic dermatitis, allergic-rhinitis or allergic conjunctivitis in a warm-blooded animal in need thereof comprising administering to the warm-blooded animal an effective amount of a compound of claim 1.

7. A method for inhibiting IL-5 production in a warm-blooded animal, comprising administering to the warm-blooded animal an effective amount of a compound of claim 1.

* * * * *